United States Patent
Zhang

(10) Patent No.: US 6,534,657 B2
(45) Date of Patent: Mar. 18, 2003

(54) CHIRAL FERROCENE PHOSPHINES AND THEIR USE IN ASYMMETRIC CATALYTIC REACTIONS

(75) Inventor: Xumu Zhang, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 143 days.

(21) Appl. No.: 09/781,083

(22) Filed: Feb. 9, 2001

(65) Prior Publication Data

US 2002/0091280 A1 Jul. 11, 2002

Related U.S. Application Data

(60) Provisional application No. 60/181,448, filed on Feb. 10, 2000, and provisional application No. 60/214,167, filed on Jun. 26, 2000.

(51) Int. Cl.[7] .......................... C07F 17/02; B01J 31/00; C07C 33/02; C07D 207/00

(52) U.S. Cl. .................. 548/101; 548/402; 548/433; 548/533; 556/11; 556/12; 556/18; 556/22; 556/33; 556/34; 556/40; 560/128; 560/190; 560/203; 568/715; 568/881; 568/886; 502/154; 502/162; 502/165; 502/166

(58) Field of Search ................. 556/11, 12, 18, 556/22, 33, 34, 40; 548/101, 402, 433, 533; 560/128, 190, 203; 568/715, 881, 886; 502/154, 162, 165, 166

(56) References Cited

FOREIGN PATENT DOCUMENTS

WO   WO 01/58588 A1 * 8/2001

OTHER PUBLICATIONS

Nishibayashi et al. "Asymmetric Synthesis and Highly Diastereoselective ortho–Lithiation of Oxazolinylferrocenes." *Synlett.* Jan. 1995, pp. 79–81.

Richards et al. "Synthesis of 2–[2–(Diphenylphosphino)ferrocenyl]oxazoline Ligands." *Synlett.* Jan. 1995, pp. 74–76.

Nagel et al. "Synthese N–substituierter (R,R)–3,4–Bis-(diphenylphosphino)–pyrrolidine und Anwendung ihrer Rhodiumkomplexe zur asymmetrischen Hydrienrung von α–(Acylaminoacrylsaure–Derivaten." *Chem. Ber.* 119, 3326–3343 (1986).

Togni. "Planar–Chiral Ferrocenes: Synthetic Methods and Applications," *Angew. Chem. Int. Ed. Engl.* 1996, 35, No. 13/14.

Hughbanks. "Inorganic Chemistry." *Chemistry & Industry.* Jan. 15, 1996, pp. 62–63.

Sawamura et al. "trans–Chelating Chiral Diphosphane Ligands Bearing Flexible P–Alkyl Substituents (Alkyl-TRAPs) and their Application to the Rhodium–Catalyzed Asymmetric Hydrosilylation of Simple Ketones." *Angew. Chem. Int. Ed. Engl.* 1994, 33, No. 1.

Grigg et al. "1,3–Dipolar Cycloaddition Reactions of Imines of γ–and 6–Dialdehydes: Applications to the Synthesis of Novel Polyfunctional Pyrrolizidines and Indolizidines," *Synthesis.* 1999, No. 3, 441–446.

Sakai et al. "Highly Enantioselective Hydroformylation of Olefins Catalyzed by New Phosphinephosphite–Rh(I) Complexes." *J. Am. Chem. Soc.* 1993, 115, 7033–7034.

Burk et al. "Preparation and Use of $C_2$–Symmetric Bis(phospholanes): Production of α–Amino Acid Derivatives via Highly Enantioselective Hydrogenation Reactions." *J. Am. Chem. Soc.* 1993, 115, 10125–10138.

Uozumi et al. "Catalytic Asymmetric Synthesis of Optically Active 2–Alkanols via Hydrosilylation of 1–Alkenes with a Chiral Monophosphine–Palladium Catalyst." *J. Am. Chem. Soc.* 1991, 113, 9887–9888.

Miyashita et al. "Synthesis of 2,2'–Bis(diphenylphosphino)–1,1'–binaphthyl (BINAP), and Atropisomeric Chiral Bis(triaryl)phosphine, and Its Use in the Rhodium(I)–Catalyzed Asymmetric Hydrogenation of α–(Acylaminoacrylic Acids." *J. Amer. Chem. Soc.* 1980, 102, 7932–7934.

Fryzuk et al. "Asymmetric Synthesis. Production of Optically Active Amino Acids by Catalytic Hydrogenation." *J. Amer. Chem. Soc.* 99:19, Sep. 14, 1977, 6262–6267.

Achiwa. "Asymmetric Hydrogenation with New Chiral Functionalized Biphosphine–Rhodium Complexes."*J. Amer. Chem. Soc,.* 98:25, Dec. 8, 1976, 8265–8266.

Anastassiou et al. "An Examination of the Heteronins by [13]C Nuclear Magnetic Resonance." *J. Amer. Chem. Soc.*, 98:25, Dec. 8, 1976, 8266–8267.

Kagan et al. "Asymmetric Catalytic Reduction with Transition Metal Complexes . . . " *J. Amer. Chem. Soc.*, 94:18, Sep. 6, 1972, 6429–6433.

Trost et al. "Asymmetric Transition Metal–Catalyzed Allylic Alkylations." *Chem. Rev.* 1996, 395–422.

Knowles et al. "Catalytic Asymmetric Hydrogenation." *J.C.S. Chem. Comm.*, 1972, 10–11.

Ojima et al. "N–Carbamoyl–4–Diphenylphosphino–2–Diphenylphosphinomethylpyrrolidines (CAPP). Efficient New Chiral Ligands for Asymmetric Hydrogenation." *Tetrahedron Letters.* vol. 21, pp. 1051–1054.

(List continued on next page.)

*Primary Examiner*—Porfirio Nazario-Gonzalez
(74) *Attorney, Agent, or Firm*—Ohlandt, Greeley, Ruggiero & Perle, L.L.P.

(57) ABSTRACT

Ferrocene anchored chiral ligands and metal complexes based on such chiral ligands useful in asymmetric catalysis are disclosed. The metal complexes according to the present invention are useful as catalysts in asymmetric reactions, such as, hydrogenation, hydride transfer, allylic alkylation, hydrosilylation, hydroboration, hydrovinylation, hydroformylation, olefin metathesis, hydrocarboxylation, isomerization, cyclopropanation, Diels-Alder reaction, Heck reaction, isomerization, Aldol reaction, Michael addition; epoxidation, kinetic resolution and [m+n] cycloaddition. The new ligands are effective for asymmetric Pd-catalyzed allylic alkylation reactions and Ag-catalyzed [3+2] cyclization of azomethine ylides.

60 Claims, No Drawings

OTHER PUBLICATIONS

Noyori et al. "BINAP: An Efficient Chiral Element for Asymmetric Catalysis." *Acc. Chem. Res.* 1990, 23, 345–350.

Knowles. "Asymmetric Hydrogenation." *Acc. Chem. Res.* 1983, 16, 106–112.

Hayashi et al. "Asymmetric Synthesis Catalyzed by Transition–Metal complexes with Functionalized Chiral Ferrocenylphosphine Ligands." *Acc. Chem. Res.* 1982, 15, 395–401.

Pfaltz. "Chiral Semicorrins and Related Nitrogen Heterocycles as ligands in Asymmetric Catalysis." *Acc. Chem. Res.* 1993, 26, 339–345.

Gozler et al. "Konyanin: A New Lignan From Haplophyllum Vulcanicum." *Tetrahedron*, vol. 40, No. 7, pp. 1145–1150, 1984.

* cited by examiner

CHIRAL FERROCENE PHOSPHINES AND THEIR USE IN ASYMMETRIC CATALYTIC REACTIONS

This application claims priority from U.S. Provisional Application Ser. No. 60/181,448, filed Feb. 10, 2000, and U.S. Provisional Application Ser. No. 60/214,167, filed Jun. 26, 2000.

STATEMENT OF GOVERNMENT RIGHTS

The Government of the United States has rights in this invention pursuant to Grant No. NIH GM 58832-01A1 awarded by the National Institute of Health.

BACKGROUND OF THE INVENTION

1. Field of the Invention

The present invention relates to novel chiral ligands derived from ferrocenes and catalysts prepared therefrom for applications in asymmetric catalysis. More particularly, the present invention relates to transition metal complexes of these chiral phosphine ligands. The transition metal complexes according to the present invention are useful as catalysts in asymmetric reactions, such as, hydrogenation, hydride transfer, allylic alkylation, hydrosilylation, hydroboration, hydrovinylation, hydroformylation, olefin metathesis, hydrocarboxylation, isomerization, cyclopropanation, Diels-Alder reaction, Heck reaction, isomerization, Aldol reaction, Michael addition; epoxidation, kinetic resolution and [m+n] cycloaddition.

2. Description of the Prior Art

Molecular chirality plays an important role in science and technology. The biological activities of many pharmaceuticals, fragrances, food additives and agrochemicals are often associated with their absolute molecular configuration. A growing demand in pharmaceutical and fine chemical industries is to develop cost-effective processes for the manufacture of single-enantiomeric products. To meet this challenge, chemists have explored many approaches for acquiring enantiomerically pure compounds ranging from optical resolution and structural modification of naturally occurring chiral substances to asymmetric catalysis using synthetic chiral catalysts and enzymes. Among these methods, asymmetric catalysis is perhaps the most efficient because a small amount of a chiral catalyst can be used to produce a large quantity of a chiral target molecule [Book, Ojima, I., Ed. *Catalytic Asymmetric Synthesis,* VCH, New York, 1993 and Noyori, R. *Asymmetric Catalysis In Organic Synthesis,* John Wiley & Sons, Inc., New York, 1994].

Asymmetric hydrogenation accounts for major part of all asymmetric synthesis on a commercial scale. Some dramatic examples of industrial applications of asymmetric synthesis include Monsanto's L-DOPA synthesis (asymmetric hydrogenation of a dehydroamino acid, 94% ee, 20,000 turnovers with a Rh-DIPAMP complex) [Knowles, W. S. *Acc. Chem. Res.* 1983, 16, 106], Takasago's L-menthol synthesis (asymmetric isomerization, 98% ee, 300,000 turnovers with a Rh-BINAP complex) [Noyori, R.; Takaya, H. *Acc. Chem. Res.* 1990, 23, 345] and Norvatis' (S)-Metolachlor synthesis (asymmetric hydrogenation of an imine, 80% ee, 1,000,000 turnovers with an Ir-ferrocenyl phosphine complex) [Spindler, F.; Pugin, B.; Jalett, H.-P., Buser, H.-P.; Pittelkow, U.; Blaser, H,-U., Altanta, 1996; Chem. Ind. (Dekker), 1996, 63 and Tongni, A. *Angew. Chem.. Int. Ed Engl.* 1996, 356, 14575].

Invention of chiral ligands for transition metal-catalyzed reactions plays a critical role in asymmetric catalysis. Not only the enantioselectivity depends on the framework of chiral ligands, reactivities can often be altered by changing the steric and electronic structure of the ligands. Since small changes in the ligand can influence the (delta)(delta)G of the rate-determining step, it is very hard to predict which ligand can be effective for any particular reaction or substrate. Development of new structural motifs is important in the process of ligand development.

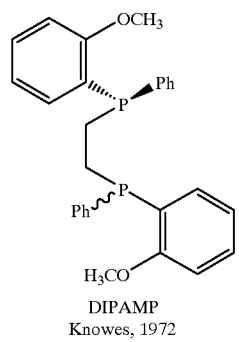

DIPAMP
Knowes, 1972

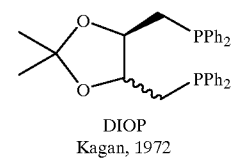

DIOP
Kagan, 1972

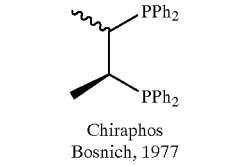

Chiraphos
Bosnich, 1977

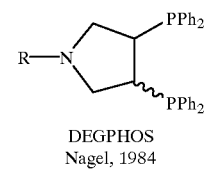

DEGPHOS
Nagel, 1984

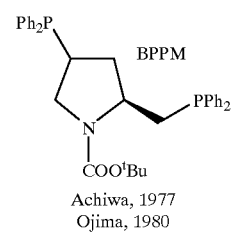

BPPM
Achiwa, 1977
Ojima, 1980

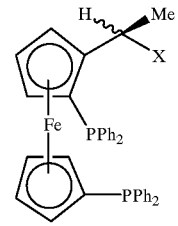

Hayashi, Kumada, Ito, 1978

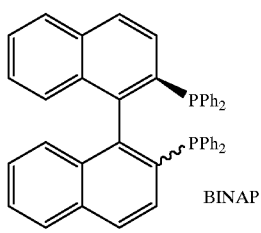

BINAP
Noyori, Takaya, Otsuka, 1980

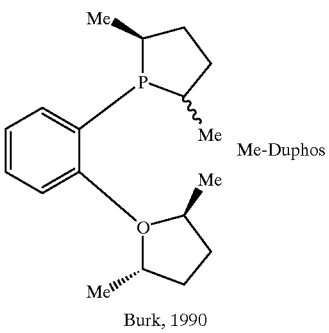

Me-Duphos
Burk, 1990

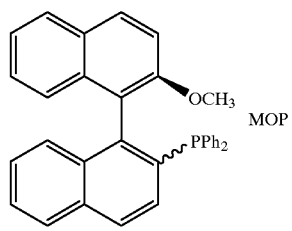

MOP
Hayashi, 1991

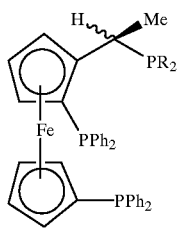

Togni, 1991

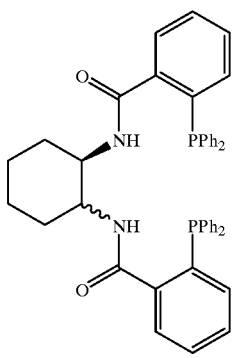

Trost, 1992

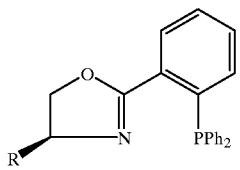

Pfaltz, Helmchen, 1993

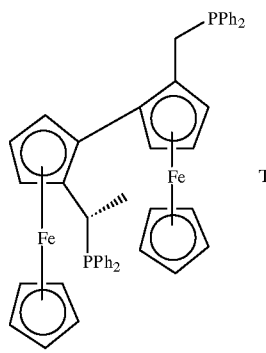

TRAP
Ito, 1992

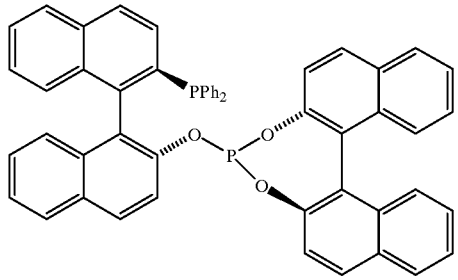

BINAPHOS
Takaya, 1993

Several important chiral phosphines have been studied during 30 years. Knowles' DIPAMP [Knowles, W. S.; Sabacky, M. J.; Vineyard, B. D. *J. Chem. Soc., Chem. Commun.* 1972, 10] and Kagan's DIOP [Kagan, H. B.; Dang, T.-P. *J. Am. Chem. Soc.* 1972, 94, 6429] ligands were reported for Rh (I)-catalyzed asymmetric hydrogenation at about the same time. The great success in asymmetric hydrogenation of dehydroamino acids has stimulated continuing research on new chiral phosphine ligands. Various bidentate chiral diphosphines such as Chiraphos (Bosnich) [Fryzuk, M. D.; Bosnich, B. *J. Am. Chem. Soc.* 1977, 99, 6262], BPPM (Achiwa, Ojima) [(a) Achiwa, K. *J. Am. Chem. Soc.* 1976, 98, 8265. (b) Ojima, I.; Yoda, N. *Tetrahedron Lett.* 1980, 21, 1051], DegPhos (Nagel)[Nagel, U.; Kinzel, E.; Andrade, J.; Prescher, G. *Chem. Ber.* 1986, 119, 3326] and ferrocenyl chiral phosphines (Hayashi, Kumada, Ito)[Hayashi, T.; Kumada, M. Acc. Chem. Res., 1982, 15, 395] were discovered. Two excellent ligands come out of extensive ligand studies; BINAP (Otsuka, Nayori and Takayi)[Miyashita, A.; Yasuda, A.; Takaya, H.; Toriumi, K.; Ito, T.; Souchi, T.; Noyori, R. *J. Am. Chem. Soc.* 1980,102, 7932. Miyashita, A.; Takaya, H.; Souchi, T.; Noyori, R. *Tetrahedron* 1984, 40, 1245.] in the early 80's is one of the most frequently used bidentate chiral phosphines, and DuPhos (Burk)[Burk, M. J.; Feaster, J. E.; Nugent, W. A.; Harlow, R. L. *J. Am. Chem. Soc.* 1993, 115, 10125] in the early 90's has also shown impressive enantioselectivities. The Rh, Ru and Ir complexes of these ligands have been used as catalysts for asymmetric hydrogenations of olefins, ketones and imines. These ligands are also useful for other asymmetric reactions such as isomerization, hydroacylation, the Heck reaction, and the Grignard coupling reaction. However, there are still a variety of reactions in which only modest enantioselectivity has been achieved with these ligands, and substrate scope is limited both for hydrogenation and for other reactions. Complementary classes of chiral ligands are needed. Due to the critical role of chiral ligands in reaction activity and selectivity, many new phosphine ligands were invented. The major feature of the new chiral phosphine ligands is their structural diversity where different structural motif is created, ligand complexity increases, and the steric and electronic properties of ligands are more tunable. Some of these ligands include monodentate chiral phosphines (MOP, Hayashi) [Uozumi, Y.; Hayashi, T. *J. Am. Chem. Soc.* 1991, 113, 9887], ferrocenyl phosphine bearing two different phosphine groups (Togni) [Togni, A. *Angew. Chem. Int. Ed. Engl.* 1996, 356, 14575], Trost's chiral bisphosphines [Trost, B. M.; Van Vranken, D. L. *Chem. Rev.* 1996, 96, 395], mixed N-P ligands [Pfaltz, A. *Acc. Chem. Res.* 1993, 26, 339], Trans diphosphines (TRAP, Ito) [Sawamura, M.; Kuwano, R.; Ito, Y. *Angew. Chem. Int. Ed.Engl.* 1994, 33, 111] and phosphinite ligand (BINAPHOS, Takaya) [Sakai, N.; Mano, S.; Nozaki, K.; Takaya, H. *J. Am. Chem. Soc.* 1993, 115,7033]. These new ligands are effective for several asymmetric reactions: hydrosilylation, hydrogenation of imines, allylic alkylation, Michael addition and hydroformylation.

Although there are few chiral ferrocene phosphines reported in the literature (TRAP, Togni's ligands and Hayashi's ligands), lack of systematic studies hinders the broad utilities of chiral ferrocene phosphines for asymmetric catalytic reactions. Some of the advantages of chiral phosphines containing ferrocene backbone include the following:

1) ferrocene phosphines are generally quite stable in air and are in a solid form;
2) phosphines adjacent to a ferrocene group are electron-donating, which can aid certain catalytic reactions; and
3) chiral ferrocene phosphines can be easily generated through enantioselective deprotonation of a C—H group in the ferrocene, asymmetric reduction of ferrocene alkyl ketones or resolution methods.

The present invention includes new inventive structures derived from ferrocene s. The new ligands have been demonstrated to be effective for a range of asymmetric catalytic reactions, especially asymmetric Pd-catalyzed allylic alkylation and Ag-catalyzed [3+2] cyclization of azomethine ylides.

SUMMARY OF THE INVENTION

In broad concept, the present invention includes ferrocene anchored chiral ligands and metal complexes based on such chiral ligands useful in asymmetric catalysis. Accordingly, the present invention includes a ligand selected from the group consisting of compounds represented by the formulas:

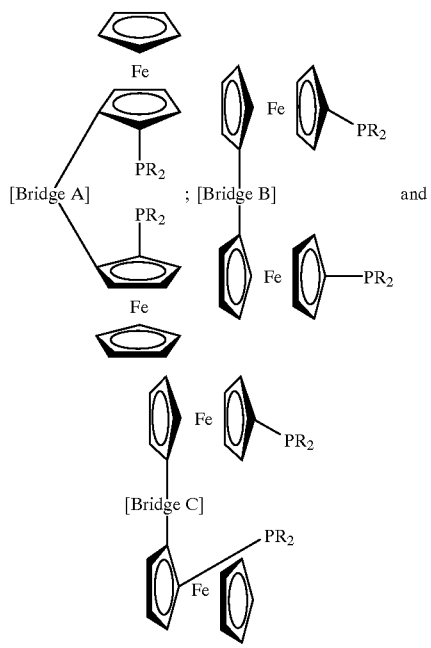

wherein "bridge A" is selected from the group consisting of: —CONH—R*—NHCO—, —CO—OR*O—CO—, —CO—R*—CO—, —CH=N—R*—N=CH—, —CH$_2$NH—R*—NHCH$_2$—, —CH$_2$NHCO—R* —CONHCH$_2$—, —C*H(R$^1$)NH—R*—NHC*H(R$^1$)—, —C*H(R$^1$)NHCO—R*—CONHC*H(R$^1$)—, —CONH— R—NHCO—, —CO—ORO—CO—, —CO—R—CO—, —CH=N—R—N=CH—, —CH$_2$NH—R—NHCH$_2$—, —CH$_2$NHCO—R—CONHCH$_2$—, —C*H(R$^1$)NH— RNH—C*H(IR)—, —C*H(R$^1$)NHCO—R—CONHC*H (R$^1$)—, C=O, C=S, SO$_2$, —PO(OR$^1$)—, —PO(NHR$^1$)—, —PO(NR$^1$$_2$)—, Si(R$^1$)$_2$ —R—*, and —R—;

wherein "bridge B" has a stereogenic carbon center, wherein said "bridge B" is selected from the group consisting of: —CONH—R*—NHCO—, —CO—OR*O—CO—, —CO—R*—CO—, —CH=N—R*—N=CH—, —CH$_2$NH—R*—NHCH$_2$—, —CH$_2$NHCO—R*— CONHCH$_2$—, —C*H(R$^1$)NH—R*—NHC*H(R$^1$)—, —C*H(R$^1$)NHCO—R*—CONHC*H(R$^1$)—, —C*H(R$^1$) NH—RNH—C*H(R$^1$)—, —C*H(R$^1$)NHCO—R— CONHC*H(R$^1$)—, and —R—*;

wherein "bridge C" is selected from the group consisting of: CO, SO$_2$, CH=CH, —CONHR*NHCO— and —(CH$_2$)n— wherein n is 0, 1 or 2; and wherein R$^1$ is selected from the group consisting of: an alkyl, aryl, aralkyl, alkaryl, and a substituted derivative thereof; —R— is selected from the group consisting of: an alkylene, arylene and a substituted derivative thereof; and * indicates the presence of a stereogenic carbon center.

The present invention also includes a ligand selected from the group consisting of compounds represented by the formulas:

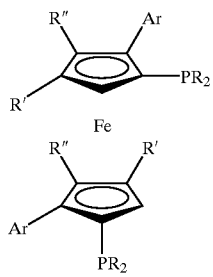

wherein R is an alkyl, aryl, substituted alkyl, substituted aryl; Ar is a susbtituted or unsubstituted aryl group; wherein Ar and R" together form an extended arene; wherein each R' and R" is independently selected from the group consisting of: H, alkyl, aryl substituted alkyl, substituted aryl, ester and alkoxy; and wherein R'—R" together form a cyclic alkyl or a extented arene.

The present invention further includes a ligand represented by the formula:

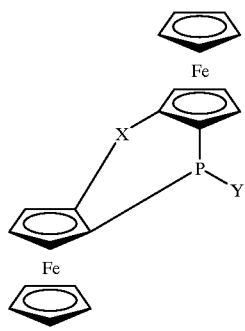

wherein X is selected from the group consisting of: CO, SO$_2$, (CH$_2$)n wherein n=0, 1 or 2, and CH=CH;
wherein Y is selected from the group consisting of: an alkyl, aryl, substituted alkyl, substituted aryl and a group represented by the formula:

—(linker)—W wherein W is represented by the formula:

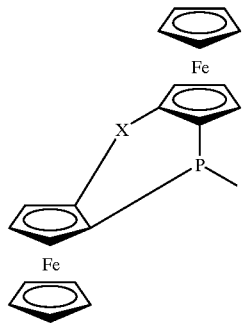

wherein X has the same meaning as above; and
wherein said "linker" is selected from the group consisting of: —(CH$_2$)$_n$— where n is an integer in the range of from 1 to 8, 1,2-divalent phenyl, 2,2'-divalent-1,1'-biphenyl, 2,2'-divalent-1,1'-binaphthyl and ferrocene, and wherein each "linker" optionally has one or more substituents, each independently selected from the group consisting of: aryl, alkyl, halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine.

The present invention still further includes a ligand represented by the formula:

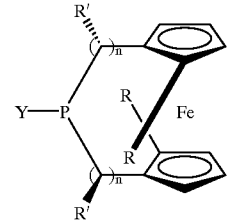

n = 0, 1 wherein R is selected from the group consisting of: H, alkyl, aryl, substituted alkyl, substituted aryl, silyl, ester, amide, oxazoline and phosphate, with the proviso that R is H when R' is not H; R' is selected from the group consisting of: H, alkyl, aryl, substituted alkyl and substituted aryl; n is 0 or 1;

Y is selected from the group consisting of: alkyl, aryl, substituted alkyl, substituted aryl and a group represented by the formula:

—(linker)—W wherein W is represented by the formula:

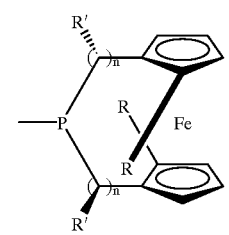

n = 0, 1 wherein said "linker" is selected from the group consisting of: —(CH$_2$)$_n$— where n is an integer in the range of from 1 to 8, 1,2-divalent phenyl, 2,2'-divalent-1,1'-biphenyl, 2,2'-divalent-1,1'-binaphthyl and ferrocene, and wherein each "linker" optionally has one or more substituents, each independently selected from the group consisting of: aryl, alkyl, halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine.

The present invention additionally includes a ligand selected from the group consisting of compounds represented by the formulas:

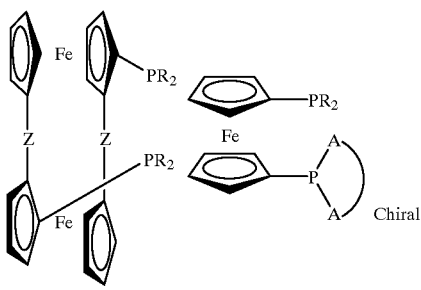

wherein R is selected from the group consisting of: alkyl, aryl, substituted is alkyl and substituted aryl; Z is selected from the group consisting of: CO, SO$_2$ and —(CH$_2$)$_n$— wherein n=0, 1 or 2; each A is independently a group containing an sp$^2$ or sp$^3$ hybridized N, O, C or S atom, wherein two A groups form a cyclic compound via a chiral connecting group selected from the group consisting of: —NHR*NH—, —OR*O—, —SR*S—, —Binol— and —CH$_2$R*CH$_2$—; wherein each R* is a chiral alkyl or aryl group.

The present invention also includes a catalyst prepared by a process comprising: contacting a transition metal salt, or a complex thereof, and a ligand selected from the group consisting of compounds represented by:

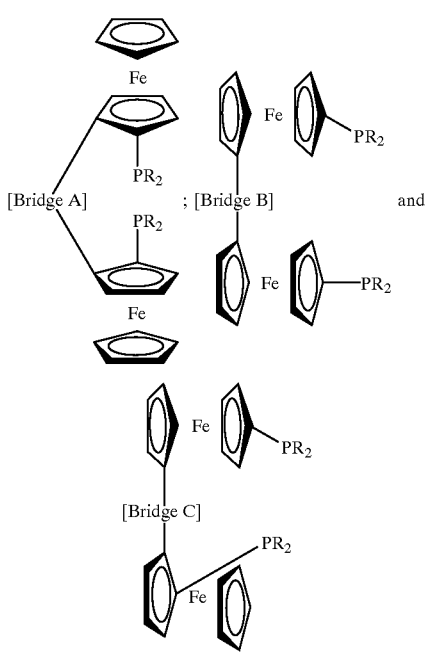

wherein "bridge A" is selected from the group consisting of: —CONH—R*—NHCO—, —CO—OR*O—CO—, —CO—R*—CO—, —CH=N—R*—N=CH—, —CH$_2$NH—R*—NHCH$_2$—, —CH$_2$NHCO—R*—CONHCH$_2$—, —C*H(R$^1$)NH—R*—NHC*H(R$^1$)—, —C*H(R$^1$)NHCO—R*—CONHC*H(R$^1$)—, —CONH—R—NHCO—, —CO—ORO—CO—, —CO—R—CO—, —CH=N—R—N=CH—, —CH$_2$NH—R—NHCH$_2$—, —CH$_2$NHCO—R—CONHCH$_2$—, —C*H(R$^1$)NH—RNH—C*H(R$^1$), —C*H(R$^1$)NHCO—R—CONHC*H(R$^1$)—, C=O, C=S, SO$_2$, —PO(OR$^1$)—, —PO(HR$^1$)—, —PO(NR$^1$$_2$)—, Si(R$^1$)$_2$—, —R—*, and —R—;

wherein "bridge B" has a stereogenic carbon center, wherein said "bridge B" is selected from the group consisting of: —CONH—R*—NHCO—, —CO—OR*O—CO—, —CO—R*—CO—, —CH=N—R*—N=CH—, —CH$_2$NH—R*—NHCH$_2$—, —CH$_2$NHCO—R*—CONHCH$_2$—, —C*H(R$^1$)NH—R*—NHC*H(R$^1$)—, —C*H(R$^1$)NHCO—R*—CONHC*H(R$^1$)—, —C*H(R$^1$)NH—RNH—C*H(R$^1$)—, —C*H(R$^1$)NHCO—R—CONHC*H(R$^1$)—, and —R—*;

wherein "bridge C" is selected from the group consisting of: CO, SO$_2$, CH=CH, —CONHR*NHCO— and —(CH$_2$)n— wherein n is 0, 1 or 2; and wherein R$^1$ is selected from the group consisting of: an alkyl, aryl, aralkyl, alkaryl, and a substituted derivative thereof; —R— is selected from the group consisting of: an alkylene, arylene and a substituted derivative thereof; and * indicates the presence of a stereogenic carbon center;

(b)

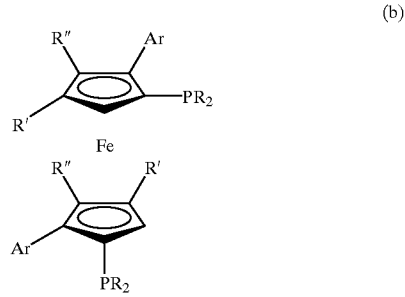

wherein R is an alkyl, aryl, substituted alkyl, substituted aryl; Ar is a susbtituted or unsubstituted aryl group; wherein Ar and R" together form an extended arene; wherein each R' and R" is independently selected from the group consisting of H, alkyl, aryl substituted alkyl, substituted aryl, ester and alkoxy; and wherein R'—R" together form a cyclic alkyl or a extented arene;

(c)

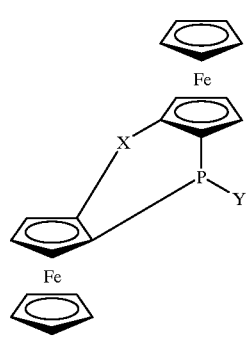

wherein X is selected from the group consisting of: CO, SO$_2$, (CH$_2$)n wherein n=0, 1 or 2, and CH=CH;

wherein Y is selected from the group consisting of: an alkyl, aryl, substituted alkyl, substituted aryl and a group represented by the formula:

—(linker)—W wherein W is represented by the formula:

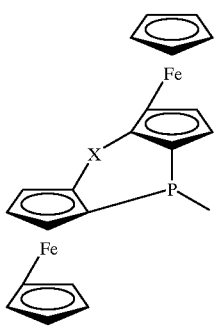

wherein X has the same meaning as above; and wherein said "linker" is selected from the group consisting of: —(CH$_2$)$_n$— where n is an integer in the range of from 1 to 8, 1,2-divalent phenyl, 2,2'-divalent-1,1'-biphenyl, 2,2'-divalent-1,1'-binaphthyl and ferrocene, and wherein each "linker" optionally has one or more substituents, each independently selected from the group consisting of: aryl, alkyl, halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine;

(d)

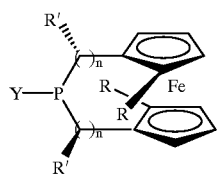

n = 0,1 wherein R is selected from the group consisting of: H, alkyl, aryl, substituted alkyl, substituted aryl, silyl, ester, amide, oxazoline and phosphate, with the proviso that R is H when R' is not H; R' is selected from the group consisting of: H, alkyl, aryl, substituted alkyl and substituted aryl; n is 0 or 1;

Y is selected from the group consisting of: alkyl, aryl, substituted alkyl, substituted aryl and a group represented by the formula:

—(linker)—W wherein W is represented by the formula:

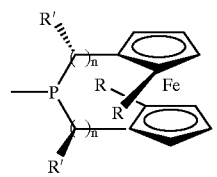

n = 0,1 wherein said "linker" is selected from the group consisting of: —(CH$_2$)$_n$— where n is an integer in the range of from 1 to 8, 1,2-divalent phenyl, 2,2'-divalent-1,1'-biphenyl, 2,2'-divalent-1,1'-binaphthyl and ferrocene, and wherein each "linker" optionally has one or more substituents, each independently selected from the group consisting of: aryl, alkyl, halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine; or (e)

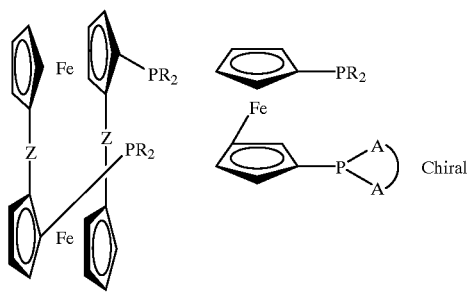

wherein R is selected from the group consisting of: alkyl, aryl, substituted alkyl and substituted aryl; Z is selected from the group consisting of: CO, SO$_2$ and —(CH$_2$)$_n$— wherein n=0, 1 or 2; each A is independently a group containing an sp$^2$ or sp$^3$ hybridized N, O, C or S atom, wherein two A groups form a cyclic compound via a chiral connecting group selected from the group consisting of: —NHR*NH—, —OR*O—, —SR*S—, —Binol— and —CH$_2$R*CH$_2$—; wherein each R* is a chiral alkyl or aryl group.

The present invention also includes a process for preparation of an asymmetric compound comprising:

contacting a substrate capable of forming an asymmetric product by an asymmetric reaction and a catalyst prepared by a process comprising: contacting a transition metal salt, or a complex thereof, and a ligand selected from the group consisting of compounds represented by:

(a)

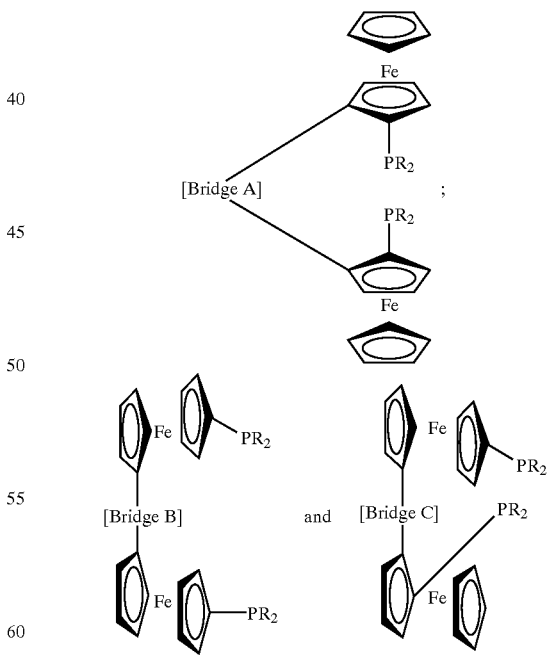

wherein "bridge A" is selected from the group consisting of: —CONH—R*—NHCO—, —CO—OR*O—CO—, —CO—R*—CO—, —CH=N—R*—N=CH—, —CH$_2$NH—R*—NHCH$_2$—, —CH$_2$NHCO—R*—CONHCH$_2$—, —C*H(R$^1$)NH—R*—NHC*H(R$^1$)—, —C*H(R¹)NHCO—R*—CONHC*H(R¹)—, —CONH—R—NHCO—, —CO—ORO—CO—, —CO—R—CO—, —CH=N—R—N=CH—, —CH₂NH—R—NHCH₂—, —CH₂NHCO—R—CONHCH₂—, —C*H(R¹)NH—RNH—C*H(R¹)—, —C*H(R¹)NHCO—R—CONHC*H(R¹)—, C=O, C=S, SO₂, —PO(OR¹)—, —PO(NHR¹)—, —PO(NR¹₂)—, Si(R¹)₂—, —R—*, and —R—;

wherein "bridge B" has a stereogenic carbon center, wherein said "bridge B" is selected from the group consisting of: —CONH—R*—NHCO—, —CO—OR* O—CO—, —CO—R*—CO—, —CH=N—R*—N=CH—, —CH₂NH—R*—NHCH₂—, —CH₂NHCO—R*—CONHCH₂—, —C*H(R¹)NH—R*—NHC*H(R¹)—, —C*H(R¹)NHCO—R*—CONHC*H(R¹)—, —C*H(R¹)NH—RNH—C*H(R¹)—, —C*H(R¹)NHCO—R—CONHC*H(R¹)—, and —R—*;

wherein "bridge C" is selected from the group consisting of: CO, SO₂, CH=CH, —CONHR*NHCO— and —(CH₂)n— wherein n is 0, 1 or 2; and wherein R¹ is selected from the group consisting of: an alkyl, aryl, aralkyl, alkaryl, and a substituted derivative thereof; —R— is selected from the group consisting of: an alkylene, arylene and a substituted derivative thereof; and * indicates the presence of a stereogenic carbon center;

(b)

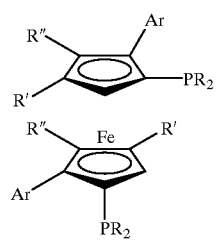

wherein R is an alkyl, aryl, substituted alkyl, substituted aryl; Ar is a susbtituted or unsubstituted aryl group; wherein Ar and R" together form an extended arene; wherein each R' and R" is independently selected from the group consisting of: H, alkyl, aryl substituted alkyl, substituted aryl, ester and alkoxy; and wherein R'—R" together form a cyclic alkyl or a extented arene;

(c)

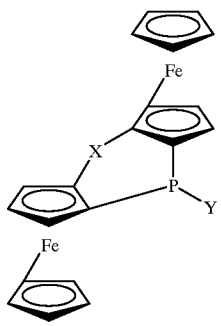

wherein X is selected from the group consisting of: CO, SO₂, (CH₂)n wherein n=0, 1 or 2, and CH=CH;

wherein Y is selected from the group consisting of: an alkyl, aryl, substituted alkyl, substituted aryl and a group represented by the formula:

—(linker)—W — wherein W is represented by the formula:

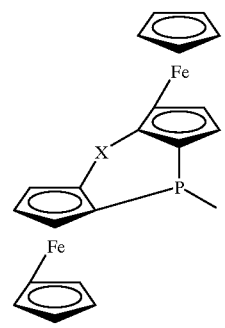

wherein X has the same meaning as above; and wherein said "linker" is selected from the group consisting of: —(CH₂)ₙ— where n is an integer in the range of from 1 to 8, 1,2-divalent phenyl, 2,2'-divalent-1,1'-biphenyl, 2,2'-divalent-1,1'-binaphthyl and ferrocene, and wherein each "linker" optionally has one or more substituents, each independently selected from the group consisting of: aryl, alkyl, halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine;

(d)

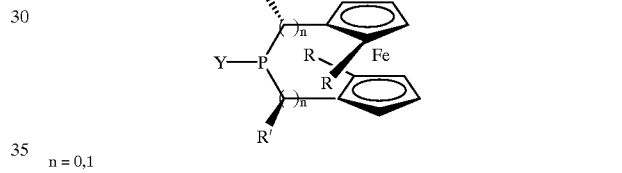

n = 0,1 wherein R is selected from the group consisting of: H, alkyl, aryl, substituted alkyl, substituted aryl, silyl, ester, amide, oxazoline and phosphate, with the proviso that R is H when R' is not H; R' is selected from the group consisting of: H, alkyl, aryl, substituted alkyl and substituted aryl; n is 0 or 1;

Y is selected from the group consisting of: alkyl, aryl, substituted alkyl, substituted aryl and a group represented by the formula:

—(linker)—W wherein W is represented by the formula:

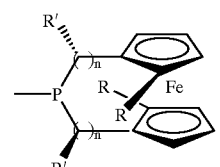

n = 0,1 wherein said "linker" is selected from the group consisting of: —(CH₂)ₙ— where n is an integer in the range of from 1 to 8, 1,2-divalent phenyl, 2,2'-divalent-1,1'-biphenyl, 2,2'-divalent-1,1'-binaphthyl and ferrocene, and wherein each "linker" optionally has one or more substituents, each independently selected from the group consisting of: aryl, alkyl, halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine; or (e)

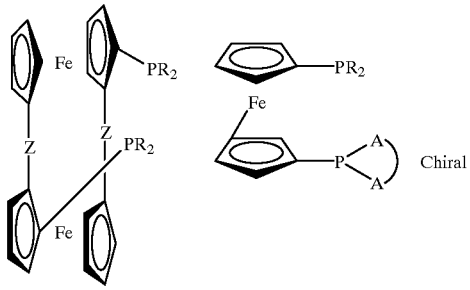

wherein R is selected from the group consisting of: alkyl, aryl, substituted alkyl and substituted aryl; Z is selected from the group consisting of: CO, $SO_2$ and —$(CH_2)_n$— wherein n=0, 1 or 2; each A is independently a group containing an $sp^2$ or $sp^3$ hybridized N, O, C or S atom, wherein two A groups form a cyclic compound via a chiral connecting group selected from the group consisting of: —NHR*NH—, —OR*O—, —SR*S—, —Binol— and —$CH_2$R*$CH_2$—; wherein each R* is a chiral alkyl or aryl group.

The present invention also includes a chiral ferrocene derivative, chiral carboxyferrocenyl diaryl phosphine, which is useful as an intermediate in the preparation of the ligands of the present invention. The chiral carboxyferrocenyl diaryl phosphine represented by the formula:

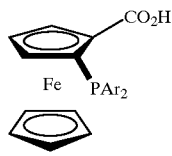

wherein each Ar is independently selected from the group consisting of phenyl and an aryl of 6 to 22 carbon atoms.

The present invention further includes a process for preparing the above chiral carboxyferrocenyl diaryl phosphine as well as processes for:

(1) preparing (S, S, S, S)-FAP 6 ligand, which comprises the step of contacting a carboxyferrocenyl diaryl phosphine and (1S, 2S)-diaminocyclohexane under reaction conditions sufficient to produce said (S, S, S, S)-FAP 6 ligand; and (2) preparing (S, R, R, S)-FAP 7 ligand comprising the step of contacting a carboxyferrocenyl diaryl phosphine and (1R, 2R)-diaminocyclohexane under reaction conditions sufficient to produce said (S, R, R, S)-FAP 7 ligand.

DETAILED DESCRIPTION OF THE INVENTION

Several new classes of chiral phosphines with ferrocene backbones are developed for asymmetric catalytic reactions. A variety of asymmetric reactions, such as, hydrogenation, hydride transfer, allylic alkylation, hydrosilylation, hydroboration, hydrovinylation, hydroformylation, olefin metathesis, hydrocarboxylation, isomerization, cyclopropanation, Diels-Alder reaction, Heck reaction, isomerization, Aldol reaction, Michael addition, epoxidation, kinetic resolution and [m+n] cycloaddition were developed with these chiral ligands systems. Ag- and Cu- catalyzed [3+2] cyclization reactions were discovered. It was also discovered that Ag (I) complexes in combination with chiral ferrocene phosphines were efficient asymmetric catalysts for the [3+2] cyclization reaction.

Representative examples of chiral phosphine ligands having a ferrocene anchor are depicted below:

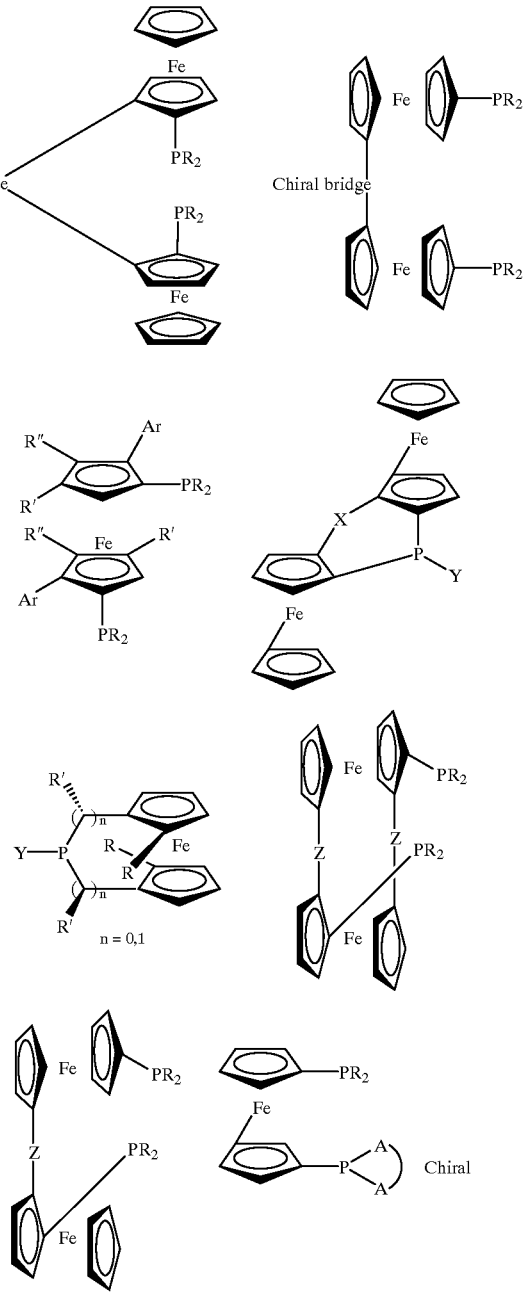

Ferrocene anchors are useful for constructing chiral phosphine ligands. Some of these chiral phosphines have been used in commercial applications of asymmetric catalysts. Lack of systematic studies of ferrocene phosphine ligands limits the applications of these ligands. Structurally innovative new chiral ferrocene phosphines are disclosed in this invention. Many examples of these ligands are provided to demonstrate the scope of the invention. For example, Pd-catalyzed allylic alkylation and kinetic resolution have been achieved using these ferrocene chiral phosphines.

Several of these chiral ferrocene phosphine ligands are used for a variety of asymmetric catalytic reactions, including Cu and Ag-catalyzed [3+2] cyclization of azomethine ylides.

In a preferred embodiment, the ligand of the present invention includes compounds represented by the formulas:

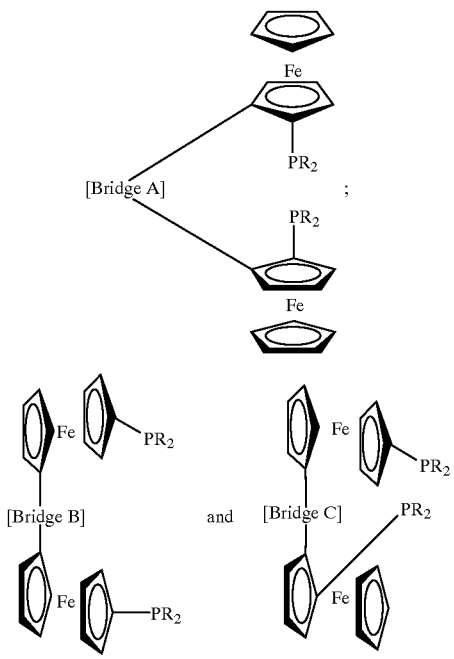

wherein "bridge A" can be a group, such as, —CONH—R*—NHCO—, —CO—OR*O—CO—, —CO—R*—CO—, —CH=N—R*—N=CH—, —CH$_2$NH—R*—NHCH$_2$—, —CH$_2$NHCO—R*—CONHCH$_2$—, —C*H(R$^1$)NH—R*—NHC*H(R$^1$)—, —C*H(R$^1$)NHCO—R*—CONHC*H(R$^1$)—, —CONH—R—NHCO—, —CO—ORO—CO—, —CO—R—CO—, —CH=N—R—N=CH—, —CH$_2$NH—R—NHCH$_2$—, —CH$_2$NHCO—R—CONHCH$_2$—, —C*H(R$^1$)NH—RNH—C*H(R$^1$)—, —C*H(R$^1$)NHCO—R—CONHC*H(R$^1$)—, C=O, C=S, SO$_2$, —PO(OR$^1$)—, —PO(NHR$^1$)—, —PO(NR$^1{}_2$)—, Si(R$^1$)$_2$—, —R—*, or —R—;

wherein "bridge B" has a stereogenic carbon center; "bridge B" can be a group, such as, —CONH—R*—NHCO—, —CO—OR*O—CO—, —COR*—CO—, —CH=N—R*—N=CH—, —CH$_2$NH—R*—NHCH$_2$—, —CH$_2$NHCO—R*—CONHCH$_2$—, —C*H(R$^1$)NH—R*—NHC*H(R$^1$)—, —C*H(R$^1$)NHCO—R*—CONHC*H(R$^1$)—, —C*H(R$^1$)NH—RNH—C*H(R$^1$)—, —C*H(R$^1$)NHCO—R—CONHC*H(R$^1$)—, or —R—*;

wherein "bridge C" can be a group, such as, CO, SO$_2$, CH=CH, —CONHR*NHCO— or —(CH$_2$)n— wherein n is 0, 1 or 2; and wherein R$^1$ can be a group, such as, an alkyl, aryl, aralkyl, alkaryl, or a substituted derivative thereof; —R— can be an alkylene, arylene or a substituted derivative thereof; and * indicates the presence of a stereogenic carbon center.

Preferably, R$^1$ is an alkyl, aryl, aralkyl or alkaryl of 1 to 22 carbon atoms, and each R$^1$ optionally has one or more substituents, each independently selected from halogen, ester, ketone, carboxylic acid, hydroxy, alkoxy, aryloxy, thiol, alkylthio and dialkylamino.

Preferably, —R— can be —(CH$_2$)$_n$— where n is an integer in the range of from 1 to 8, 1,2-divalent phenyl, 2,2'-divalent-1,1'-biphenyl, 2,2'-divalent-1,1'-binaphthyl or ferrocene, and wherein each —R— optionally has one or more substituents, each independently selected from aryl, alkyl, halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine.

The ligands of the present invention can be a racemic mixture of enantiomers. Preferably, the ligand is a non-racemic mixture of enantiomers, and more preferably, the ligand is one of the enantiomers. Preferably, the ligand has an optical purity of at least 85% ee, and more preferably, the ligand has an optical purity of at least 95% ee.

Preferably, the ligand is selected from compounds represented by the formulas:

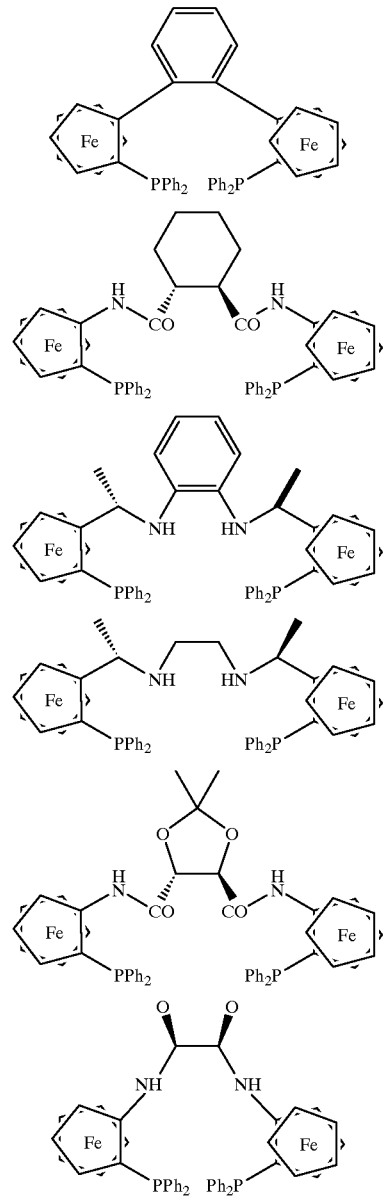

-continued
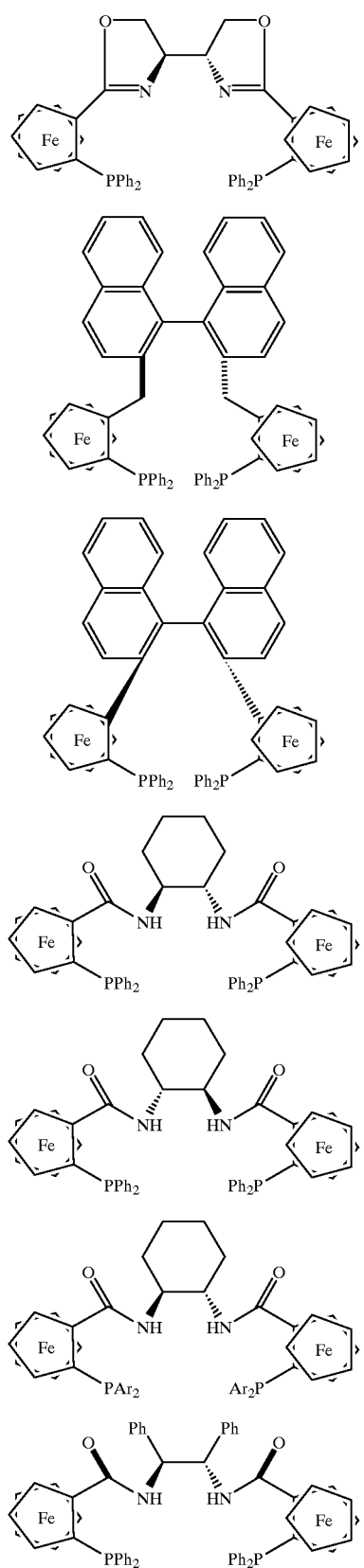
-continued
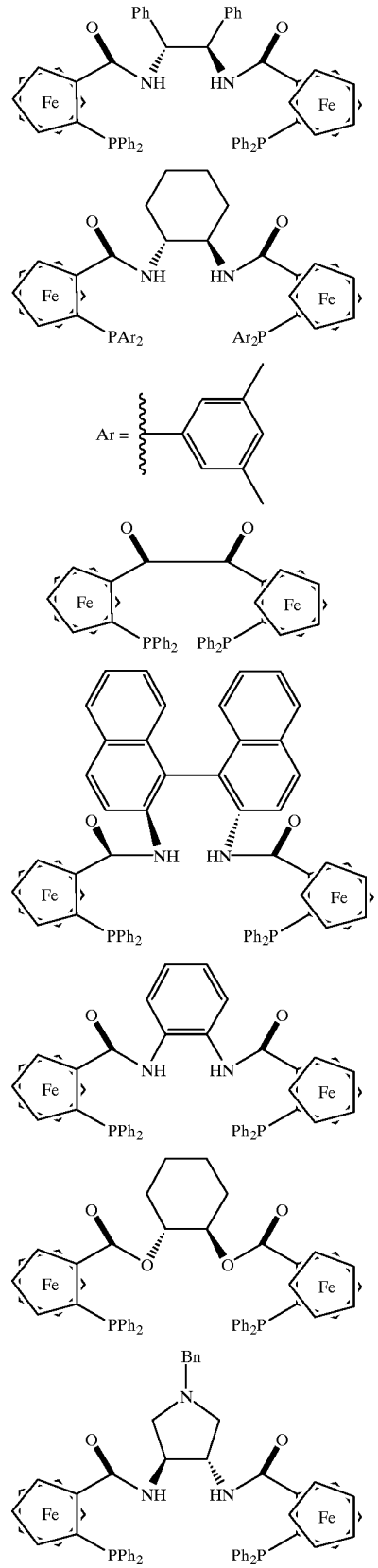

-continued
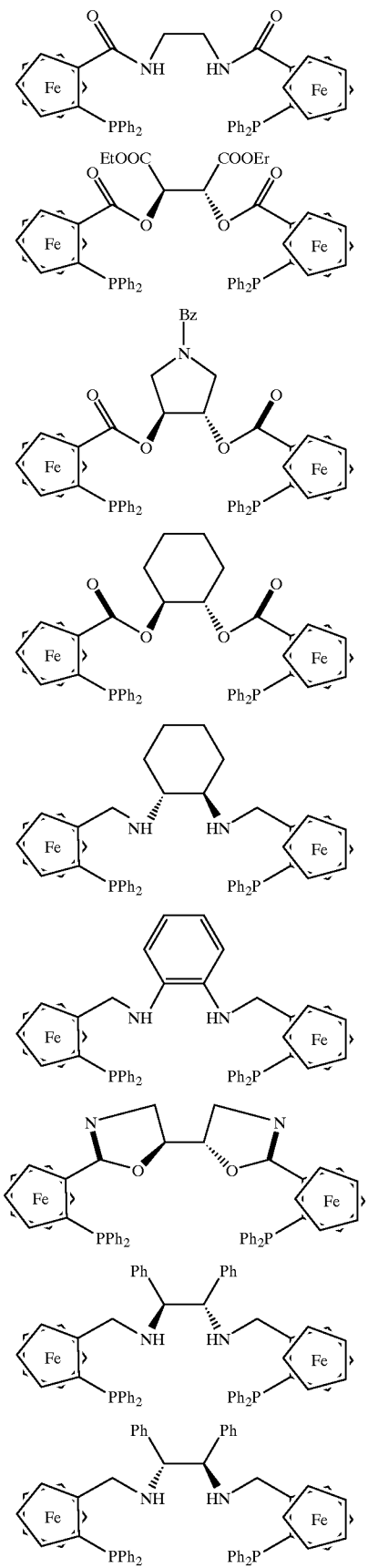
-continued
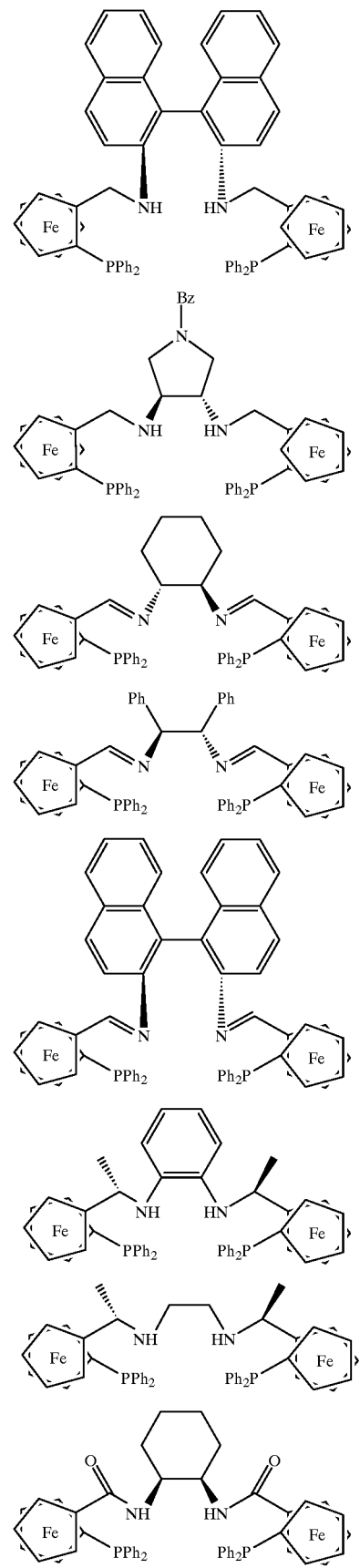

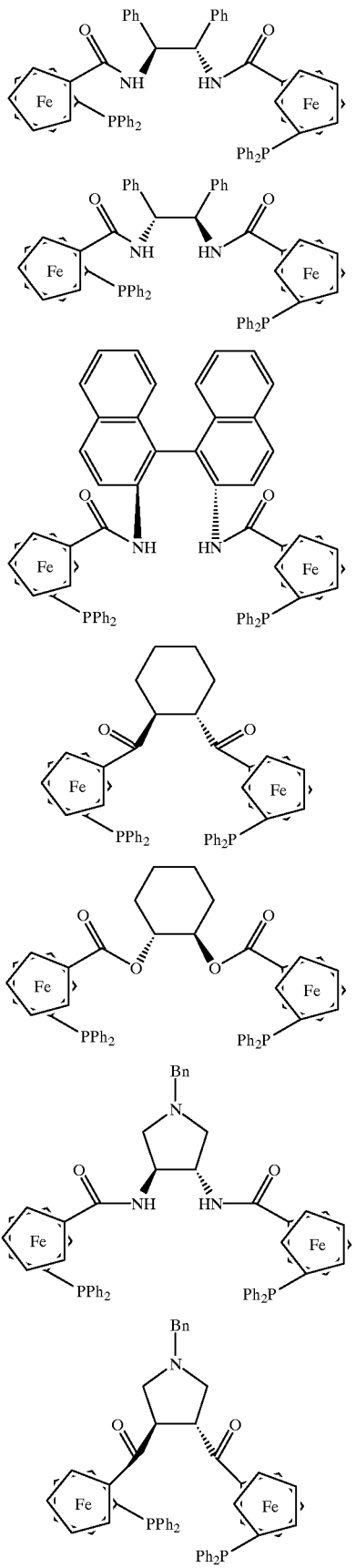

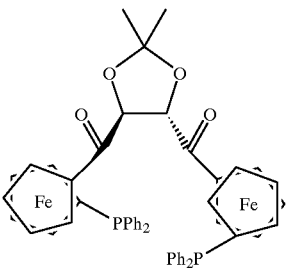

In another preferred embodiment, the ligand of the present invention includes compounds represented by the formulas:

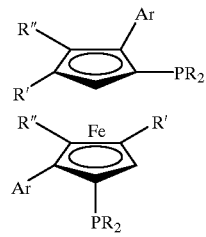

wherein R is an alkyl, aryl, substituted alkyl, substituted aryl; Ar is a susbtituted or unsubstituted aryl group; wherein Ar and R" together form an extended arene; wherein each R' and R" is independently selected from H, alkyl, aryl substituted alkyl, substituted aryl, ester and alkoxy; and wherein R'—R" together form a cyclic alkyl or a extented arene.

In still another preferred embodiment, the ligand of the present invention includes compounds represented by the formulas:

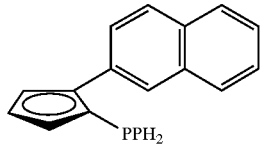

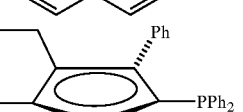 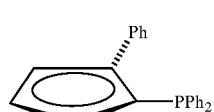

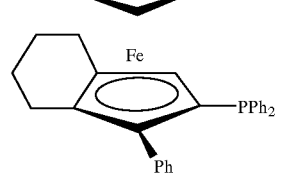 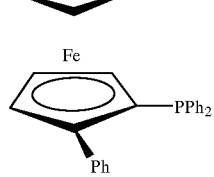

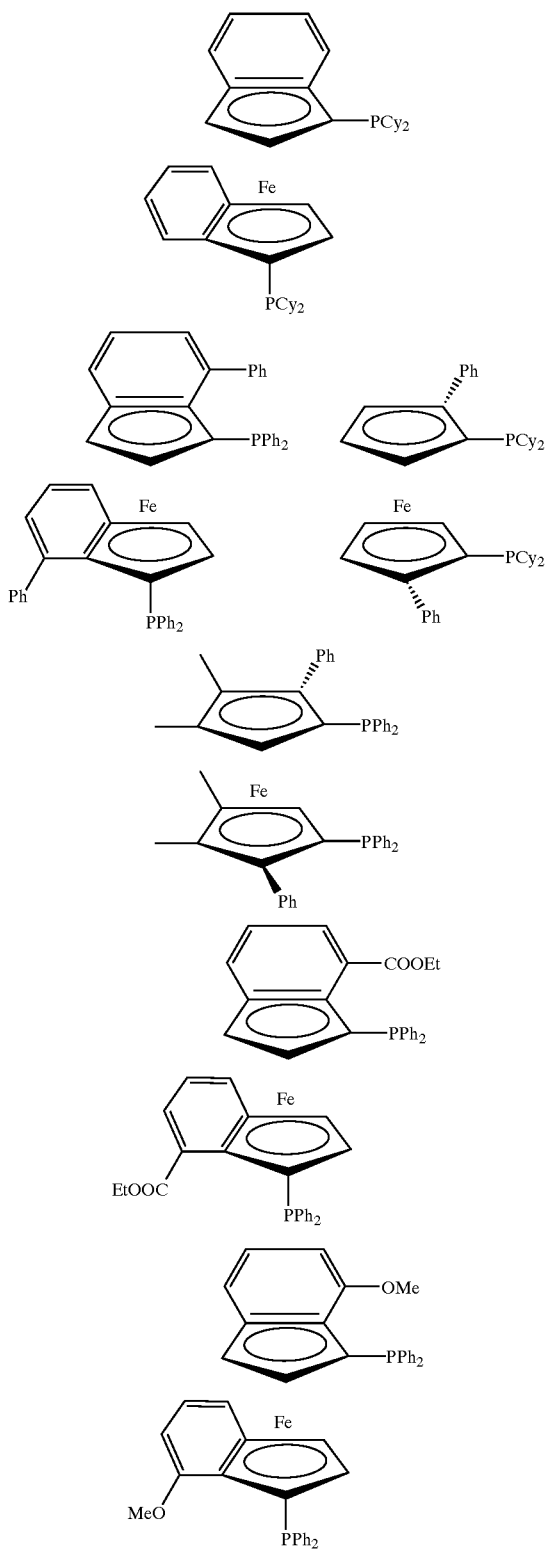

In yet another preferred embodiment, the ligand of the present invention includes compounds represented by the formulas:

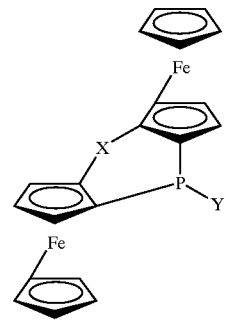

wherein X can be CO, SO$_2$, (CH$_2$)n wherein n=0, 1 or 2, or CH=CH;

wherein Y can be an alkyl, aryl, substituted alkyl, substituted aryl or a group represented by the formula:

—(linker)—W wherein W is represented by the formula:

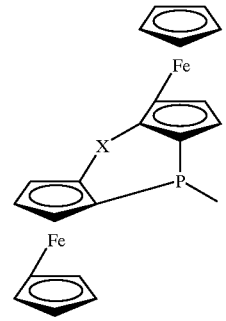

wherein X has the same meaning as above; and wherein the "linker" can be —(CH$_2$)$_n$— where n is an integer in the range of from 1 to 8, 1,2-divalent phenyl, 2,2'-divalent-1,1'-biphenyl, 2,2'-divalent-1,1'-binaphthyl or ferrocene, and wherein each "linker" optionally has one or more substituents, each independently selected from aryl, alkyl, halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine.

The preferred ligands of this embodiment include compounds represented by the formulas:

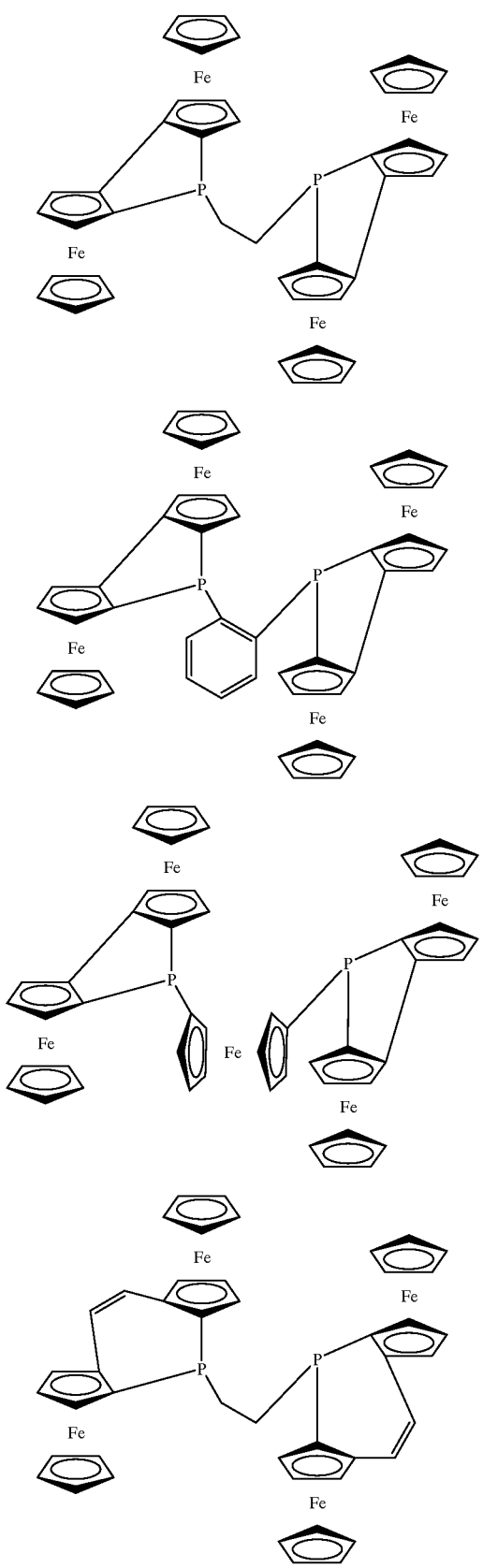

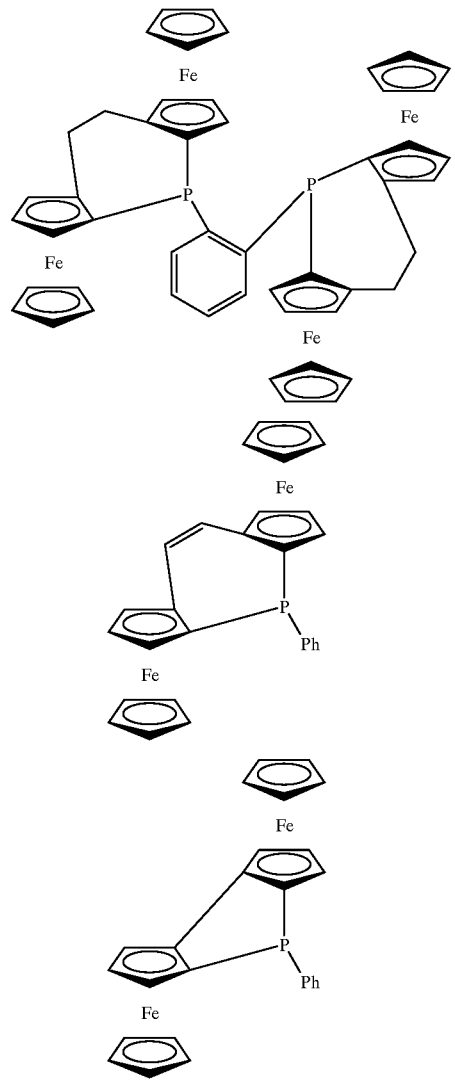

In another preferred embodiment, the ligand of the present invention includes compounds represented by the formulas:

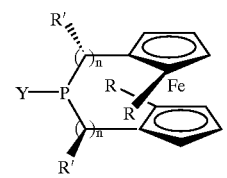

n = 0,1 wherein R can be H, alkyl, aryl, substituted alkyl, substituted aryl, silyl, ester, amide, oxazoline or phosphate, with the proviso that R is H when R' is not H; R' can be H, alkyl, aryl, substituted alkyl or substituted aryl; n is 0 or 1;

Y can be alkyl, aryl, substituted alkyl, substituted aryl or a group represented by the formula:

—(linker)—W wherein W is represented by the formula:

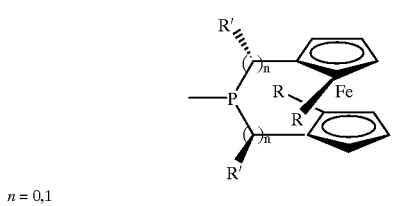

$n = 0, 1$ wherein the "linker" can be $-(CH_2)_n-$ where n is an integer in the range of from 1 to 8, 1,2-divalent phenyl, 2,2'-divalent-1,1'-biphenyl, 2,2'-divalent-1,1'-binaphthyl or ferrocene, and wherein each "linker" optionally has one or more substituents, each independently selected from aryl, alkyl, halogen, ester, ketone, sulfonate, phosphonate, hydroxy, alkoxy, aryloxy, thiol, alkylthiol, nitro, amino, vinyl, substituted vinyl, carboxylic acid, sulfonic acid or phosphine.

The preferred ligands of this embodiment include compounds represented by the formulas:

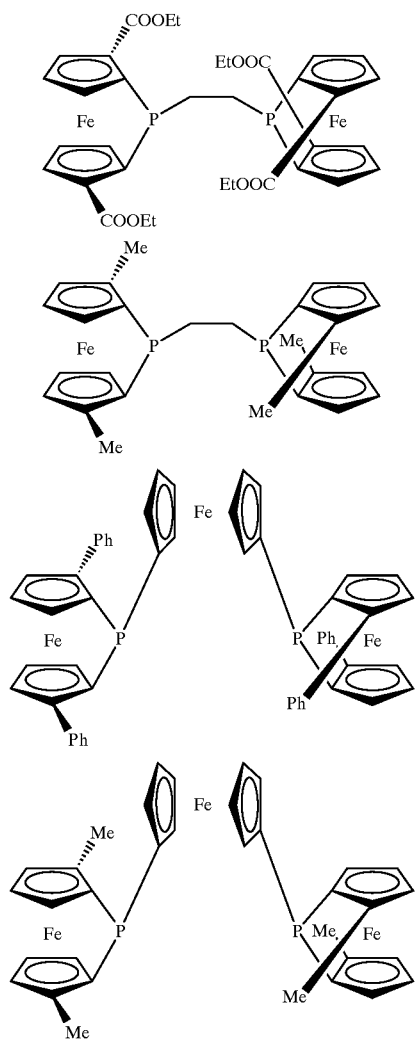

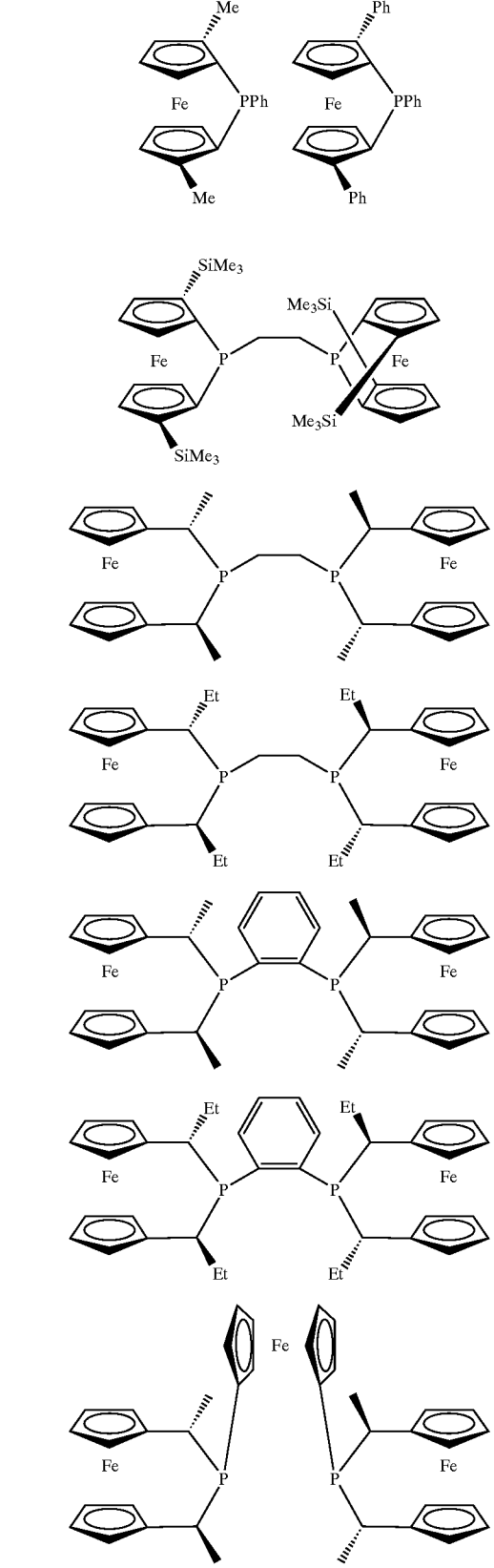

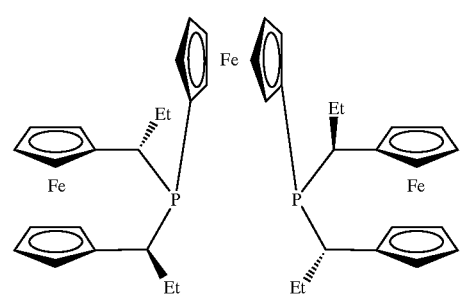
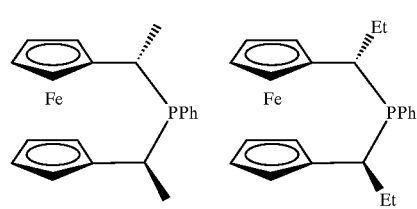
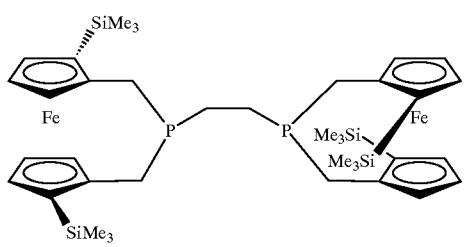
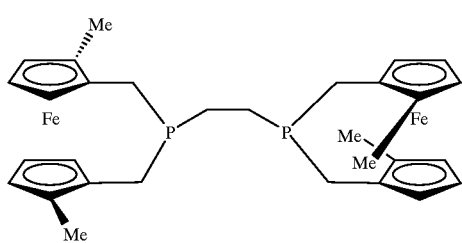
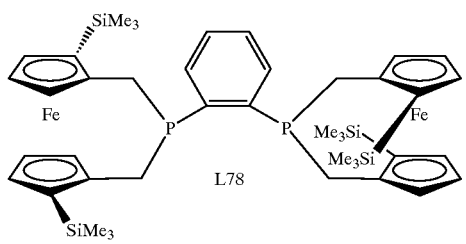
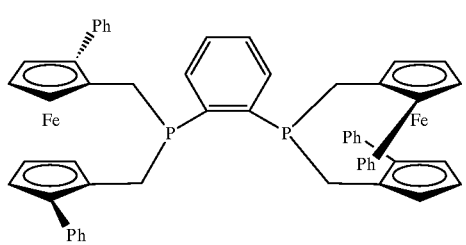
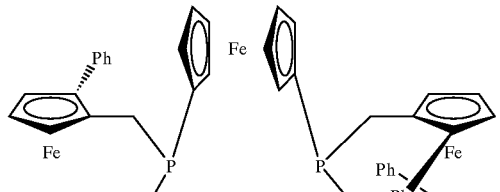
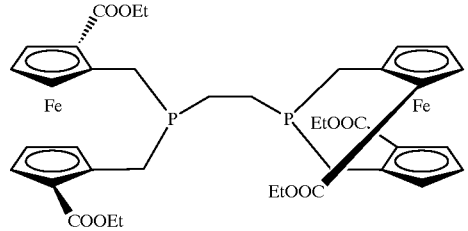
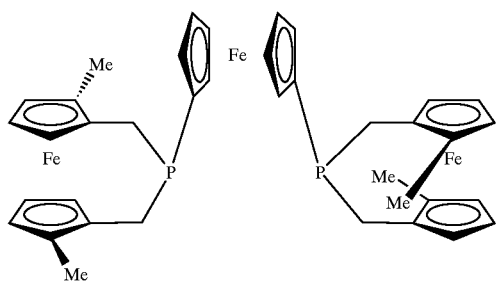
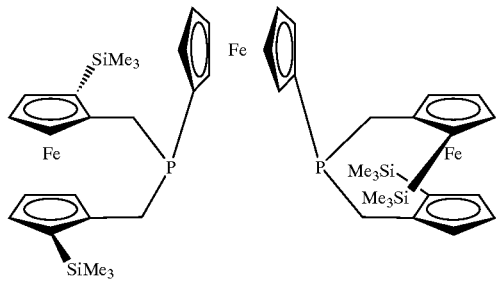
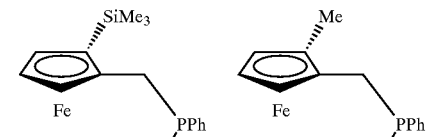
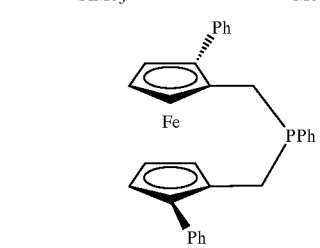
In still another preferred embodiment, the ligand of the present invention includes compounds represented by the formulas:

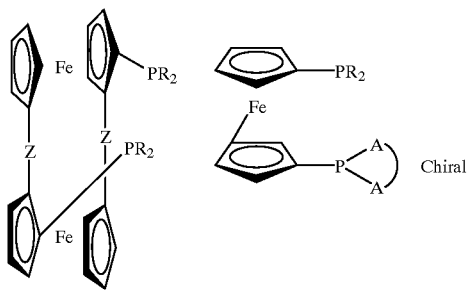

wherein R can be alkyl, aryl, substituted alkyl or substituted aryl; Z can be CO, $SO_2$ and —$(CH_2)_n$— wherein n=0, 1 or 2; each A is independently a group containing an $sp^2$ or $sp^3$ hybridized N, O, C or S atom, wherein two A groups form a cyclic compound via a chiral connecting group which can be —NHR*NH—, —OR*O—, —SR*S—, —Binol— or —$CH_2$R*$CH_2$—; wherein each R* is a chiral alkyl or aryl group.

Preferably, the R* group is 1,2-divalent phenyl and 2,2'-divalent-1,1'binaphthyl.

The preferred ligands of this embodiment include compounds represented by the formulas:

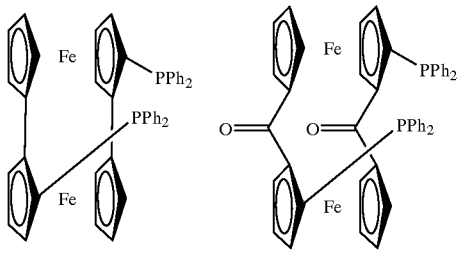

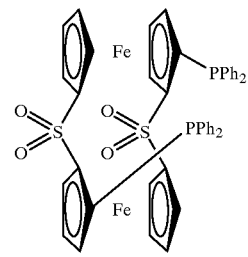

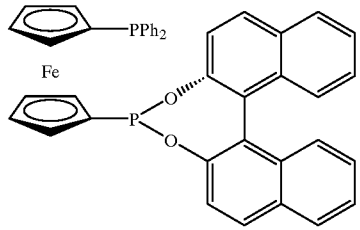

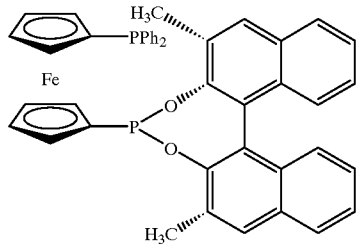

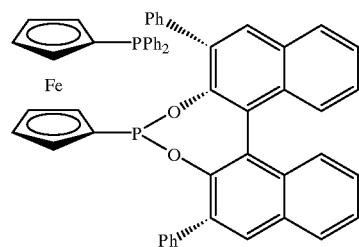

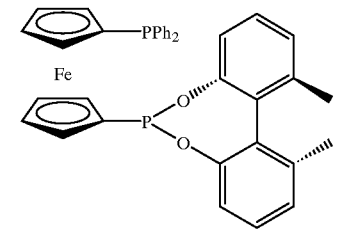

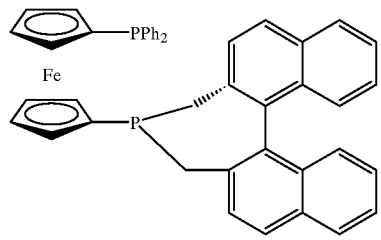

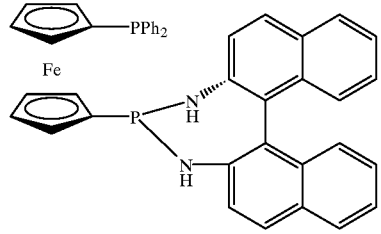

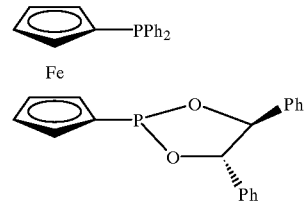

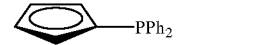

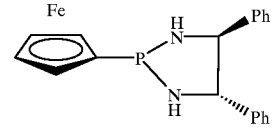

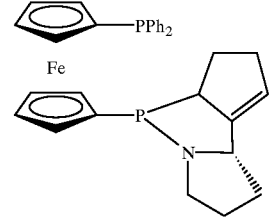

-continued

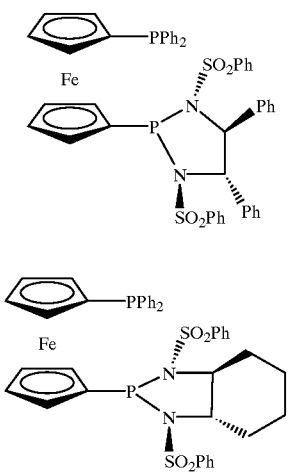

The design and synthesis of new chiral ligands remains an important area of research with respect to developing highly enantioselective transition metal catalyzed reactions. A successful ligand should therefore be readily accessible, stable, and highly tunable since modification of the ligands steric and electronic properties are often necessary for achieving high asymmetric induction Ligand families derived from effective chiral synthons with the aim of meeting the above-mentioned requirements.

One synthon of chiral ferrocene phosphines is made in this invention and it is derived from the well-known chiral phosphinoferrocenyloxazoline [Richards, C. J.; Damalidis, T.; Hibbs, D. E.; Hursthouse, M. B. *Synlett* 1995, 74, Nishibayashi, Y.; Uemara, S. *Synlett* 1995, 79]. The phosphine acid with a chiral ferrocene backbone, i.e., chiral carboxyferrocenyl diaryl phosphine, can be prepared in large quantities and it is an air-stable solid.

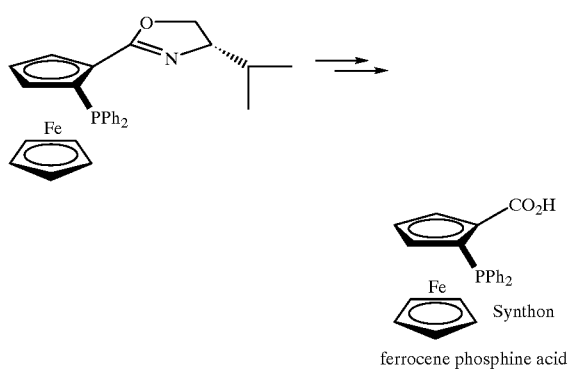

ferrocene phosphine acid

Ligand modifications can then be easily realized by appending various units to the carboxylate functionality. This can be achieved most directly by coupling the ferrocene acid with a variety of amines (chiral or achiral), alcohols (chiral or achiral) using reliable straightforward chemistry. Furthermore, the planar chirality of ferrocene, usually in conjunction with additional sources of chirality, has proven to be quite an effective framework for providing high asymmetric induction.

While the (S) carboxylferrocenyl diaryl phosphine shown above can be made from oxazolinoferrocenyl derived from (S)-vanlinol, the corresponding (R) carboxylferrocenyl diaryl phosphine can be prepared from oxazolinoferrocenyl derived from (R)-vanlinol.

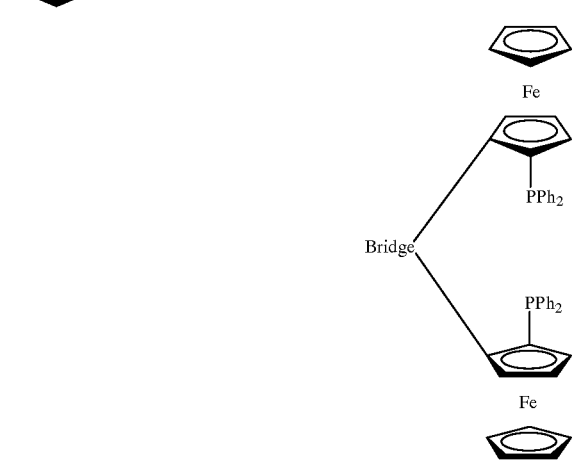

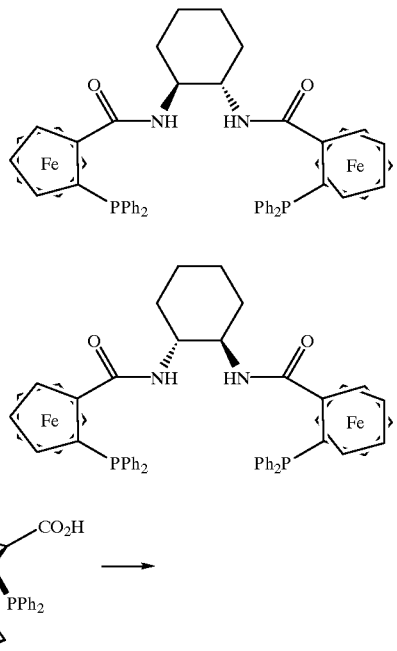

The first ligands discussed are readily obtained by coupling ferrocene phosphine acid with (1S, 2S) and (1R, 2R)-diaminocyclohexane coupling to produce ferrocene amide phosphine (FAP). These ligands are very successful in inducing high asymmetric induction for a variety of substrates in the Pd-catalyzed allylic substitution reaction. The goal for designing these ligands was to discern the effect of planar chirality in conjunction with the chirality of the diaminocyclohexane backbone. More importantly, since the ligand possesses the planar chiral ferrocene unit, achiral backbones can also be used. These ligands are structurally different from Trost ligand (FIG. A) for asymmetric reactions.

Accordingly, the present invention also includes a process for preparing a chiral carboxyferrocenyl diaryl phosphine represented by the formula:

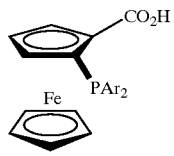

wherein each Ar is independently selected from phenyl and an aryl of 6 to 22 carbon atoms. The process comprises the steps of:

providing a chiral oxazolinoferrocenyl diaryl phosphine derived from (S)-vanlinol;

sequentially contacting the chiral oxazolinoferrocenyl diaryl phosphine phosphine derived from (S)-vanlinol and:

(1) water and anhydrous sodium sulfate;

(2) trifluoroacetic acid; and (3) an acylating agent;

to produce an N-acylated (S)-vanlinol ester of carboxyferrocenyl diaryl phosphine; and contacting the N-acylated (S)-vanlinol ester of carboxyferrocenyl diaryl phosphine, potassium tertiary butoxide and water to produce the chiral carboxyferrocenyl diaryl phosphine.

Preferably, (S)-oxazolinoferrocenyl diaryl phosphine derived from (S)-vanlinol is formed by a process comprising the steps of:

contacting ferrocenyl chloride and (S)-vanlinol in the presence of a base to produce a ferrocene amide;

contacting the ferrocene amide and an alkyl or aryl sulfonyl chloride to produce a ferrocene oxazoline; and contacting the ferrocene oxazoline with an organolithium reagent and thereafter with a diarylhalophosphine to produce said chiral oxazolinoferrocenyl diaryl phosphine.

Preferably, the diarylhalophosphine is $PPh_2Cl$, $P(xylyl)_2Cl$ or $P(ph)(xylyl)Cl$ and the acylating agent is acetic anhydride.

The present invention still further includes a process for:

(1) preparing (S, S, S, S)-FAP 6 ligand, which comprises the step of contacting a carboxyferrocenyl diaryl phosphine and (1S, 2S)-diaminocyclohexane under reaction conditions sufficient to produce said (S, S, S, S)-FAP 6 ligand; and (2) preparing (S, R, R, S)-FAP 7 ligand comprising the step of contacting a carboxyferrocenyl diaryl phosphine and (1R, 2R)-diaminocyclohexane under reaction conditions sufficient to produce said (S, R, R, S)-FAP 7 ligand.

The FAP 6 or FAP 7 ligands prepared by the above processes have an optical purity of at least 85% ee, preferably at least 95% ee.

The present invention also includes a catalyst prepared by a process comprising contacting a transition metal salt, or a complex thereof, and a ligand according to the present invention. The catalyst may be prepared in situ or as an isolated compound.

The catalyst of the present invention can be a racemic mixture of enantiomers. Preferably, the catalyst is a non-racemic mixture of enantiomers, and more preferably, the catalyst is one of the enantiomers. Preferably, the catalyst has an optical purity of at least 85% ee, and more preferably, the catalyst has an optical purity of at least 95% ee.

Suitable transition metals for the preparation of the catalyst include Ag, Pt, Pd, Rh, Ru, Ir, Cu, Ni, Mo, Ti, V, Re and Mn.

As mentioned above, the catalyst can be prepared by contacting a transition metal salt or its complex and a ligand according to the present invention.

Suitable transition metal salts or complexes include the following:

$AgX$; $Ag(OTf)$; $Ag(OTf)_2$; $AgOAc$; $PtCl_2$; $H_2PtCl_4$; $Pd_2(DBA)_3$; $Pd(OAc)_2$; $PdCl_2(RCN)_2$; $(Pd(allyl)Cl)_2$; $Pd(PR_3)_4$; $(Rh(NBD)_2)X$; $(Rh\ (NBD)Cl)_2$; $(Rh(COD)Cl)_2$; $(Rh(COD)_2)X$; $Rh(acac)(CO)_2$; $Rh(ethylene)_2(acac)$; $(Rh(ethylene)_2Cl)_2$; $RhCl(PPh_3)_3$; $Rh(CO)_2Cl_2$; $RuHX(L)_2$ (diphosphine), $RuX_2(L)_2$ (diphosphine), $Ru(arene)X_2$ (diphosphine), $Ru(aryl\ group)X_2$; $Ru(RCOO)_2$ (diphosphine); $Ru(methallyl)_2(diphosphine)$; $Ru(aryl\ group)X_2(PPh_3)_3$; $Ru(COD)(COT)$; $Ru(COD)(COT)X$; $RuX_2$ (cymen); $Ru(COD)n$; $Ru(aryl\ group)X_2(diphosphine)$; $RuCl_2(COD)$; $(Ru(COD)_2)X$; $RuX_2(diphosphine)$; $RuCl_2(=CHR)(PR'_3)_2$; $Ru(ArH)Cl_2$; $Ru(COD)(methallyl)_2$; $(Ir(NBD)_2Cl)_2$; $(Ir(NBD)_2)X$; $(Ir(COD)_2Cl)_2$; $(Ir(COD)_2)X$; $CuX\ (NCCH_3)_4$; $Cu(OTf)$; $Cu(OTf)_2$; $Cu(Ar)X$; $CuX$; $Ni(acac)_2$; $NiX_2$; $(Ni(allyl)X)_2$; $Ni(COD)_2$; $MoO_2(acac)_2$; $Ti(OiPr)_4$; $VO(acac)_2$; $MeReO_3$; $MnX_2$ and $Mn(acac)_2$; wherein each R and R' is independently selected from alkyl or aryl; Ar is an aryl group; and X is a counteranion.

In the above transition metal salts and complexes, L is a solvent and the counteranion X can be halogen, $BF_4$, $B(Ar)_4$ wherein Ar is fluorophenyl or 3,5-di-trifluoromethyl-1-phenyl, $ClO_4$, $SbF_6$, $PF_6$, $CF_3SO_3$, RCOO or a mixture thereof.

In another aspect, the present invention includes a process for preparation of an asymmetric compound using the catalysts described above. The process includes the step of contacting a substrate capable of forming an asymmetric product by an asymmetric reaction and a catalyst according to the present invention prepared by contacting a transition metal salt, or a complex thereof, and a ligand according to the present invention.

Suitable asymmetric reactions include asymmetric hydrogenation, hydride transfer, allylic alkylation, hydrosilylation, hydroboration, hydrovinylation, hydroformylation, olefin metathesis, hydrocarboxylation, isomerization, cyclopropanation, Diels-Alder reaction, Heck reaction, isomerization, Aldol reaction, Michael addition; epoxidation, kinetic resolution and [m+n] cycloaddition wherein m=3 to 6 and n=2.

Preferably, the asymmetric reaction is hydrogenation and the substrate to be hydrogenated is an ethylenically unsaturated compound, imine, ketone, enamine, enamide, and vinyl ester. Suitable catalysts for the hydrogenation of ketones to produce a chiral alcohol include chiral ruthenium complex with a PNNP ferrocene ligand according to the present invention. Suitable catalysts for the silver-catalyzed asymmetric [3+2] cycloaddition of, for example, an azomethine ylide with a dipolarophile, is the Ag-Xyl-FAP catalyst, which can be prepared from AgOAc or Xyl-FAP ligand.

Preferably, the asymmetric reaction is allylic alkylation and the substrate is an allylic ester. Also preferably, the asymmetric reaction is a kinetic resolution reaction and the substrate is a racemic allylic ester.

The Pd-catalyzed allylic alkylation reaction has become the standard test reaction for gauging the effectiveness of new ligands [Pfaltz, A.; Lautens, M., in *Comprehensive Asymmetric Catalysis*; Jacobsen, E. N.; Pfaltz, A.; Yamamoto, H., Eds.; Springer-Verlag: Berlin, 1999, Vol. III, Chapter 24, pp. 833–884].

A preferred catalyst for the asymmetric allylic alkylation of an allylic ester substrate is ferrocene amide phosphine (FAP), which is a palladium catalyst according to the present invention. This ligand has been very successful in inducing high asymmetric induction for a variety of substrates in the Pd-catalyzed allylic substitution reactions.

Allylic alkylation of an allylic ester substrate under kinetic resolution conditions, i.e., allylic alkylation of a racemic mixture of an allylic ester substrate with a non-racemic palladium catalyst according to the present invention, only a single enantiomer is preferentially allylically alkylated. This reaction produces not only an enantiomerically enriched allylically alkylated product, but also an enantiomerically enriched unreacted allylic ester.

Specifically, (E)-1,3-diphenylprop-2-enyl acetate has been the substrate most often used and numerous ligands have been successfully applied to the enantioselective alkylation of this compound. With more challenging cycloalkenyl ester substrates, far fewer successful ligands have been reported. Employing FAP ligands, high enantioselectivities can be achieved for both (E)-1,3-diphenylprop-2-enyl acetate and cycloalkenyl ester.

Using dimethyl malonate as nucleophile and a chiral FAP ligand, the reaction conditions were optimized (see Table 1, below). Several of the commonly used bases for allylic alkylation were investigated with the combination of BSA and KOAc proving most effective. Further improvement of enantioselectivity was achieved when the reaction was carried out in THF. The reaction seemed to proceed quickly to product within the first few hours then slowed significantly or ceased altogether. This observation also coincided with formation of a precipitate from the reaction solution.

A very efficient kinetic resolution of cycloalkenyl ester is occurring with a Pd-FAP catalyst (table 2). For example, after 54% conversion, unreacted allylic acetate has an enantiomeric excess of 99% and the alkylation product has an enantiomeric excess of 92%. Using the reported equation for measuring kinetic resolution efficiency this gives S=61. An additional 20 hours of reaction time results only in a further 20% reaction conversion.

In tables 3–4, the reactivity and enantioselectivity increase as the size of the alkali metal increases, reaching a maximum with Cs$^+$. Alkylation of the "standard" (E)-1,3-diphenylprop-2-enyl ethyl carbonate proceeded with a high enantioselectivity of 93% using one FAP ligand. It is interesting to note that a mismatched FAP gave only a slightly lower enantioselectivity of 87%.

Azomethine ylide 1,3-dipoles react with olefinic dipolarophiles possessing electron withdrawing groups to form highly substituted five-membered ring nitrogen heterocycles [Grigg, R.; Hargreves, S.; Redpath, J.; Turchi, S.; Yogananthan, G. *Synthesis* 1999, 441]. This extremely versatile and atom economical process has been used towards construction of highly functionalized synthetic intermediates and as a key step in alkaloid natural product syntheses. A practical approach has been formation of N-metallated azomethine ylides [Kanemasa, S.; Tsuge, O. In *Advances in Cycloaddition;* Curran, D. P., Ed.; Jai Press: Greenwich, 1993; Vol. 3, pp 99–159]. This method allows the cycloaddition to proceed under much milder reaction conditions and in many cases with a high degree of stereocontrol.

In many cases a stoichiometric quantity of Ag(I) salt is employed. Due to the low solubility of most Ag(I) salts, polar coordinating solvents such as $CH_3CN$, DMSO, and DMF are typically used. The reaction is thought to proceed by N, O-coordination of the α-aminoester imine to the transition metal, followed by deprotonation with $NEt_3$ to form the reactive metal-bound azomethine ylide dipole. Coordination of the imine with the metal increases the acidity of the α-hydrogen thus allowing deprotonation by a weak base such as $NEt_3$.

Development of an asymmetric azomethine ylide cycloaddition is important if this methodology is to be truly practical for the synthesis of biologically active compounds. The attractive feature of this process is the simultaneous formation of up to four contiguous chiral centers in one synthetic transformation with a high level of diastereoselectivity.

The present invention includes AgOAc and $PPh_3$ as the catalyst system employed for making the [3+2] products. Prior to the present invention, there had been no reported attempts to study the effect of ligation on the Ag catalyst. Ligation is important because Ag(I) salts have very low solubility in most organic solvents. In order to effectively promote this reaction, Ag(I) salts have been typically used in stoichiometric quantities. However, addition of $PPh_3$ forms a soluble complex with Ag(I) salts in most organic solvents. As a result, the cycloaddition reaction proceeds efficiently with only 1 mol % of catalyst.

All of the racemic pyrrolidine products in the present invention were formed using $AgOAc/PPh_3$ as catalyst. This proved to be a highly reactive and general catalyst system for a variety of azomethine ylide and dipolarophile substrates. In some cases, the products were formed within minutes. This invention disclosed that Cu(I) catalysts, such as CuOAc and $Cu(CH_3CN)_4BF_4$, complexed with $PPh_3$ were equally as effective. Prior to this study, there were no reports of any catalysts used in such transformation.

In tables 5–9, a number of experiments have been carried out. Some commercially available chiral phosphines were tested. However, the resulting enantioselectivities were very low.

The present invention includes new chiral ferrocene amide phosphines with planar chirality. The Ag complexes with these ligands are effective catalysts for the [3+2] cycloadditions. A variety of dipolarophile substrates and dipole substrates have been tested. The preferred ligand for this reaction is a Xyl-FAP ligand.

EXAMPLE 1

General Experimental Procedure

All reactions and manipulations were performed in a nitrogen-filled glovebox or using standard Schlenk techniques. All reagents were obtained from Aldrich or Strem and used directly. Toluene, tetrahydrofuran (THF) and hexanes were distilled from sodium benzophenone ketyl under nitrogen. Methylene chloride ($CH_2Cl_2$) was distilled from $CaH_2$. Methanol ($CH_3OH$) was distilled from Mg under nitrogen. Gas chromatography was carried out on Helwett-Packard 6890 gas chromatographs using a Chiral Select 1000 column (Dimensions: 15 m×0.25 mm), carrier gas: He (1 mL/min$^{-1}$). HPLC analysis was carried out on a Waters™ 600 chromatograph with an (S, S)-Whelk-01 column from Regis Technologies, Inc. {particle size: 5.0 μm column dimensions: 25 cm (length)×0.46 cm (i.d.)}. $^1$H, $^{13}$C and $^{31}$P NMR were recorded on Bruker WM 360 spectrometers. Chemical shifts were reported in ppm downfield from tetramethylsilane with the solvent resonance as the internal stand or 85% $H_3PO_4$ as the external standard respectively. Optical rotation was obtained on a Perkin Elmer 241 polarimeter.

EXAMPLE 2

Synthesis of Chiral FAP (Ferrocene Amide Phosphine) ligands:

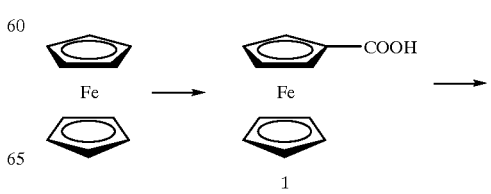

1

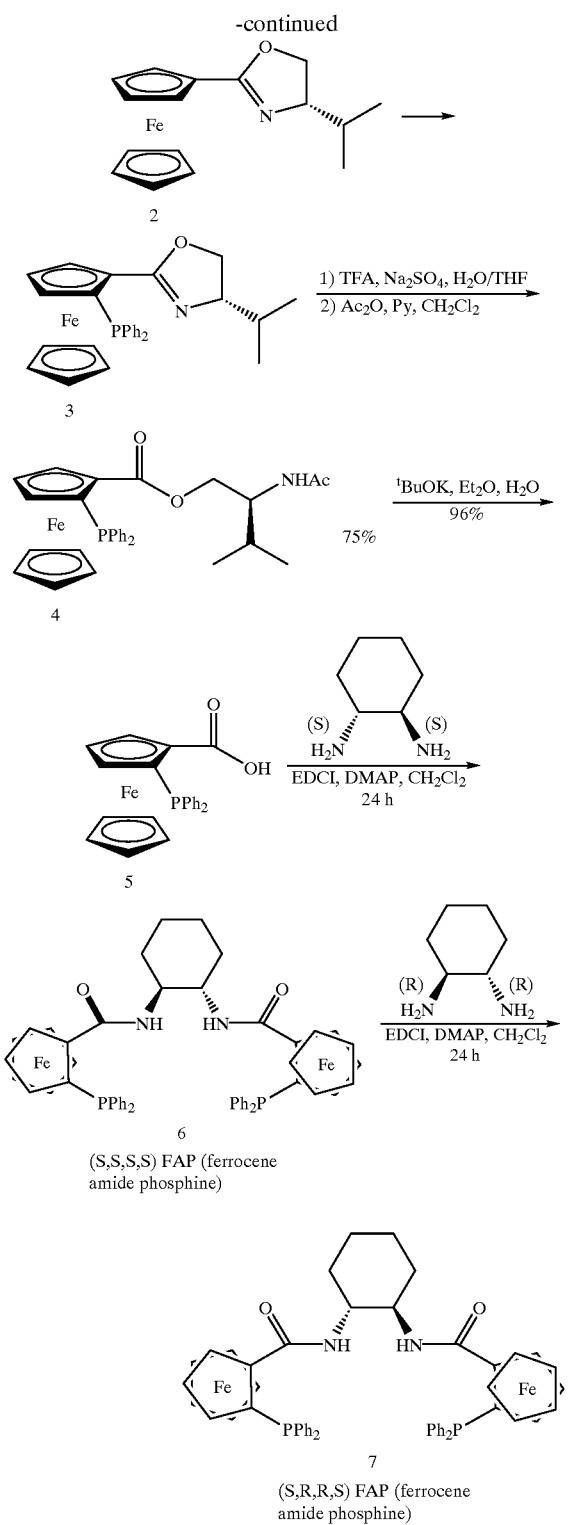

Synthesis of Ferrocene Carboboxylic Acid 1

A thoroughly dried, 2-L three-necked, round-bottomed flask was equipped with a mechanical stirrer, a funnel for the addition of air-sensitive solid, and a two-necked adapter holding a thermometer and a gas-inlet tube. The flask is charged with 74.4 g (0.4 mol) of ferrocene, 53.4 mL (0.4 mol) of 2-chlorobenzoyl chloride and 600 mL of $CH_2Cl_2$, and the addition funnel contains 56 g (0.42 mol) of $AlCl_3$. The mixture was stirred in an ice bath and $AlCl_3$ was added in small potions at such a rate that the reaction mixture remained below 5° C. This addition took about 20 min. and the mixture was stirred for 30 min. in the ice bath and was stirred for 2 h at rt. The reaction mixture was cooled in an ice bath and 400 ml of water was added. The mixture was loaded to a separatory funnel, the organic layer was separated, and aqueous layer was extracted with 400 mL of $CH_2Cl_2$. The combined $CH_2Cl_2$ solution are washed with 100 mL of water, 100 mL of 10% NaOH, 100 mL of brine and dried with $Na_2SO_4$. After filtration, the solution was evaporated to dryness at reduced pressure to give 129.2 g (>99%) of (2-chlorobenzoyl) ferrocene as a dark red solid.

In a dry 2-L flask equipped with a mechanical stirrer and a reflux condenser topped with a nitrogen-inlet tube was charged with 1L of DME and 193 g (1.6 mol) of KOtBu. Under N2 atmosphere, 8.8 mL (0.48 mol) of water was added to the crude (2-chlorobenzoyl) ferrocene to give a red solution. The red solution was stirred and refluxed under $N_2$. As the reaction proceeded with fade of color to tan. The reaction mixture was cooled and poured into 2 L of water. The resulting solution was washed with 2×400 mL of $Et_2O$. The combine organic layer was extracted with 2×200 ml of 10% NaOH. The aqueous phase are then combined and acidified with concentrated HCl. The precipitate was collected by filtration and was dried in are to give yellow power 1 (76 g, 82.6%).

Synthesis of Ferrocene Oxazoline 2

To a suspension of ferrocenecarboxylic acid 1 (52 g, 226 mmol) in $CH_2Cl_2$ (500 ml) at rt under $N_2$ was added oxalyl chloride (40 mL, 458 mmol). A dark red homogeneous solution was formed after 20 min. The reaction mixture was stirred for an additional 20 min, followed by removal of the solvent in vacuo. The resulting crude ferrocenyl chloride was isolated as a dark oil (or crystals on standing). This intermediate was dissolved in $CH_2Cl_2$ (200 ml) and was added a solution of (S)-vanlinol (27.7 g, 269 mmol) and $Et_3N$ (63 mL) in $CH_2Cl_2$ (200 mL) at 0° C. under $N_2$. After stirring the mixture overnight at rt, the dark solution was washed with water (2×300 ml), dried with $Na_2SO_4$, filtered and evaporated in vacuum. The crude product was passed through a short silica gel (3 cm) and was eluted with EtOAc. After evaporation of the solvent, the crude amide (dark oil) was used directly in the next step.

To a solution of the amide (226 mmol) was added $Et_3N$ (63 mL) and $CH_2Cl_2$ (600 mL). To this solution was added dropwise MsCl (21 mL, 271 mmol) in $CH_2Cl_2$ (100 ml) at 0° C. and the solution was stirred at 0° C. for 1 h, followed by stirring at rt. for 6 h. The reaction was quenched by adding 200 mL of water at 0° C. The resulting solution was washed with brine (3×300 ml). The organic layer was dried over $Na_2SO_4$ and the solvent was evaporated in vacuum and chromatographed on a short $Al_2O_3$ column (5 cm) (hexanes/EtOAc=3/1) to give orange solid 2 (55 g, 81.9%).

Synthesis of Phosphine Oxazoline 3

Sec-BuLi (56 ml, 70 mmol) was added at −78° C. under $N_2$ to a solution of ferrocene oxazoline 2 (15.8 g, 53 mmol) and TMEDA (10 mL, 70 mmol) in $Et_2O$ (600 mL). The reaction solution was stirred for 3 h and then the reaction All manipulations were carried out under $N_2$ using standard Schlenk techniques. Solvents were degassed with $N_2$ and dried using standard procedures. Column chromatography was performed using 200–400 mesh silica gel supplied by Natland International Corporation. All other reagents were commercially available and used as received.

was placed in an ice bath and was stirred for 20 min, followed by addition of PPh$_2$Cl (14.4 mL, 80 mmol). The resulting reaction mixture was allowed to warm to rt overnight. The reaction was quenched by adding 200 mL of water and the resulting solution was washed with brine (2×200 mL). The organic layer was dried with Na$_2$SO$_4$ and the solvent was removed in vacuum, loaded on a short silica gel column and eluted with hexanes/EtOAc=5/1 to give orange solid. The crude product was s recrystallized from hexane to give a yellow solid 3 (20.4 g, 79.6%).

Synthesis of an Amide-Ester 4

To a THF (450 mL) solution of 3 (20.4 g, 42.4 mmol) under N$_2$ was added H$_2$O (40.5 mL) and anhydrous Na$_2$SO$_4$ (310 g). After cooling to 0° C., CF$_3$COOH (17.5 mL, 196.5 mmol) was added and the reaction stirred overnight at rt. An additional 90 g of Na$_2$SO$_4$ was added and the reaction mixture was filtered under N$_2$. The Na$_2$SO$_4$ was washed with THF until no color remained and the filtrate was concentrated under reduced pressure affording a yellow solid. This solid was dissolved in CH$_2$Cl$_2$ (700 mL), cooled to 0° C. and Ac$_2$O (75.5 ml, 0.78 mol) was added followed by pyridine (150 mL, 1.86 mol). The reaction mixture was stirred overnight at rt. The resulting red solution was quenched with 3 M HCl (300 ml) and the layers separated. The organic phase was washed with 3 M HCl (2×100 ml), sat. NaHCO$_3$ (100 ml) and dried over Na$_2$SO$_4$. The deep red solution was concentrated under reduced pressure and the crude product purified by passing through a short column of silica gel eluting with EtOAc. The desired product 4 was obtained as a yellow solid (17.1 g, 75% yield). mp =146–147° C.; [α]$_D$=−147.6 (c=0.55, CHCl$_3$); $^1$H NMR (360 MHz, CD$_2$Cl$_2$) δ 0.96 (d, J=6.8 Hz, 3H, CH$_3$), 1.05 (d, J=6.7 Hz, 3H, CH$_3$), 1.71 (s, 3H, CH$_3$), 2.08 (m, 1H, CH); 3.71 (s, 1H), 3.72–3.87 (m, 2H), 4.19 (s, 5H), 4.49–4.52 (m, 2H), 5.15 (s, 1H), 5.32 (br, 1H, NH), 7.16–7.18 (m, 2H), 7.28–7.30 (m, 3H), 7.41–7.51 (m, 5H), $^{13}$C NMR (90 MHz, CD$_2$Cl$_2$) δ 19.5, 19.8, 23.4, 29.7, 53.9, 65.1, 71.4, 72.8, 75.3 (d, J$_{P-C}$=1.5 Hz), 75.9–76.1 (m, 2C), 78.1 (d, J$_{P-C}$=15.0 Hz), 128.5–140.4 (8 different aromatic C's), 169.5, 171.6 (d, J$_{P-C}$=2.6 Hz, C=O); $^{31}$P NMR (145 MHz, CD$_2$Cl$_2$) δ-15.42; HRMS (MALDI) for C$_{30}$H$_{32}$NO$_3$PFe [M+H]$^+$ calculated: 542.1548, found: 542.1580.

Synthesis of Chiral Ferrocene 5 (chiral carboxyferrocenyl diaryl phosphine)

To a slurry of t-BuOK (4.13 g, 36.9 mmol) in Et$_2$O (100 mL) at 0° C. was added H$_2$O (0.17 mL). The slurry was stirred at 0° C. for 5 min before adding 4 (1.08 g, 2.0 mmol). The reaction was warmed to rt and stirred for 24 h. The reaction was quenched with ice H$_2$O, the layers separated and the aqueous layer washed once with Et$_2$O. The aqueous phase was acidified with 3 M HCl and extracted with CH$_2$Cl$_2$. The organic phase was dried over Na$_2$SO$_4$ and concentrated under reduced pressure. The crude product residue was purified by passing through a short pad of silica gel eluting with EtOAc. The desired product was obtained as an orange powder (0.79 g, 96% yield). mp=146–148° C.; [α]$_D$=−249.5 (c=1.07, CH$_2$Cl$_2$); $^1$H NMR (360 MHz, CD$_2$Cl$_2$) δ 3.82 (s, 1H), 4.26 (s, 5H), 4.54 (m, 1H), 5.12 (m, 1H), 7.18–7.22 (m, 2H), 7.28–7.30 (m, 3H), 7.49–7.41 (m, 3H), 7.49–7.54 (m, 2H); $^{13}$C NMR (90 MHz, CD$_2$Cl$_2$) δ 71.7, 73.1, 74.3 (d, J$_{P-C}$=15.3 Hz), 75.3, 76.4 (d, J$_{P-C}$=4.7 Hz), 80.0 (d, J$_{P-C}$=17.5 Hz), 128.4–140.2 (8 different aromatic C's), 178.3 (d, J$_{P-C}$=2.4 Hz, C=O); $^{31}$P NMR (145 MHz, CD$_2$Cl$_2$) δ-17.29; HRMS (MALDI) for C$_{23}$H$_{19}$O$_2$PFe [M+H]$^+$ calculated: 415.0551, found: 415.0534.

Synthesis of (S, S, S, S)-FAP 6

In a Schlenk flask under N$_2$ was combined acid 5 (798 mg, 1.93 mmol), (1S, 2S)-diaminocyclohexane (100 mg, 0.88 mmol), 4-dimethylaminopyridine (11 mg, 0.09 mmol) and CH$_2$Cl$_2$ (11 mL). To the resulting orange solution was added EDCI (403 mg, 2.10 mmol) in one portion. The reaction was stirred overnight at rt. The reaction solution was washed with H$_2$O and the aqueous phase extracted twice with CH$_2$Cl$_2$. The combined organic layers were washed with brine and dried over Na$_2$SO$_4$. Removal of Na$_2$SO$_4$ by filtration and concentration by rotary evaporation afforded an orange solid, which was purified by silica gel chromatography (Hexanes/EtOAc=3/1 to 2/1). The product was obtained as an orange powder (670 mg, 84% yield). mp=155–160° C. (dec.); [α]$_D$=−198.2 (c=1.1, CH$_2$Cl$_2$); $^1$H NMR (360 MHz, CD$_2$Cl$_2$) δ 1.12 (m, 4H), 1.70 (br, 2H), 1.99 (br, 2H), 3.66 (m, 4H), 4.05 (s, 1OH), 4.41 (m, 2H), 5.07 (m, 2H), 7.05–7.16 (m, 10H), 7.34–7.45 (m, 10H), 7.57 (m, 2H, NH); $^{13}$C NMR (90MHz, CD$_2$Cl$_2$) δ25.5, 33.0, 55.5, 71.3, 71.6, 72.7, 74.9 (d, J$_{P-C}$=4.3 Hz), 77.4 (d, J$_{P-C}$=11.7 Hz), 80.0 (d, J$_{P-C}$=15.3 Hz), 128.3–139.6 (8 different aromatic C's), 171.5 (d, J$_{P-C}$=2.7 Hz, C=O); $^{31}$P NMR (145 MHz, CD$_2$Cl$_2$) δ-18.9; HRMS (APCI) for C$_{52}$H$_{48}$N$_2$O$_2$P$_2$Fe$_2$ [M+H]$^+$calculated: 907.1971, found: 907.1954.

Synthesis of (S, R, R, S)-FAP 7

In a Schlenk flask under N$_2$ was combined acid 5 (1.1 g, 2.66 mmol), (1R, 2R)-diaminocyclohexane (140 mg, 1.23 mmol), 4-dimethylaminopyridine (15 mg, 0.12 mmol) and CH$_2$Cl$_2$ (20 mL). To the resulting orange solution was added EDCI (564 mg, 2.94 mmol) in one portion. The reaction was stirred overnight at rt. The reaction solution was washed with H$_2$O and the aqueous phase extracted twice with CH$_2$Cl$_2$. The combined organic layers were washed with brine and dried over Na$_2$SO$_4$. Removal of Na$_2$SO$_4$ by filtration and concentration by rotary evaporation afforded an orange solid, which was purified by silica gel chromatography (CH$_2$Cl/EtOAc=10/1). The product was obtained as an orange powder (930 mg, 84% yield). mp=160–163° C. (dec.); [α]$_D$=−299.0 (c=1.0, CH$_2$Cl$_2$); $^1$H NMR (360 MHz, CD$_2$Cl$_2$) δ 1.23 (br m, 4H), 1.57 (br, 2H), 2.14 (br, 2H), 3.64 (br m, 2H), 3.75 (s, 2H), 3.97 (s, 10H), 4.41 (m, 21), 5.06 (m, 2H), 7.08–7.24 (m, 10H), 7.36–7.39 (m, 6H), 7.47–7.51 (m, 4H), 7.69 (br s, 2H, NH); $^{13}$C NMR (90 MHz, CD$_2$Cl$_2$) δ 24.9, 32.4, 55.1, 71.3, 71.9, 73.2, 75.1 (d, J$_{P-C}$=4.2 Hz), 76.7 (d, J$_{P-C}$=12.7 Hz), 80.9 (d, J$_{P-C}$=17.6 Hz), 128.4–139.6 (8 different aromatic C's), 170.9 (d, J$_{P-C}$=2.8 Hz, C=O); $^{31}$P NMR (145 MHz, CD$_2$Cl$_2$) δ-19.34; HRMS (MALDI) for C$_{52}$H$_{48}$N$_2$O$_2$P$_2$Fe$_2$ [M+H]$^+$ calculated: 907.1971, found: 907.2022.

EXAMPLE 3

Synthesis of Chiral Xylyl FAP Ligands

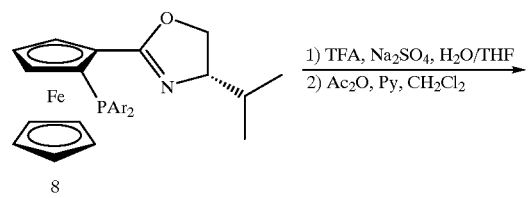

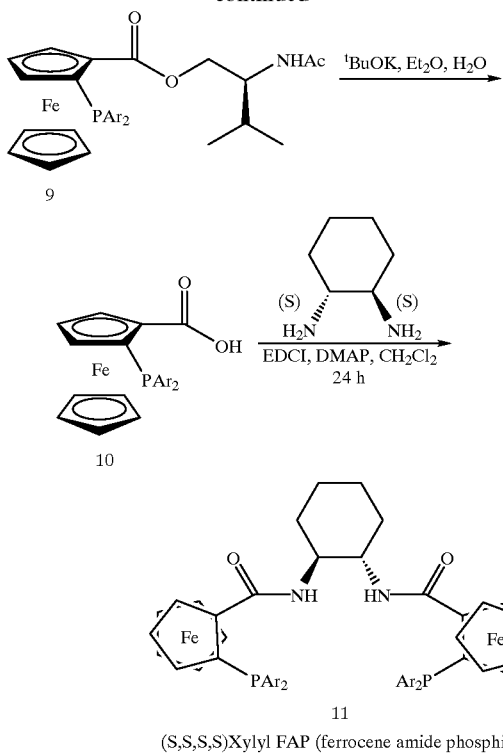

(S,S,S,S)Xylyl FAP (ferrocene amide phosphine

Synthesis of 9

Chiral oxazoline 8 was prepared in a similar way as the synthesis of 3. To a THF (150 mL) solution of 8 (6.75 g, 14.0 mmol) under $N_2$ was added $H_2O$ (13.4 mL) and anhydrous $Na_2SO_4$ (104 g). After cooling to 0° C., $CF_3COOH$ (5.8 mL, 65.5 mmol) was added and the reaction stirred overnight at rt. An additional 28 g of $Na_2SO_4$ was added and the reaction mixture was filtered under $N_2$. The $Na_2SO_4$ was washed with THF until no color remained and the filtrate was concentrated under reduced pressure affording a yellow solid. This solid was dissolved in $CH_2Cl_2$ (250 mL), cooled to 0° C. and $Ac_2O$ (25 mL, 0.26 mol) was added followed by pyridine (50 mL, 0.62 mol). The reaction mixture was stirred overnight at rt. The resulting red solution was quenched with 3 M HCl (100 mL) and the layers separated. The organic phase was washed with 3 M HCl (2×100 mL), sat. $NaHCO_3$ (1×100 mL) and dried over $Na_2SO_4$. The deep red solution was concentrated under reduced pressure and the crude product purified by passing through a short column of silica gel eluting with EtOAc. Product 9 was obtained as a yellow solid (5.7 g, 75% yield). mp =176–178° C.; $[\alpha]$=−135.9 (c=0.78, $CH_2Cl_2$); $^1H$ NMR (360 MHz, $CD_2Cl_2$) δ 0.96 (d, $J_{H-H}$=6.7 Hz, 3H, $CH_3$), 1.06 (d,$J_{H-H}$=6.7 Hz, 3H, $CH_3$), 1.69 (s, 3H, $CH_3$), 2.16–2.22 (m, 1H, CH), 2.21 (s, 3H, $CH_3$), 2.32 (s, 3H, $CH_3$), 3.74 (m, 11H), 3.79–3.87 (m, 2H, $CH_2$), 4.18 (s, 5H), 4.46–4.51 (m, 2H), 5.14 (m, 1H), 5.43 (br s, 1H, NH), 6.75 (m, 2H), 6.92 (s, 11H), 7.06–7.11 (m, 3H); $^{13}C$ NMR (90 MHz, $CD_2Cl_2$) δ 19.63, 19.82, 21.41, 21.43, 23.12, 29.56, 53.94, 65.17, 71.34, 72.57, 75.25, 75.90 (d, $J_{J-C}$=17.0 Hz), 76.22 (d, $J_{P-C}$=4.4 Hz), 78.43 (d, $J_{P-C}$=15.6 Hz), 129.9–139.9 (8 different aromatic C's), 169.49 (C=O), 171.77 (d, $J_{P-C}$=2.7 Hz, C=O); $^{31}P$ NMR (145 MHz, $CD_2Cl_2$) δ-15.56; HRMS (APCI) for $C_{34}H_{40}NO_3PFe$ $[M+H]^+$ calculated: 598.2174, found: 598.2179.

Synthesis of an Acid Synthon 10

To a slurry of t-BuOK (4.13 g, 36.9 mmol) in $Et_2O$ (100 mL) at 0° C. was added $H_2O$ (0.17 mL). The slurry was stirred at 0° C. for 5 min before adding 9 (2.0 mmol). The reaction was warmed to rt and stirred for 24 h. The reaction was quenched with ice $H_2O$, the layers separated and the aqueous layer washed once with $Et_2O$. The aqueous phase was acidified with 3 M HCl and extracted with $CH_2Cl_2$. The organic phase was dried over $Na_2SO_4$ and concentrated under reduced pressure. The crude product residue was purified by passing through a short pad of silica gel eluting with EtOAc. The desired product was obtained as an orange powder (96% yield). mp=78–80° C.; $[\alpha]_D$ =−194.2 (c=0.72, $CH_2Cl_2$); $^1H$ NMR (360 MHz, $CD_2Cl_2$) δ 2.22 (s, 6H, $CH_3$), 2.31 (s, 6H, $CH_3$), 3.86 (s, 1H), 4.21 (s, 5H), 4.53 (s, 1H), 5.09 (m, 1H), 6.76 (d, $J_{P-H}$=7.8 Hz, 2H), 6.92 (s, 1H), 7.05 (s, 1H), 7.12 (d, $J_{P-H}$=8.0 Hz, 2H); $^{13}C$ NMR (90 MHz, $CD_2Cl_2$) δ 21.4, 71.6, 72.9, 74.4 (d, $J_{P-C}$=16.0 Hz), 75.1, 76.5 (d, $J_{P-C}$=4.5 Hz), 80.2 (d, $J_{P-C}$=16.4 Hz), 130.0–139.5 (8 different aromatic C's), 176.7 (C=O); $^{31}O$ NMR (145 MHz, $CD_2Cl_2$) δ-18.16; HRMS (APCI) for $C_{27}H_{27}O_2PFe$ $[M+H]^+$ calculated: 471.1177, found: 471.1187.

Synthesis of 11

In a Schlenk flask under $N_2$ was combined acid 10 (1.93 mmol), (1S, 2S)-diaminocyclohexane (100 mg, 0.88 mmol), 4-dimethylaminopyridine (11 mg, 0.09 mmol) and $CH_2Cl_2$ (11 mL). To the resulting orange solution was added EDCI (403 mg, 2.10 mmol) in one portion. The reaction was stirred overnight at rt. The reaction solution was washed with $H_2O$ and the aqueous phase extracted twice with $CH_2Cl_2$. The combined organic layers were washed with brine and dried over $Na_2SO_4$. Removal of $Na_2SO_4$ by filtration and concentration by rotary evaporation afforded an orange solid, which was purified by silica gel chromatography (Hexanes/EtOAc=3/1 to 2/1). The product was obtained as an orange powder (84% yield), mp=160–162° C.; $^1H$ NMR (360 MHz, $CD_2Cl_2$) δ 1.26–1.35 (br m, 6H), 1.75 (br s, 2H), 2.06 (s, 12H, $CH_3$), 2.30 (s, 12H, $CH_3$), 3.70 (br s, 2H), 3.77 (s, 2H), 4.05 (s, 10OH), 4.44 (m, 2H), 5.13 (m, 2H), 6.72 (d, $J_{P-H}$=8.2 Hz, 4H), 6.84 (s, 2H), 7.03 (s, 2H), 7.09 (d, $J_{P-H}$=8.2 Hz, 4H), 7.72 (br m, 2H, NH); $^{13}C$ NMR (90 MHz, $CD_2Cl_2$) δ 21.3, 21.4, 25.2, 32.2, 55.3, 71.3, 72.7, 75.1 (d, $J_{P-C}$=3.9 Hz), 77.7 (d, $J_{P-C}$=12.5 Hz), 80.1 (d, $J_{P-C}$=16.0 Hz), 130.2–139.2 (8 different aromatic C's), 171.3 (d, $J_{P-C}$= 2.6 Hz, C=O); $^{31}P$ NMR (145 MHz, $CD_2Cl_2$) δ −19.45; HRMS (APCI) for $C_{60}H64N_2O_2P_2Fe_2$ $[M+H]^+$ calculated: 1019.3224, found: 1019.3254.

EXAMPLE 4

Synthesis of Other Chiral Ferrocene Phosphine Ligands

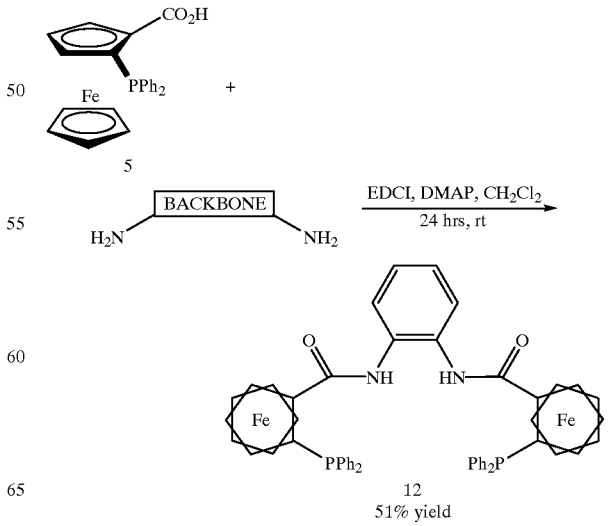

12
51% yield

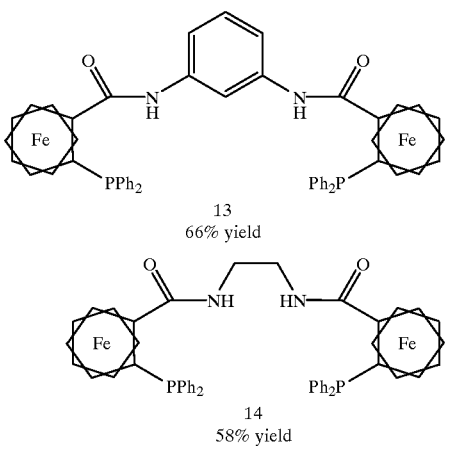

13
66% yield 14
58% yield

Synthesis of 12

In a Schlenk flask under $N_2$ was combined acid 5 (506 mg, 1.22 mmol), 1,2-phenylenediamine (60 mg, 0.55 mmol), 4-dimethylaminopyridine (14 mg, is 0.11 mmol) and $CH_2Cl_2$ (10 mL). To the resulting orange solution was added EDCI (255 mg, 1.33 mmol) in one portion. The reaction was stirred overnight at rt. The reaction solution was washed with $H_2O$ and the aqueous phase extracted three times with $CH_2Cl_2$. The combined organic layers were washed with brine and dried over $Na_2SO_4$. Removal of $Na_2SO_4$ by filtration and concentration by rotary evaporation afforded an orange solid, which was purified by silica gel chromatography (Hexanes/EtOAc=3/1). The product was obtained as an orange powder (256 mg, 51% yield). mp=148–151° C.; $^1$H NMR (360 MHz, $CD_2Cl_2$) δ 3.87 (s, 2H), 4.14 (s, 10H), 4.55 (s, 2H), 5.23 (s, 2H), 7.15–7.22 (m, 12H), 7.41–7.53 (m, 12H), 9.62 (m, 2H, NH); $^{13}$C NMR (90 MHz, $CD_2Cl_2$) δ 71.5, 72.3, 72.8, 75.6, 77.9 (d, $J_{P-C}$=12.8 Hz), 80.0 (d, $J_{P-C}$=16.3 Hz), 125.3–139.2 (11 different aromatic C's), 169.7 (d, $J_{P-C}$=3.5 Hz, C=O); $^{31}$P NMR (145 MHz, $CD_2Cl_2$) δ-19.75.

Synthesis of 13

In a Schlenk flask under $N_2$ was combined acid 5 (506 mg, 1.22 mmol), 1,3-phenylenediamine (60 mg, 0.55 mmol), 4-dimethylaminopyridine (14 mg, 0.11 mmol) and $CH_2Cl_2$ (10 mL). To the resulting orange solution was added EDCI (255 mg, 1.33 mmol) in one portion. The reaction was stirred overnight at rt. The reaction solution was washed with $H_2O$ and the aqueous phase extracted three times with $CH_2Cl_2$. The combined organic layers were washed with brine and dried over $Na_2SO_4$. Removal of $Na_2SO_4$ by filtration and concentration by rotary evaporation afforded an orange solid, which was purified by silica gel chromatography ($CH_2C_2$/EtOAc=10/1). The product was obtained as an orange powder (273 mg, 66% yield). mp=140–142° C.; $^1$H NMR (360 MHz, $CD_2Cl_2$) δ 3.92 (s, 2H), 4.16 (s, 10H), 4.53 (m, 2H), 5.19 (m, 2H), 7.20–7.33 (m, 13H), 7.40–7.45 (m, 6H), 7.58–7.63 (m, 4H), 8.02 (s, 1H), 9.10 (m, 2H, NH); $^{13}$C NMR (90MHz, $CD_2Cl_2$) δ 71.3, 72.3, 73.5, 75.3 (d, $J_{P-C}$=3.4 Hz), 76.3 (d, $J_{P-C}$=10.7 Hz), 81.2 (d, $J_{P-C}$=18.0 Hz), 111.3, 115.3, 128.7–139.6 (10 different aromatic C's), 168.7 (d, $J_{P-C}$=3.6 Hz, C=O); $^{31}$P NMR (145 MHz, $CD_2Cl_2$) δ-20.62.

Synthesis of 14

In a Schlenk flask under $N_2$ was combined acid 5 (200 mg, 0.48 mmol), 1,2-ethylenediamine (15 L, 0.22 mmol), 4-dimethylaminopyridine (5 mg, 0.04 mmol) and $CH_2Cl_2$ (5 mL). To the resulting orange solution was added DCC (99 mg, 0.48 mmol) in one portion. The reaction was stirred overnight at rt. The reaction solution was washed with $H_2O$ and the aqueous phase extracted three times with $CH_2Cl_2$. The combined organic layers were washed with brine and dried over $Na_2SO_4$. Removal of $Na_2SO_4$ by filtration and concentration by rotary evaporation afforded an orange solid, which was purified by silica gel chromatography (Hexanes/EtOAc=1/1 and 1/2). The product was obtained as an orange powder (90 mg, 47% yield). $^1$H NMR (360 MHz, $CDCl_3$) δ 3.41–3.58 (m, 4H, $CH_2CH_2$), 3.80 (s, 2H), 4.12 (s, 10H), 4.45 (m, 2H), 5.17 (br s, 2H), 7.12–7.25 (m, 10H), 7.40 (m, 6H), 7.52 (m, 4H), 7.73 (br s, 2H, NH); $^{31}$P NMR (145 MHz, $CDCl_3$) δ-19.3.

EXAMPLE 5

Asymmetric Allylic Alkylation Experiments

Representative Procedure for the Kinetic Resolution of 15:

Pd-Catalyzed Asymmetric Allylic Alkylation

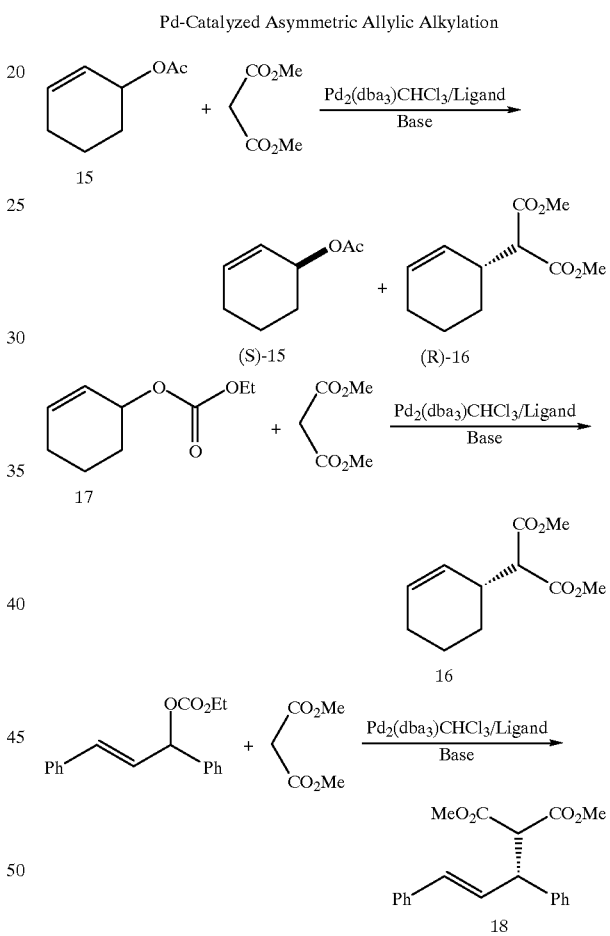

A flame-dried Schlenk flask under an atmosphere of $N_2$ was charged with $Pd_2(dba)_3 \cdot CHCl_3$ (6.2 mg, 0.006 mmol), a chiral phosphine ligand (16.3 mg, 0.018 mmol) and THF (2 mL). The catalyst solution was stirred for 1 h at rt before adding a THF (1 mL) solution of 15 (56 mg, 0.40 mmol). Dimethyl malonate (136 mL, 1.20 mmol) was added followed by CsOAc (5 mg) and BSA (296 mL, 1.20 mmol) and the reaction proceeded at rt. An aliquot was removed from the reaction, passed through a plug of silica gel with EtOAc/Hexanes (1/1) and analyzed by GC Determination of Product Enantioselectivity Enantiomers of 15 and 16 were separated by GC using a Supelco b-DEX 120 chiral capillary column. For compound 15, the retention times in minutes were 21.5 (R) and 21.8 (S) with an oven temperature of 90° C. Enantiomers of compound 16 had a retention time (min.) of 63.5 S and 64.0 R with an oven temperature of 120° C. for 60 min then ramped 5°/min to 180° C. In all cases, the flow rate was 1.0 mL/min using an FID detector. Enantiomeric excess for products 17 was determined using $^1$H NMR with the chiral shift reagent Eu(hfc)$_3$ in CDCl$_3$. Enantiomers of product 18 were separated using HPLC with a Chiralpak-AD column and a mobile phase of Hexane/2-Propanol=80/20 and a flow rate of 1.0 mL/min. Retention times in minutes were 14.3 (R) and 18.2 (S).

EXAMPLE 6

Optimization of Reaction Conditions for Pd-catalyzed Allylic Alkylation A variety of conditions have been searched, THF is a better solvent and Ligand 6 gives higher enantioselectivities.

TABLE 1

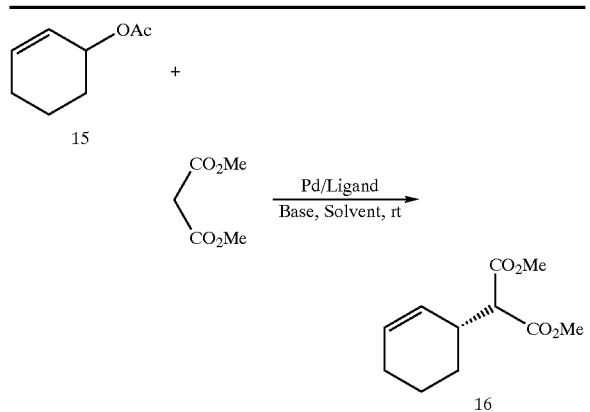

| Entry[a] | Ligand | Pd | Base | Solvent | % Conv.[e] | % ee[f] |
|---|---|---|---|---|---|---|
| 1 | 6 | [($\eta^3$-allyl)PdCl$_2$] | NaH | CH$_2$Cl$_2$ | 61 | 20 (R) |
| 2 | 6 | " | NaH/Bu$_4$NBr | " | 35 | 31 |
| 3 | 6 | " | TMG[b] | " | 28 | 38 |
| 4 | 6 | " | DBU[c] | " | 60 | 33 |
| 5 | 6 | " | Cs$_2$CO$_3$ | " | 39 | 54 |
| 6 | 6 | " | BSA/KOAc[d] | " | 65 | 69 |
| 7 | 6 | Pd$_2$(dba)$_3$ CHCl$_3$ | " | " | 80 | 67 |
| 8 | 6 | " | " | Toluene | 66 | 75 |
| 9 | 6 | " | " | CH$_3$CN | 71 | 49 |
| 10 | 6 | " | " | THF | 66 | 83 |
| 11 | 6 | [($\eta^3$-allyl)PdCl$_2$] | " | " | 68 | 81 |
| 12 | 7 | " | " | " | 67 | 30 |
| 13 | 7 | Pd$_2$(dba)$_3$ CHCl$_3$ | " | " | 53 | 37 |

[a]Pd (3 mol %), Ligand (4.5 mol %), base (3 eq), DiMeth malonate (3 eq), 15 (1 eq) in 3 mL of solvent.
[b]TMG = 1,1,3,3-tetraMethguanidine
[c]DBU = 1,8-diazabicyclo[5.4.0]undec-7-ene.
[d]5 mol % of KOAc was used.
[e]Conversion was Determn'd by GC.
[f]% ee was Determn'd by GC using a β-DEX 120 Chiral capillary column; absolute configuration determined by rotation

EXAMPLE 7

Kinetic Resolution of Substrate 15

Highly efficient enantioselective kinetic resolution has been achieved using a Pd-(S,S,S,S) FAP-6 as a catalyst (Table 2). The S-factor of 61 was achieved.

TABLE 2

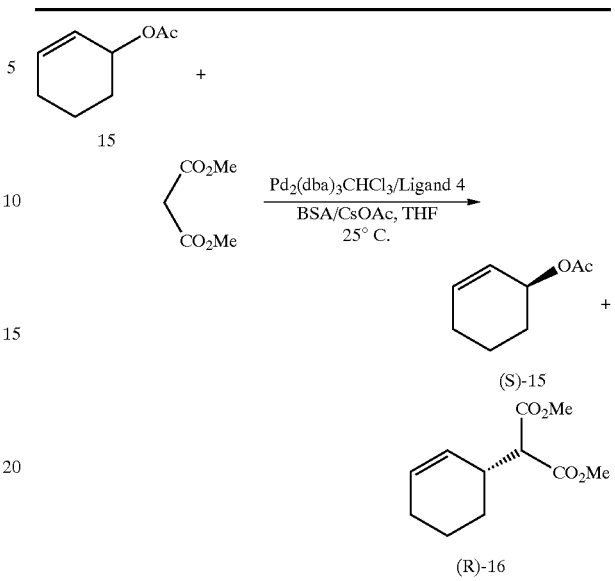

| Entry | Time (h) | % Conv.[a] | % ee[b] | % ee 16 |
|---|---|---|---|---|
| 1 | 1 | 25 | 31 | 97 |
| 2 | 2 | 39 | 59 | 95 |
| 3 | 4 | 55 | 99 | 92 |
| 4 | 6 | 63 | >99 | 82 |
| 5 | 24 | 74 | >99 | 71 |

$S = \ln(1 + C)(1 - E)/\ln(1 + C)(1 + E)$
$C = \%\ \text{conv}/100$
$E = \%\ \text{ee}/100$
$S = 61$

[a]conversion was determined by GC
[b]% ee for 15 and 16 was determined by GC using a β-Dex 120 chiral capillary column

EXAMPLE 8

Effect of Acetate Salts on Enantioselectivity

Up to 92% ee has been obtained when an allylic carbonate was used as a substrate and Pd-6 was used as the catalyst (Table 3).

TABLE 3

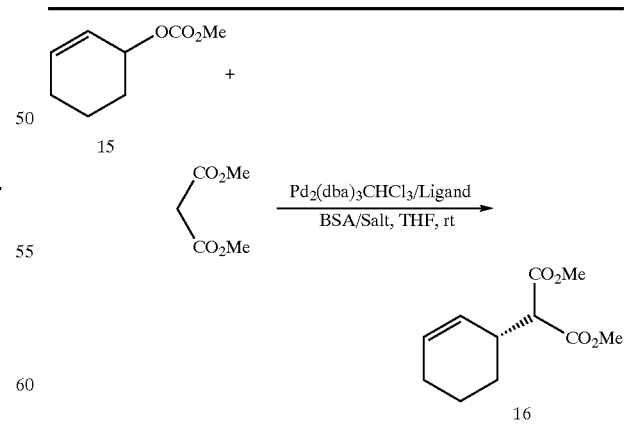

| Entry[a] | Ligand | Salt[c] | % Conv.[d] | % ee[e] | Time (h) |
|---|---|---|---|---|---|
| 1 | 6 | none | 55 | 75 | 48 |
| 2 | 6 | LiOAc | 64 | 52 | 48 |
| 3 | 6 | NaOAc | 90 | 77 | 48 |

TABLE 3-continued

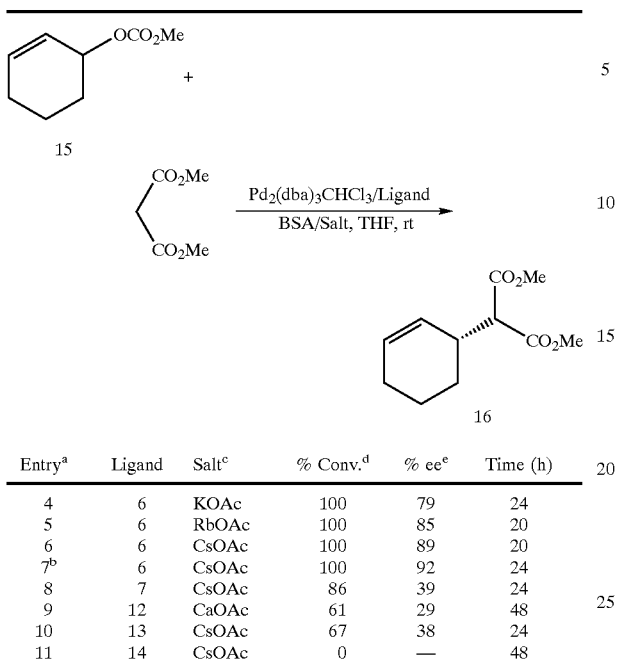

| Entry[a] | Ligand | Salt[c] | % Conv.[d] | % ee[e] | Time (h) |
|---|---|---|---|---|---|
| 4 | 6 | KOAc | 100 | 79 | 24 |
| 5 | 6 | RbOAc | 100 | 85 | 20 |
| 6 | 6 | CsOAc | 100 | 89 | 20 |
| 7[b] | 6 | CsOAc | 100 | 92 | 24 |
| 8 | 7 | CsOAc | 86 | 39 | 24 |
| 9 | 12 | CaOAc | 61 | 29 | 48 |
| 10 | 13 | CsOAc | 67 | 38 | 24 |
| 11 | 14 | CsOAc | 0 | — | 48 |

[a]Pd (3 mol %) and Ligand (4.5 mol %) was used
[b]reaction was run at 0° C.
[c]5 mol % of salt was used
[d]conversion determined by GC
[e]% ee deteremined by GC using a β-Dex 120 chiral capillary column

EXAMPLE 9

Pd-catalyzed Asymmetric Allylic Alkylation of Acyclic Allylic Acetates

The FAP ligand is also useful for Pd-catalyzed asymmetric allylic alkylation of acyclic allylic carbonates. Up to 93% ee have been achieved (Table 4).

TABLE 4

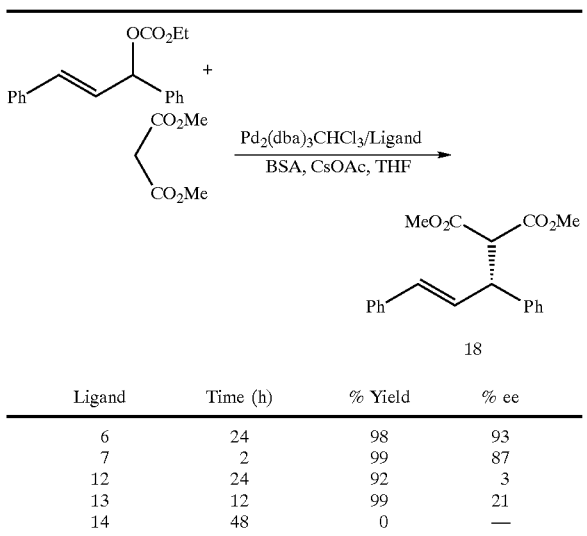

| Ligand | Time (h) | % Yield | % ee |
|---|---|---|---|
| 6 | 24 | 98 | 93 |
| 7 | 2 | 99 | 87 |
| 12 | 24 | 92 | 3 |
| 13 | 12 | 99 | 21 |
| 14 | 48 | 0 | — |

EXAMPLE 10

Catalytic [3+2] Cycloaddition

One catalyst system for [3+2] cyclization of a variety of azomethine ylides and dipolarophile substrates involves AgOAc and PPh$_3$. While Ag(I) salts have been used in stoichiometric quantities, no catalytic Ag-catalyzed reaction has been developed. In this invention, addition of PPh$_3$ forms a soluble complex with Ag(I) salts in most organic solvents. As a result, the cycloaddition reaction can be promoted efficiently with only 1 mol % of catalyst. All of the racemic pyrrolidine products in this study were formed using AgOAc/PPh$_3$ as catalyst. This proved to be a highly reactive and general catalyst system for a variety of azomethine ylide and dipolarophile substrates. Another excellent catalytic system involves Cu(I) catalysts. Cu(I) precursors, such as CuOAc and Cu(CH$_3$CN)$_4$BF$_4$, complexed with PPh$_3$ are effective catalysts for the [3+2] cyclization. These Cu(I) catalysts have not been reported.

EXAMPLE 11

General Procedure for the Synthesis of α-aminoester imines

A suspension of glycine or alanine methylester•HCl (1.1 eq), excess MgSO$_4$ and NEt$_3$ (1.1 eq) in CH$_2$Cl$_2$ was stirred at rt for 1 h. The aldehyde (1.0 eq) was added and the reaction stirred at rt overnight. The MgSO$_4$ was removed by filtration and the filtrate was washed once with H$_2$O. The aqueous phase was extracted once with CH$_2$Cl$_2$ and the combined organic layers were washed with brine. The organic phase was dried over Na$_2$SO$_4$, filtered and concentrated. Most products were sufficiently pure but if necessary could be purified by either bulb-to-bulb distillation or trituration.

EXAMPLE 12

Procedure for the Ag-catalyzed Cycloaddition of an α-aminoester imine and Dimethylmaleate The following procedure is representative for all substrates. The catalyst was prepared by stirring AgOAc (2.3 mg, 0.014 mmol) and ligand 6 (15.3 mg, 0.015 mmol) in toluene (2 mL) for 1 hr. Substrate an α-aminoester imine (0.45 mmol) was added as a solution in toluene (1 mL) followed by dimethylmaleate (62 mL, 0.50 mmol) and i-Pr$_2$NEt (8 mL, 0.045 mmol). The reaction was complete after 7 h at rt. The toluene was removed and the product isolated by silica gel chromatography eluting with Hexanes / EtOAc =2 / 1 containing 1% NEt$_3$.

EXAMPLE 13

Searching Reaction Conditions for Catalytic [3+2] Reactions

TABLE 5

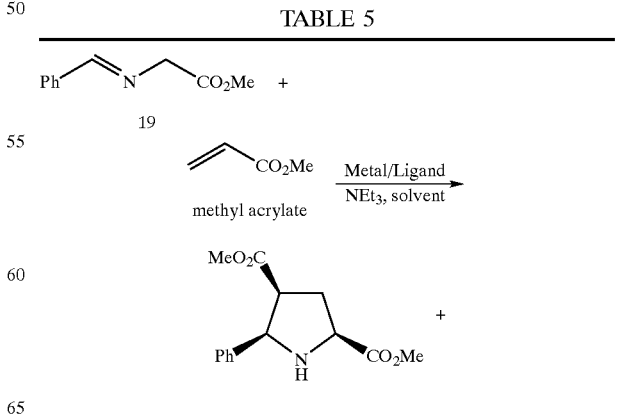

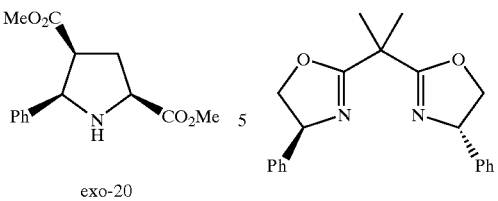

exo-20 pb-BIOX

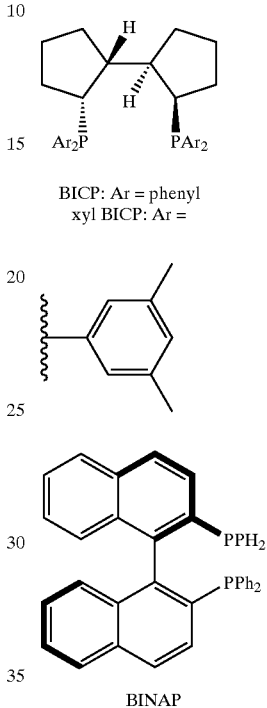

BICP: Ar = phenyl
xyl BICP: Ar =

| Entry[a] | Ligand | Cat | Solvent | endo | | exo | |
|---|---|---|---|---|---|---|---|
| | | | | % ee[b] | Yield[c] | % ee[b] | Yield[c] |
| 1 | BINAP | AgOAc | CH$_2$Cl$_2$ | 20 | 40 | 5 | 42 |
| 2 | Me-DuPhos | " | " | 29 | 35 | 4 | 40 |
| 3 | Me-PennPhos | " | " | 20 | 54 | — | — |
| 4 | Ph-BIOX | " | " | 15 | 44 | 0 | 34 |
| 5 | BICP | " | " | 34 | 70 | — | — |
| 6 | Xyl-BICP | " | " | 38 | 79 | — | — |
| 7 | BICP | " | toluene | 40 | 92 | — | — |
| 8 | BICP | CuOAc | " | 44 | 87 | — | — |

[a]19 (1.0 eq), methyl acrylate (1.2 eq.), Catalyst (1–2 mol %), Ligand (1.1–2.2 mol %), NEt$_3$ (10 mol %), solvent (3 mL).
[b]% ee determined by chiral HPLC.
[c]Isolated yield by silica gel chromatography

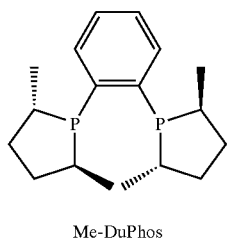

Me-DuPhos

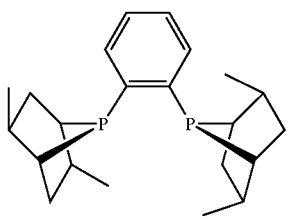

Me-PennPhos

BINAP

A variety of chiral phosphines were tested for Ag and Cu-catalyzed [3+2] cyclization reactions. Although the reaction yields are very good, the ee's are not very high. The endo-product is preferentially formed (Table 5). With dimethylmaleate as the dipolarphile, moderate ee's have been achieved in the Ag- and Cu-catalyzed [3+2] reaction (Table 6).

TABLE 6

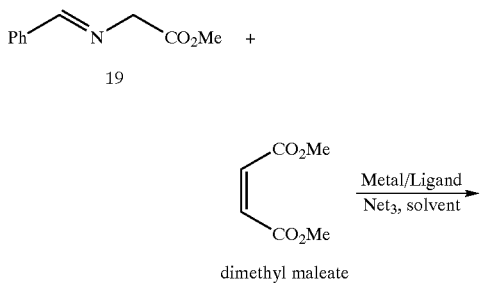

dimethyl maleate

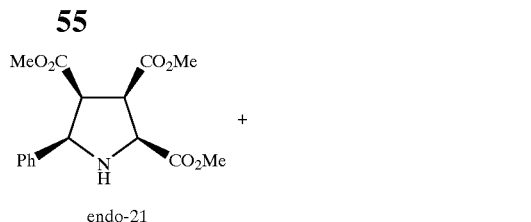

endo-21

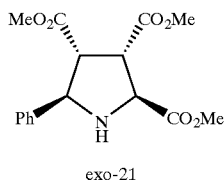

exo-21

|  |  |  |  | endo | | exo | |
|---|---|---|---|---|---|---|---|
| Entry[a] | Ligand | Cat | Solvent | % ee[b] | Yield[c] | % ee[b] | Yield[c] |
| 1 | BICP | AgOAc | toluene | 13 | 73 | — | — |
| 2 | BICP | " | CH$_2$Cl$_2$ | 20 | 88 | — | — |
| 3 | BINAP | " | toluene | 13 | 61 | 10 | 15 |
| 4 | BINAP | Cu(CH$_3$CN)$_4$BF$_4$ | CH$_2$Cl$_2$ | — | — | 8 | 83 |
| 5 | C3Tunaphos | " | " | — | — | 38 | 71 |
| 6 | C3Tunaphos | Cu(CH$_3$CN)$_4$PF$_6$ | " | — | — | 41 | 85 |
| 7 | SkewPhos | Cu(CH$_3$CN)$_4$BF$_4$ | " | — | — | 30 | 71 |

[a]19 (1.0 eq), dimethyl maleate (1.2 eq), Catalyst (2 mol %), Ligand (2.2 mol %), NEt$_3$ (10 mol %), solvent (3 mL).
[b]% ee determined by chiral HPLC.
[c]Isolated yield by silica gel chromatography.

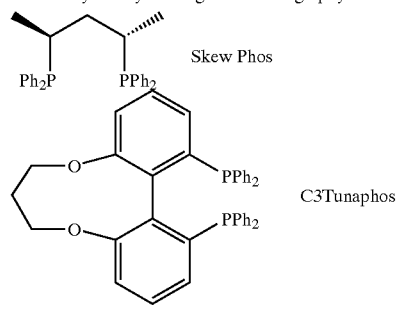

EXAMPLE 14

Ag-Catalyzed Asymmetric [3+2] Cyclization with FAP and related ligands (Table 7)

Conditions have been optimized for achieving high ee's with Ag-FAP catalysts. FAP and XylFAP are better catalysts for this transformation.

TABLE 7

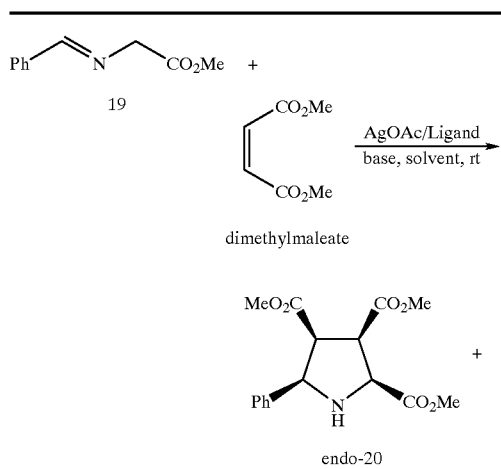

dimethylmaleate endo-20

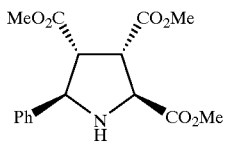

exo-20

|  |  |  |  | endo | | exo | |
| --- | --- | --- | --- | --- | --- | --- | --- |
| Entry[a] | Ligand | Base | Solvent | % ee[c] | Yield[d] | % ee[c] | Yield[d] |
| 1 | 6 (FAP) | NEt$_3$ | CH$_2$Cl$_2$ | 74 | 73 | 45 | 19 |
| 2 | 6 | " | " | 74 | 62 | 36 | 21 |
| 3 | 6 | " | THF | 69 | 89 | 56 | 7 |
| 4 | 6 | " | toluene | 75 | 91 | 52 | 3 |
| 5 | 6 | i-Pr$_2$NEt | " | 76 | 94 | — | — |
| 6 | 6 | DMAP[b] | " | 75 | 90 | — | — |
| 7 | 6 | 2,6-di-$^t$Bu-pyridine | " | 72 | 94 | — | — |
| 8 | 6 | (−)-Sparteine | " | 76 | 92 | — | — |
| 9 | 11 (Xyl FAP) | i-Pr$_2$NEt | " | 86 | 88 | — | — |
| 10 | Trost ligand | " | " | 59 | 70 | — | — |

[a]15a (1.0 eq), dimethylmaleate (1.2 eq), AgOAc (3 mol %), ligand (3.3 mol %), base (10 mol %), solvent (3 mL)
[b]DMAP = 4-dimethylaminopyridine
[c]% ee was determined by HPLC
[d]isolated yield by silica gel chromatography

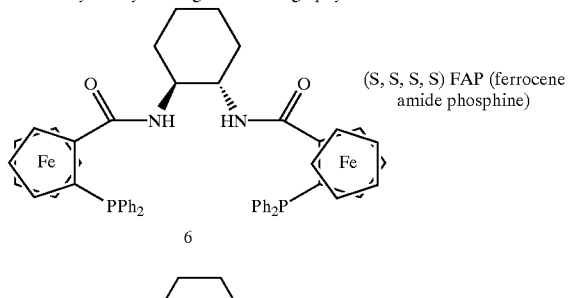

(S, S, S, S) FAP (ferrocene amide phosphine)

6

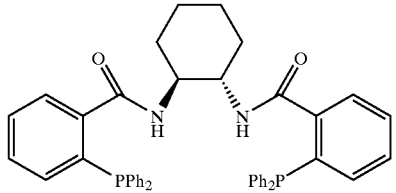

Trost ligand

EXAMPLE 15

Change of the Dipolarophile Substrate in the Ag-Xyl-FAP Catalyzed [3+2] Reaction (Table 8)

TABLE 8

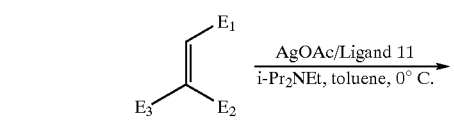

| Entry | E$_1$ | E$_2$ | E$_3$ | Time (h) | Yield | % ee |
| --- | --- | --- | --- | --- | --- | --- |
| 1 | CO$_2$Me | CO$_2$Me | H | 7 | 86 | 87 |
| 2 | CO$_2$Me | H | CO$_2$Me | 8 | 88 | 52 |
| 3 | CO$_2$Me | H | H | 8 | 90 | 60 |
| 4 | CO$_2^t$Bu | H | H | 72 | 85 | 93 |
| 5 | CO$_2^i$Pr | CO$_2^i$Pr | H | 48 | 87 | 87 |

EXAMPLE 16

Change of the Dipole Substrate (Table 9)

With different dipole substrates, a large number of chiral five-membered ring compounds can be conveniently prepared. High enantioselectivities were achieved when Ag-Xyl-FAP (11) was employed as the catalyst (Table 9).

TABLE 9

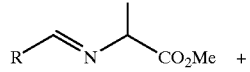

| Entry[a] | 19 | R | R' | Temp (° C.) | Time (h) | Yield[d] | % ee[e] |
|---|---|---|---|---|---|---|---|
| 1 | a | phenyl | H | 0 | 7 | 88 | 86 |
| 2 | b | p-chlorophenyl | H | 0 | 7 | 96 | 92 |
| 3 | c | o-chlorophenyl | H | 0 | 7 | 96 | 86 |
| 4 | d | p-anisyl | H | 0 | 7 | 98 | 92 |
| 5 | e | p-toluyl | H | 0 | 7 | 93 | 88 |
| 6 | f | o-toluyl | H | 0 | 7 | 91 | 90 |
| 7 | g | 1-naphthyl | H | 0 | 7 | 73 | 85 |
| 8 | h | 2-naphthyl | H | 0 | 14 | 98 | 97 |
| 9[b] | i | t-butyl | H | 25 | 72 | 37 | 76 |
| 10[b] | j | i-propyl | H | 25 | 48 | 82 | 70 |
| 11[b] | k | cyclohexyl | H | 25 | 48 | 82 | 81 |
| 12 | l | phenyl | CH$_3$ | 25 | 48 | 47 | 52 |
| 13[c] | l | phenyl | CH$_3$ | 25 | 48 | 70 | 65 |

[a]AgOAc (3 mol %) and ligand (3.3 mol %) was used unless noted otherwise
[b]AgOAc (5 mol %) and ligand (5.5 mol %) was used
[c]ligand 6 was used
[d]isolated yield by silica gel chromatography
[e]% ee determined by HPLC.

EXAMPLE 17

Synthesis of other ferrocene chiral ligands:

Other chiral PNNP ferrocene ligands can be prepared by chiral ferrocene phosphino aldehydes. These synthons are useful for making an array of chiral ligands. Chiral acetal protected ferrocenes can also be used to make other chiral ferrocene ligands. The synthetic path is outlined below:

Ligand synthesis

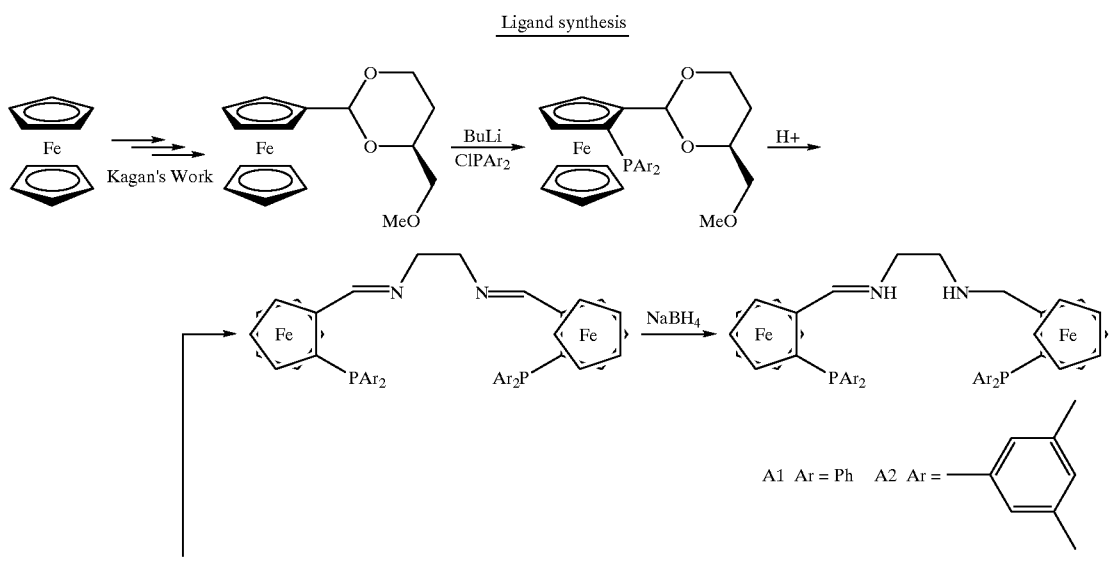

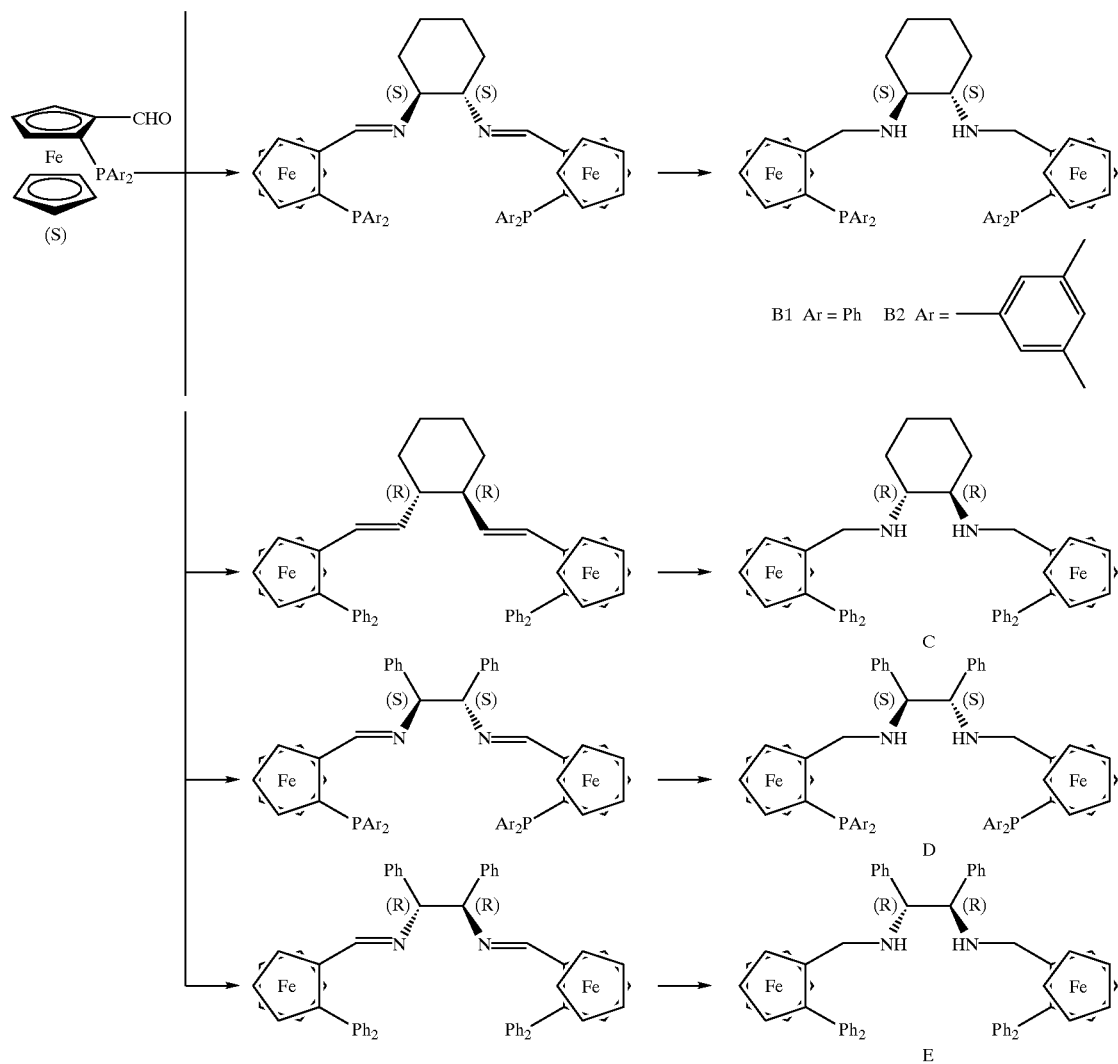
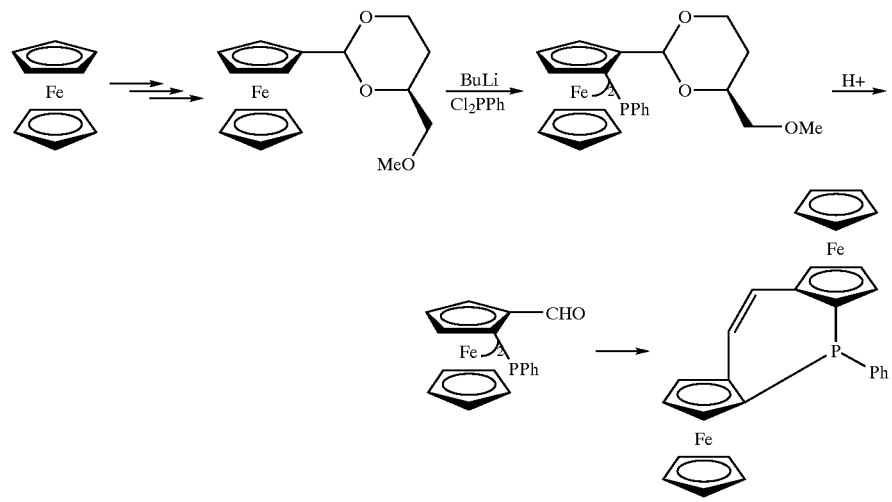
Ferrocene Ligand Synthesis

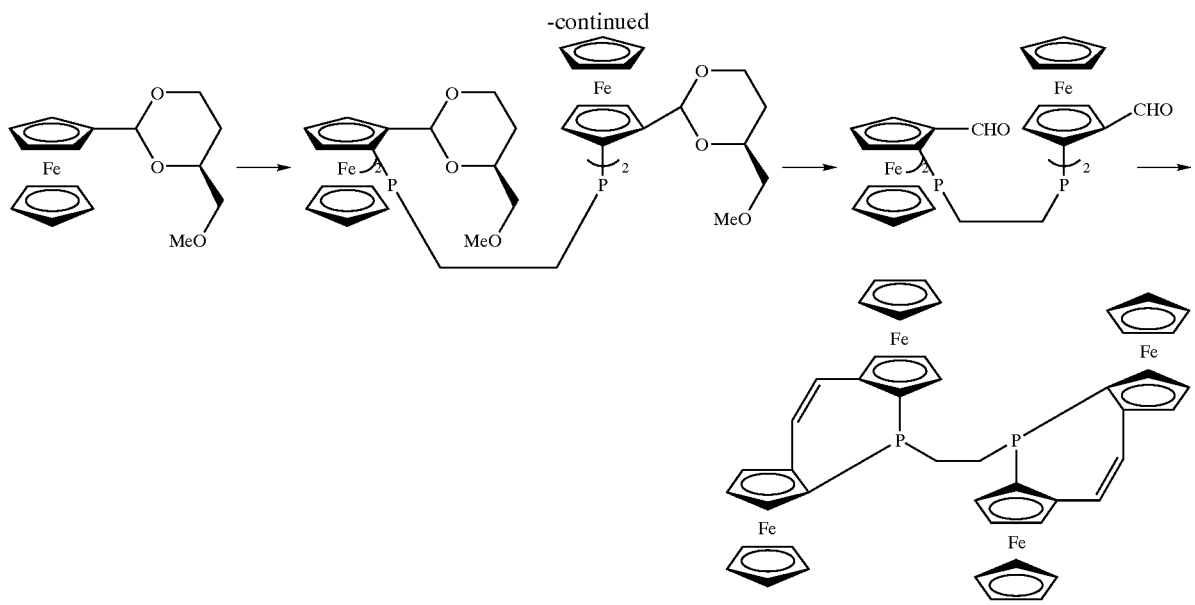
EXAMPLE 18
Hydrogenation of simple ketones:
Using the PNNP ligands, a variety of substrates have been tested for asymmetric reduction. The results with Ru catalysts are outlined as follows:
Ketone Reduction
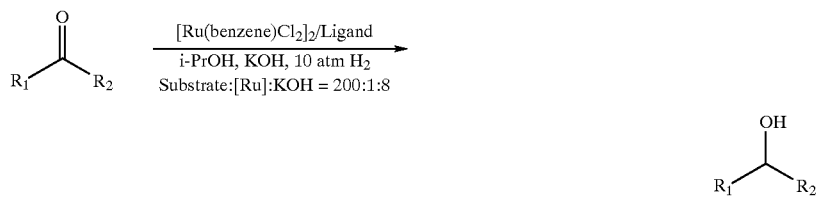
100% conversion
| Substrate | Ligand/ee (%) | | | | | | |
|---|---|---|---|---|---|---|---|
| | A1 | A2 | B1 | B2 | C | D | E |
| acetophenone | 11.8 (S) | 17.0 (R) | 12.2 (S) | 62.4 (R) | 32.5 (S) | 9.5 (R) | 9.7 (R) |
| 2'-methylacetophenone | | 24.4 (R) | 67.6 (R) | 84.8 (R) | | | |

-continued

Ketone Reduction

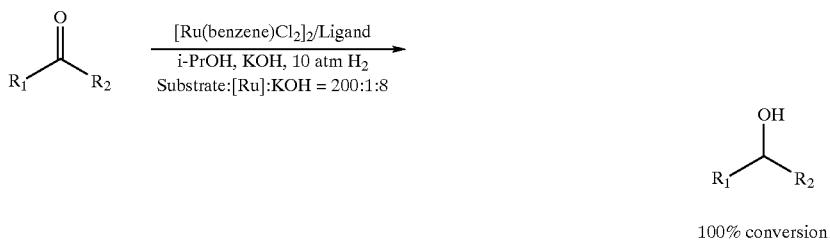

| Substrate | Ligand/ee (%) | | | | | | |
|---|---|---|---|---|---|---|---|
| | A1 | A2 | B1 | B2 | C | D | E |
| (1-naphthyl methyl ketone) | 43.8 (R) | 50.8 (R) | 69.0 (R) | 73.7 (R) | 63.1 (S) | 21.5 (R) | 27.3 (S) |
| (α-tetralone) | 58.2 (S) | 27.2 (R) | 27.0 (S) | 59.4 (R) | 0 | 51.1 (S) | 19.1 (S) |
| (pinacolone) | 77.2 (R) | | 11.5 (R) | 51.5 (R) | | | |
| (cyclohexyl methyl ketone) | | | | 25.7 (R) | | | |

The present invention has been described with particular reference to the preferred embodiments. It should be understood that the foregoing descriptions and examples are only illustrative of the invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

What is claimed is:

1. A ligand selected from the group consisting of compounds represented by the formulas:

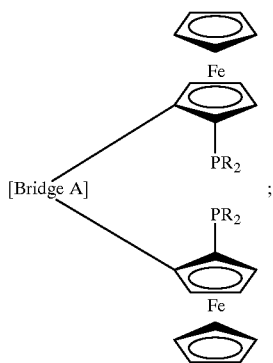

-continued

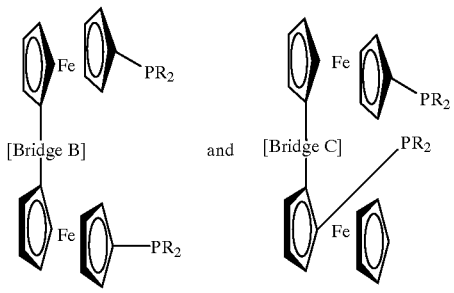

wherein "bridge A" is selected from the group consisting of: —CONH—R*—NHCO—, —CO—OR*O—CO—, —CO—R*CO—, —CH=N—R*—N=CH—, —CH₂NH—R*—NHCH₂—, —CH₂NHCO—R*—CONHCH₂—, —C*H(R¹)NH—R*—NHC*H(R¹)—, C*H(R¹)NHCO—R*—CONHC*H(R¹)—, —CONH—R—NHCO—, —CO—ORO—CO—, —CO—R—CO—, —CH=N—R—N=CH—, —CH₂NH—R—NHCH₂—, —CH₂NHCO—R—CONHCH₂—, —C*H(R¹)NH—RNH—C*H(R¹)—, —C*H(R¹)NHCO—R—CONHC*H(R¹)—, C=O, C=S, SO₂, —PO(OR¹)—, —PO(NR¹)—, —PO(NR¹₂)—, Si(R¹)₂—, —R—*, and —R—;

wherein "bridge B" has a stereogenic carbon center, wherein said "bridge B" is selected from the group consisting of: —CONH—R*—NHCO—, —CO—OR* O—CO—, —CO—R*—CO—, —CH=N—R*—N=CH—, —CH₂NH—R*NHCH₂—, —CH₂NHCO—R*—CONHCH₂—, —C*H(R¹)NH—R*—NHC*H(R¹)—, —C*H(R¹)NHCO—R*—CONHC*H(R¹)—, —C*H(R¹)NH—RNH—C*H(R¹)—, —C*H(R¹)NHCO—R—CONHC*H(R¹)—, and —R—*;

wherein "bridge C" is selected from the group consisting of: CO, SO₂, CH=CH, —CONHR*NHCO— and —(CH₂)n— wherein n is 0, 1 or 2; and wherein R¹ is selected from the group consisting of: an alkyl, aryl, aralkyl, alkaryl, and a substituted derivative thereof; —R— is selected from the group consisting of: an alkylene, arylene and a substituted derivative thereof; and * indicates the presence of a stereogenic carbon center.

2. The ligand of claim 1, wherein R¹ is an alkyl, aryl, aralkyl or alkaryl of 1 to 22 carbon atoms, and wherein each R¹ optionally has one or more substituents, each independently selected from the group consisting of: halogen, ester, ketone, carboxylic acid, hydroxy, alkoxy, aryloxy, thiol, alkylthio and dialkylamino.

3. The ligand of claim 1, wherein —R— is selected from the group consisting of: —(CH₂)ₙ— where n is an integer in the range of from 1 to 8, 1,2-divalent phenyl, 2,2'-divalent-1,1'-biphenyl, 2,2'-divalent-1,1'-binaphthyl and ferrocene, and wherein each —R— optionally has one or more substituents, each independently selected from the group consisting of: aryl, alkyl, halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine.

4. The ligand of claim 1, wherein said ligand is a racemic mixture of enantiomers.

5. The ligand of claim 1, wherein said ligand is a non-racemic mixture of enantiomers.

6. The ligand of claim 1, wherein said ligand is one of the enantiomers.

7. The ligand of claim 1, having an optical purity of at least 85% ee.

8. The ligand of claim 1, having an optical purity of at least 95% ee.

9. The ligand of claim 1, selected from the group consisting of compounds represented by the formulas:

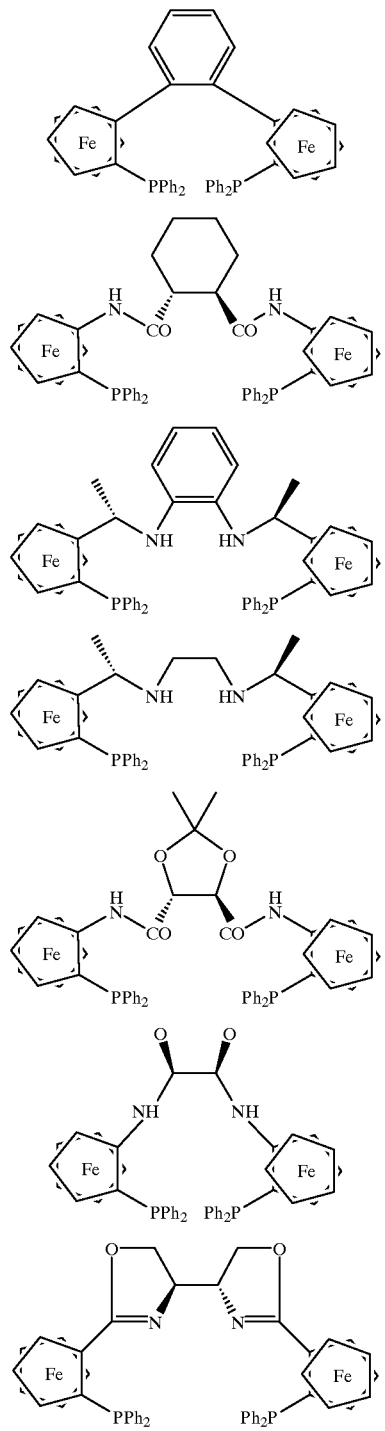

-continued
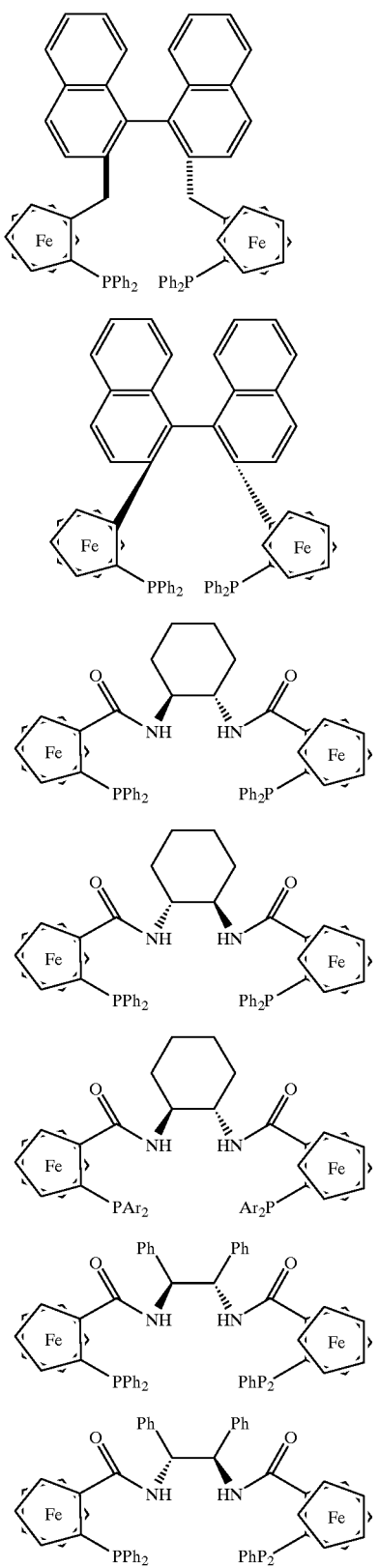
-continued
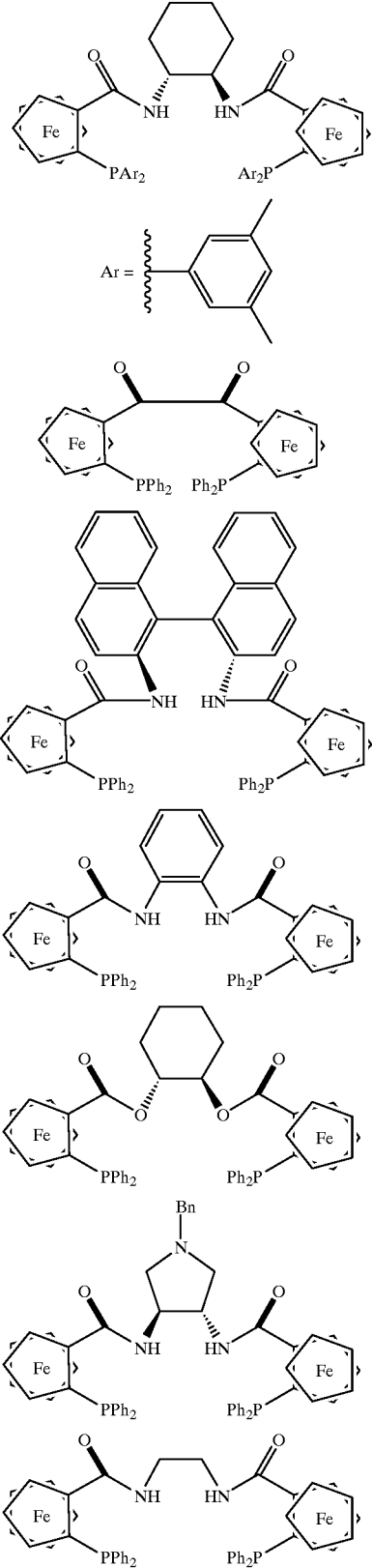

-continued
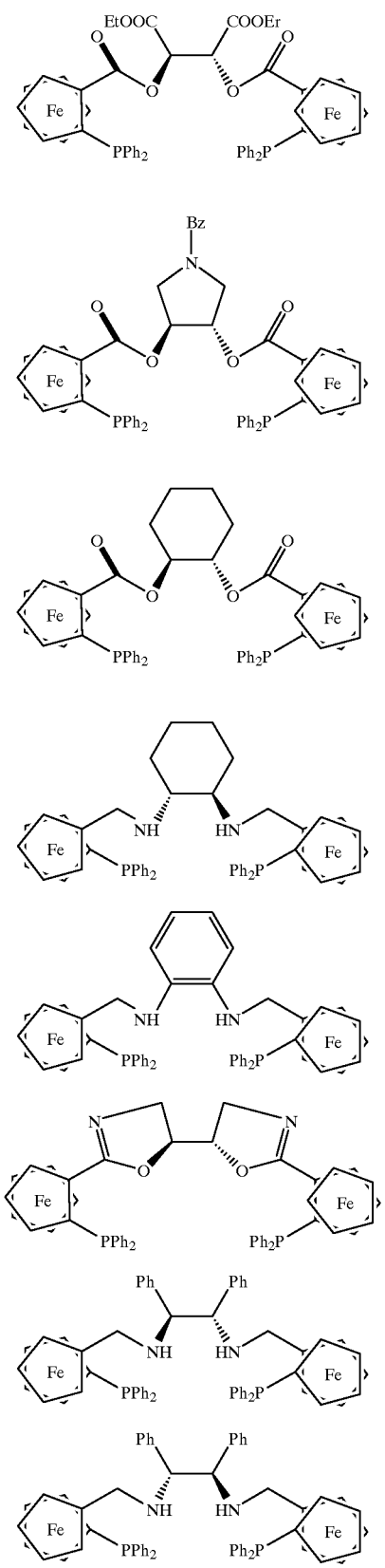
-continued
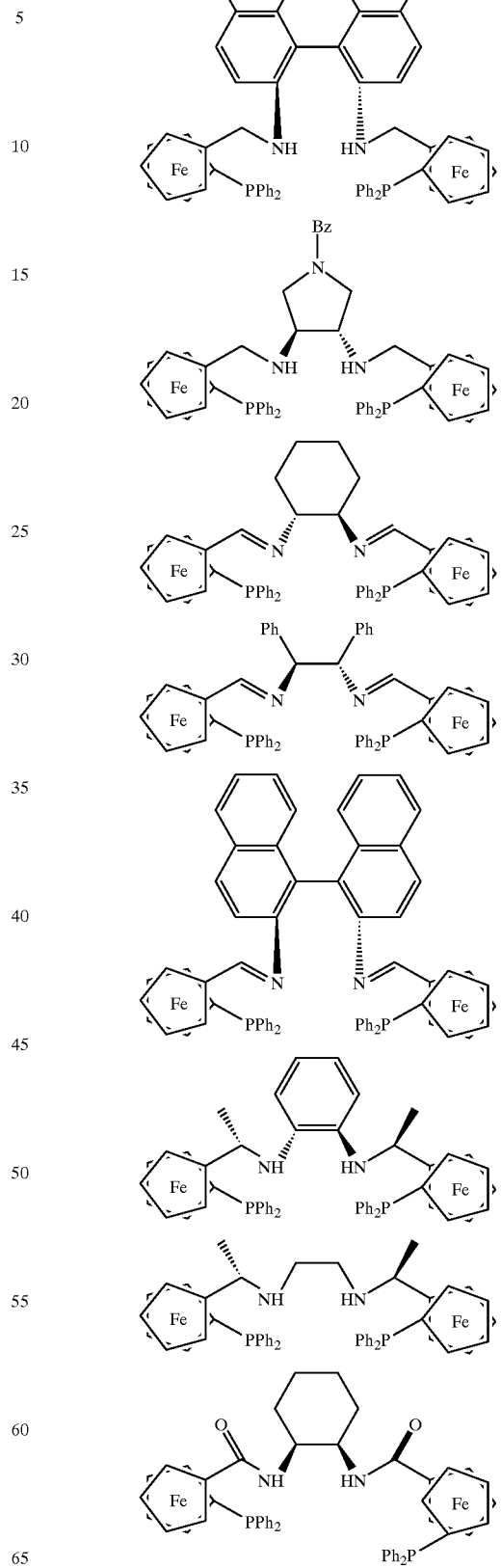

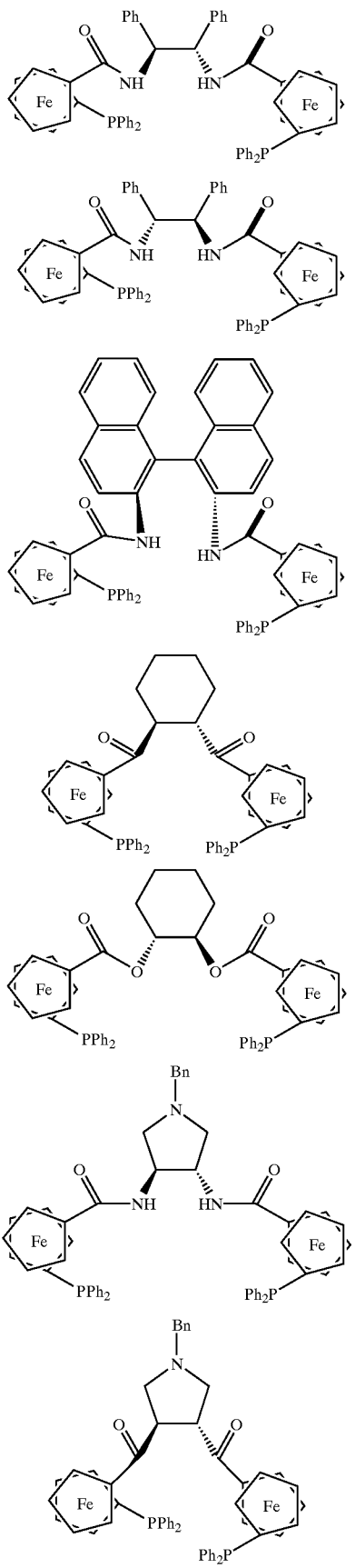

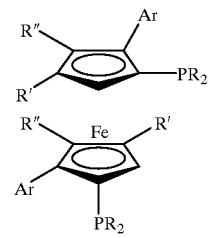

10. A ligand selected from the group consisting of compounds represented by the formulas:

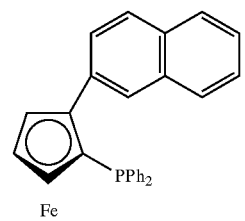

wherein R is selected from the group consisting of: an alkyl, aryl, substituted alkyl and substituted aryl; Ar is a susbtituted or unsubstituted aryl group; wherein Ar and R" together form an extended arene; wherein each R' and R" is independently selected from the group consisting of: H, alkyl, aryl substituted alkyl, substituted aryl, ester and alkoxy or wherein R'—R" together form a cyclic alkyl or a extented arene.

11. The ligand of claim 10, wherein said ligand is a non-racemic mixture of enantiomers.

12. The ligand of claim 10, wherein said ligand is one of the enantiomers.

13. The ligand of claim 10, having an optical purity of at least 85% ee.

14. The ligand of claim 10, wherein said ligand is selected from the group consisting of compounds represented by the formulas:

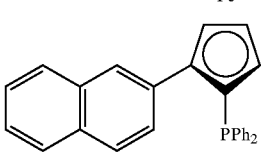

-continued

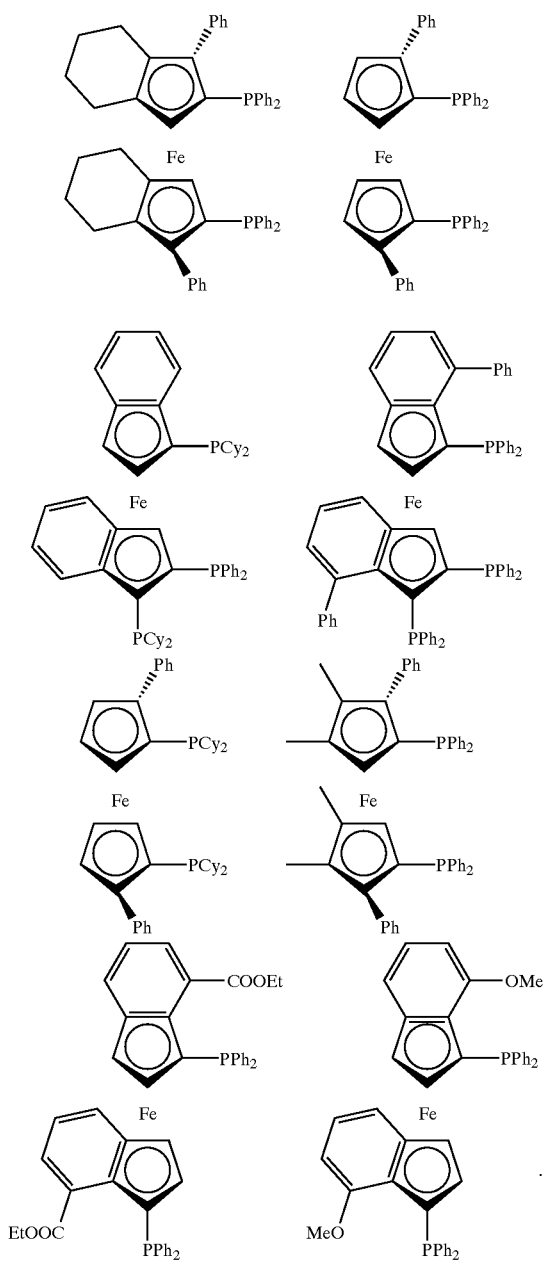

15. A ligand represented by the formula:

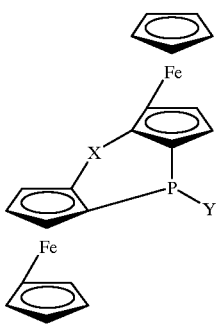

wherein X is selected from the group consisting of: CO, $SO_2$, $(CH_2)n$ wherein n=0, 1 or 2, and CH=CH;

wherein Y is selected from the group consisting of: an alkyl, aryl, substituted alkyl, substituted aryl and a group represented by the formula:

—(linker)—W wherein W is represented by the formula:

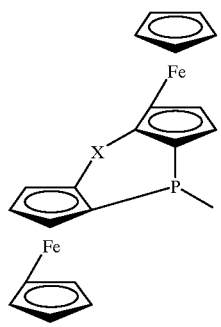

wherein X has the same meaning as above; and wherein said "linker" is selected from the group consisting of: —$(CH_2)_n$—where n is an integer in the range of from 1 to 8, 1,2-divalent phenyl, 2,2'-divalent-1,1'-biphenyl, 2,2'-divalent-1,1'-binaphthyl and ferrocene, and wherein each "linker" optionally has one or more substituents, each independently selected from the group consisting of: aryl, alkyl, halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine.

16. The ligand of claim 15, selected from the group consisting of compounds represented by the formulas:

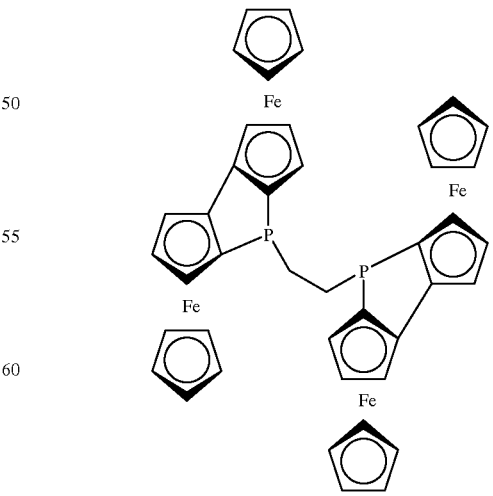

-continued

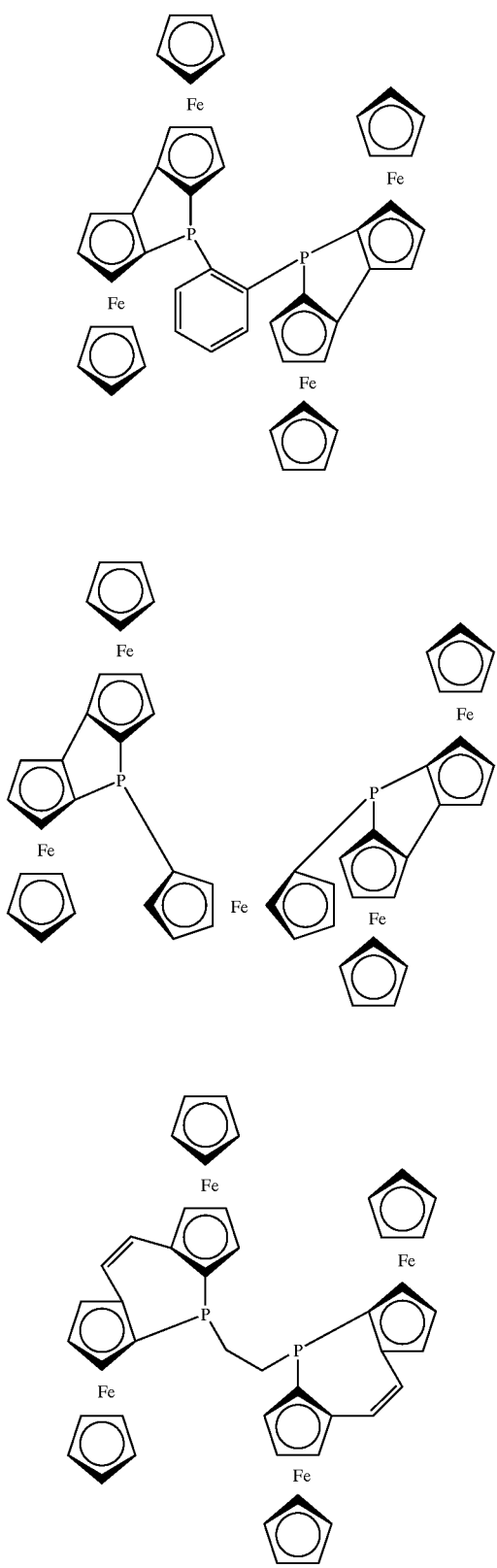

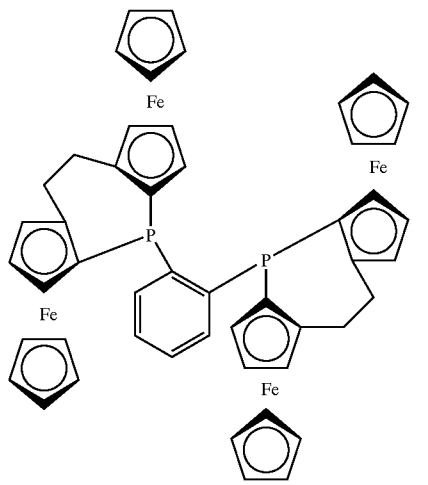

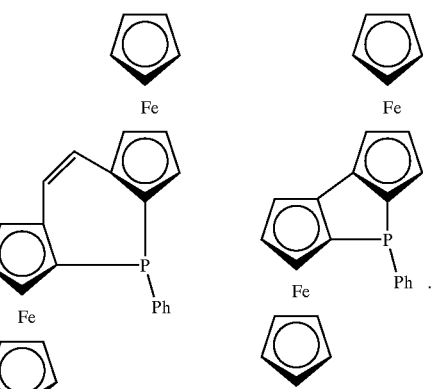

17. The ligand of claim 15, wherein said ligand is a non-racemic mixture of enantiomers.

18. The ligand of claim 15, wherein said ligand is one of the enantiomers.

19. The ligand of claim 15, having an optical purity of at least 85% ee.

20. A ligand represented by the formula:

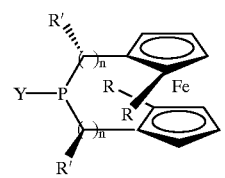

n = 0,1 wherein R is selected from the group consisting of: H, alkyl, aryl, substituted alkyl, substituted aryl, silyl, ester, amide, oxazoline and phosphate, with the proviso that R is H when R' is not H; R' is selected from the group consisting of: H, alkyl, aryl, substituted alkyl and substituted aryl; n is 0 or 1;

Y is selected from the group consisting of: alkyl, aryl, substituted alkyl, substituted aryl and a group represented by the formula:

—(linker)—W wherein W is represented by the formula:

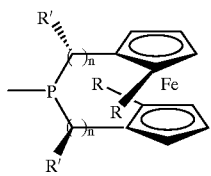

n = 0,1 wherein said "linker" is selected from the group consisting of: —$(CH_2)_n$— where n is an integer in the range of from 1 to 8, 1,2-divalent phenyl, 2,2'-divalent-1,1'-biphenyl, 2,2'-divalent-1,1'-binaphthyl and ferrocene, and wherein each "linker" optionally has one or more substituents, each independently selected from the group consisting of: aryl, alkyl, halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine.

21. The ligand of claim 20, selected from the group consisting of compounds represented by the formulas:

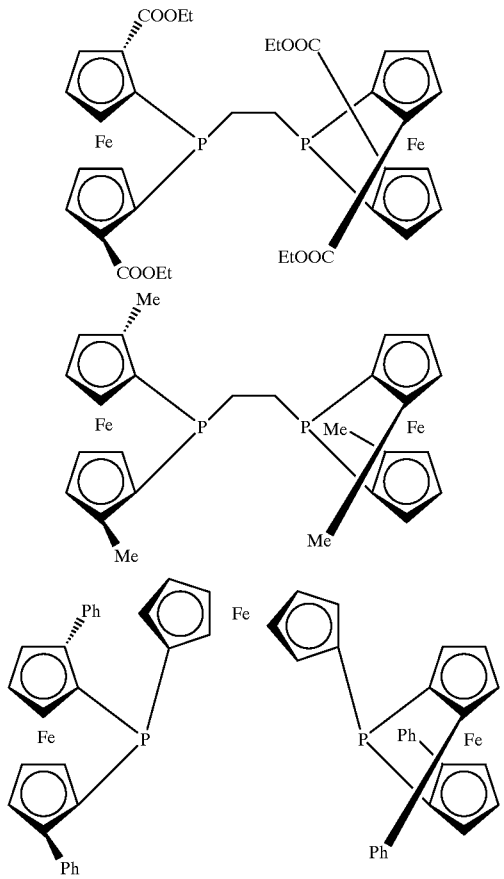

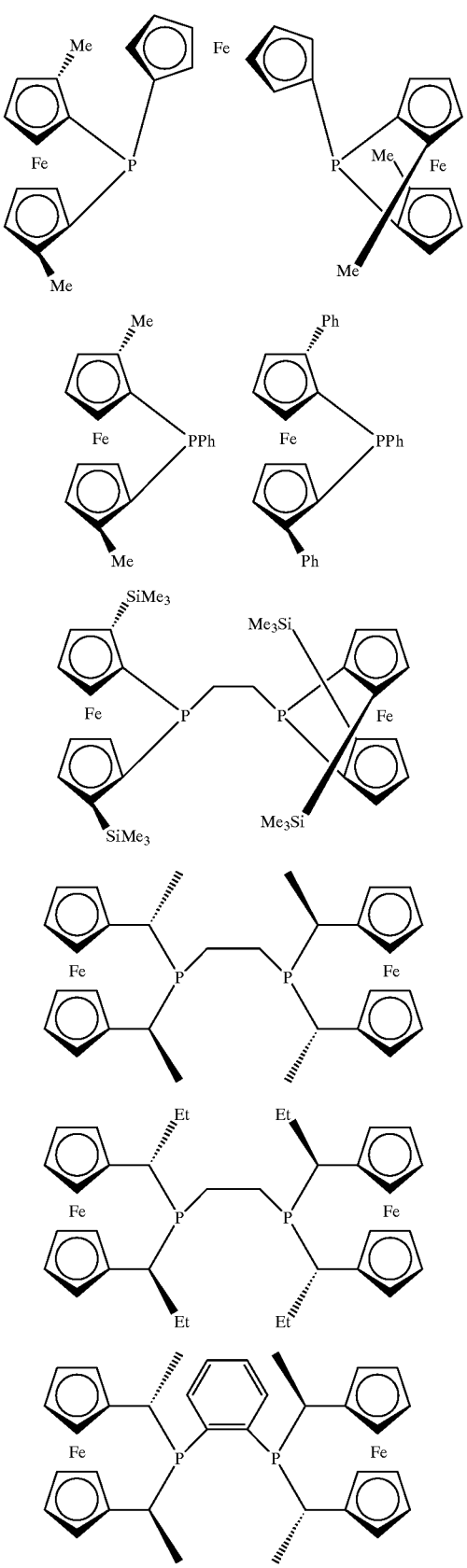

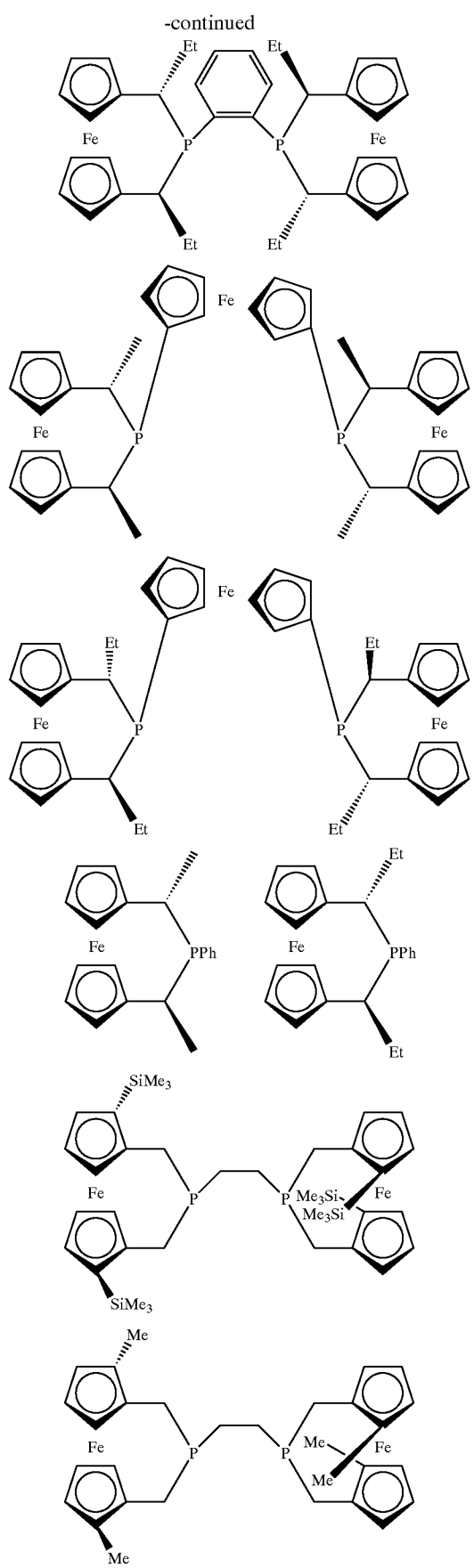
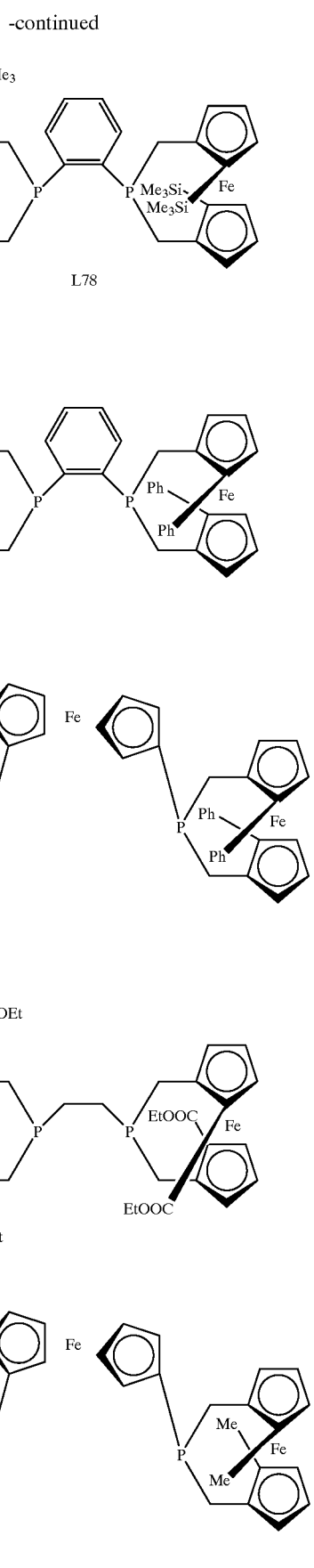

-continued

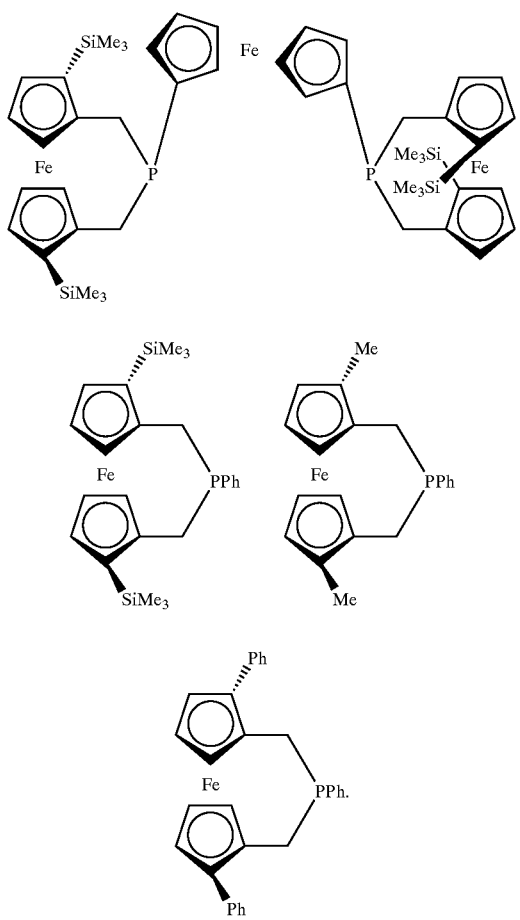

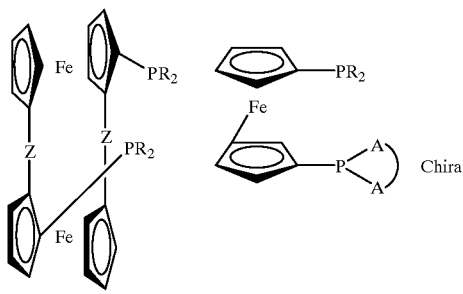

22. The ligand of claim 20, wherein said ligand is a non-racemic mixture of enantiomers.
23. The ligand of claim 20, wherein said ligand is one of the enantiomers.
24. The ligand of claim 20, having an optical purity of at least 85% ee.
25. A ligand selected from the group consisting of compounds represented by the formulas:

wherein R is selected from the group consisting of: alkyl, aryl, substituted alkyl and substituted aryl; Z is selected from the group consisting of: CO, $SO_2$ and —$(CH_2)_n$— wherein n=0, 1 or 2; each A is independently a group containing an $sp^2$ or $sp^3$ hybridized N, O, C or S atom, wherein two A groups form a cyclic compound via a chiral connecting group selected from the group consisting of: —NHR*NH—, —OR*O—, —SR*S—, —Binol— and —$CH_2R^*CH_2$—; wherein each R* is a chiral alkyl or aryl group.

26. The ligand of claim 25, wherein said R* group is selected from the group consisting of: 1,2-divalent phenyl and 2,2'-divalent-1,1'binaphthyl.
27. The ligand of claim 25, selected from the group consisting of compounds represented by the formulas:

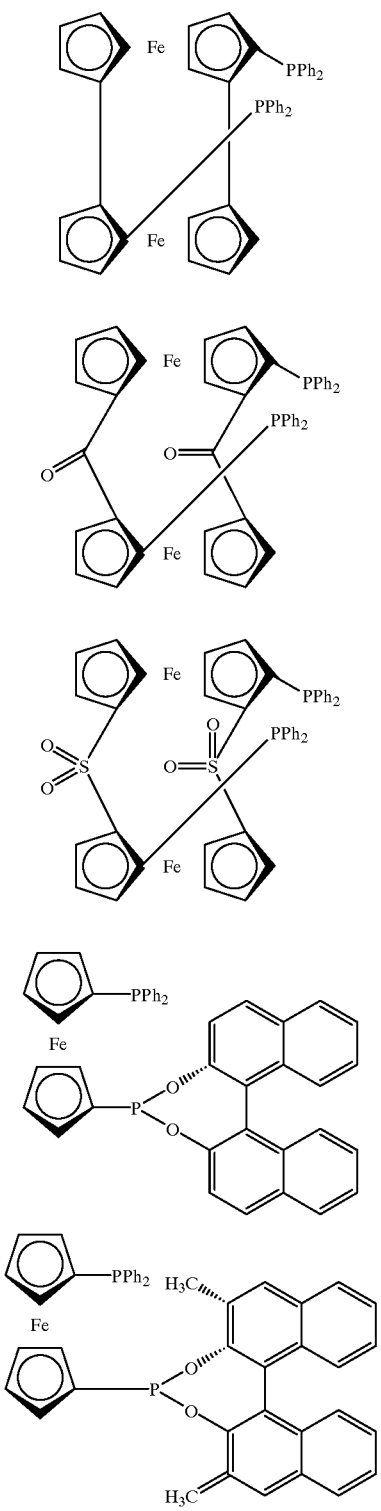

-continued

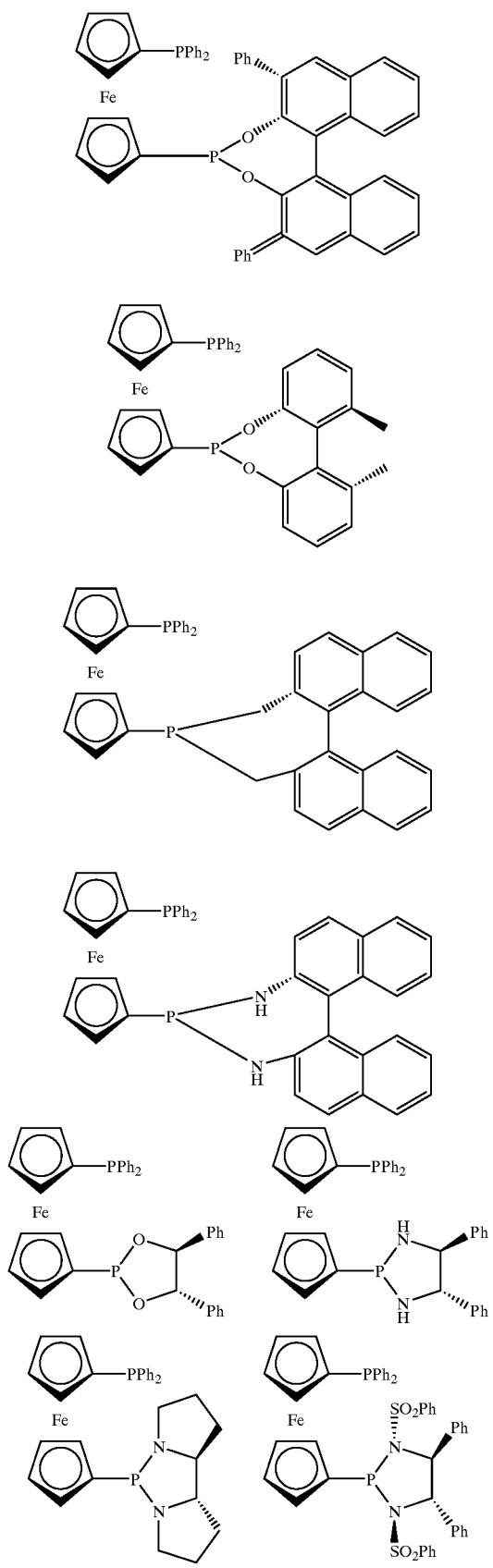

-continued

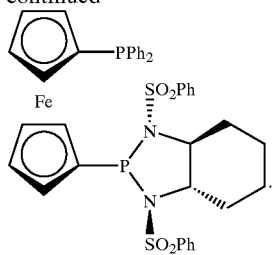

28. The ligand of claim 25, wherein said ligand is a non-racemic mixture of enantiomers.

29. The ligand of claim 25, wherein said ligand is one of the enantiomers.

30. The ligand of claim 25, having an optical purity of at least 85% ee.

31. A catalyst prepared by a process comprising: contacting a transition metal salt, or a complex thereof, and a ligand selected from the group consisting of compounds represented by:

(a)

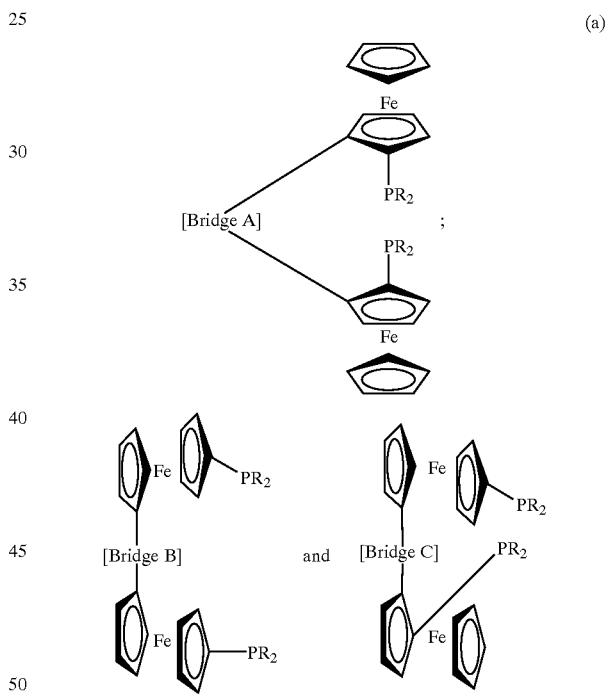

wherein "bridge A" is selected from the group consisting of: —CONH—R*—NHCO—, —CO—OR*O—CO—, —CO—R*—CO—, —CH=N—R*—N=CH—, —CH$_2$NH—R*—NHCH$_2$—, —CH$_2$NHCO—R*—CONHCH$_2$—, —C*H(R$^1$)NH—R*—NHC*H(R$^1$)—, —C*H(R$^1$)NHCO—R*—CONHC*H(R$^1$)—, —CONH—R—NHCO—, —CO—ORO—CO—, —CO—RCO—, —CH=N—R—N=CH—, —CH$_2$NH—R—NHCH$_2$—, —CH$_2$NHCO—R—CONHCH$_2$—, —C*H(R$^1$)NH—RNH—C*H(R$^1$)—, —C*H(R$^1$)NHCO—RCONHC*H(R$^1$)—, C=O, C=S, SO$_2$, —PO(OR$^1$)—, —PO(NHR$^1$)—, —PO(NR$^1$$_2$)—, Si(R$^1$)$_2$—, —R—*, and —R—;

wherein "bridge B" has a stereogenic carbon center, wherein said "bridge B" is selected from the group consisting of: —CONH—R*—NHCO—, —CO—OR*O—CO—, —CO—R*—CO—, —CH=N—R*—N=CH—, —CH$_2$NH—R*—NHCH$_2$—, —CH$_2$NHCO—R*—CONHCH$_2$—, —C*H(R$^1$)NH—R*—NHC*H(R$^1$)—, —C*H(R$^1$)NHCO—R*—CONHC*H(R$^1$)—, —C*H(R$^1$)NH—RNH—C*H(R$^1$)—, —C*H(R$^1$)NHCO—R—CONHC*H(R$^1$)—, and —R—*;

wherein "bridge C" is selected from the group consisting of: CO, SO$_2$, CH=CH, —CONHR*NHCO— and —(CH$_2$)n— wherein n is 0, 1 or 2; and wherein R$^1$ is selected from the group consisting of: an alkyl, aryl, aralkyl, alkaryl, and a substituted derivative thereof; —R— is selected from the group consisting of: an alkylene, arylene and a substituted derivative thereof; and * indicates the presence of a stereogenic carbon center;

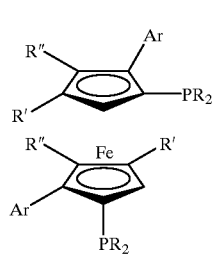
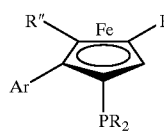

(b)

wherein R is an alkyl, aryl, substituted alkyl, substituted aryl; Ar is a susbtituted or unsubstituted aryl group; wherein Ar and R" together form an extended arene; wherein each R' and R" is independently selected from the group consisting of: H, alkyl, aryl substituted alkyl, substituted aryl, ester and alkoxy; and wherein R'—R" together form a cyclic alkyl or a extented arene;

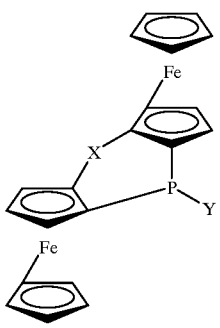

(c)

wherein X is selected from the group consisting of: CO, SO$_2$, (CH$_2$)n wherein n=0, 1 or 2, and CH=CH;

wherein Y is selected from the group consisting of: an alkyl, aryl, substituted alkyl, substituted aryl and a group represented by the formula:

—(linker)—W wherein W is represented by the formula:

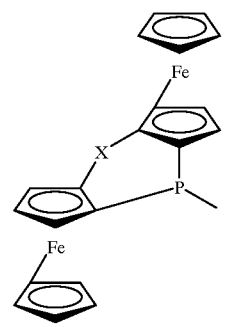

wherein X has the same meaning as above; and wherein said "linker" is selected from the group consisting of: —(CH$_2$)$_n$— where n is an integer in the range of from 1 to 8, 1,2-divalent phenyl, 2,2'-divalent-1,1'-biphenyl, 2,2'-divalent-1,1'-binaphthyl and ferrocene, and wherein each "linker" optionally has one or more substituents, each independently selected from the group consisting of: aryl, alkyl, halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine;

(d)

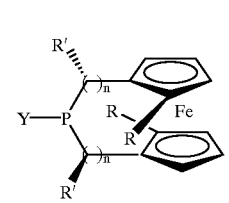

n = 0,1 wherein R is selected from the group consisting of: H, alkyl, aryl, substituted alkyl, substituted aryl, silyl, ester, amide, oxazoline and phosphate, with the proviso that R is H when R' is not H; R' is selected from the group consisting of: H, alkyl, aryl, substituted alkyl and substituted aryl; n is 0 or 1;

Y is selected from the group consisting of: alkyl, aryl, substituted alkyl, substituted aryl and a group represented by the formula:

—(linker)—W wherein W is represented by the formula:

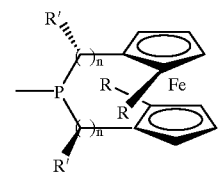

n = 0,1 wherein said "linker" is selected from the group consisting of: —(CH$_2$)$_n$— where n is an integer in the range of from 1 to 8, 1,2-divalent phenyl, 2,2'-divalent-1,1'-biphenyl, 2,2'-divalent-1,1'-binaphthyl and ferrocene, and wherein each "linker" optionally has one or more substituents, each independently selected from the group consisting of: aryl, alkyl, halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine; or

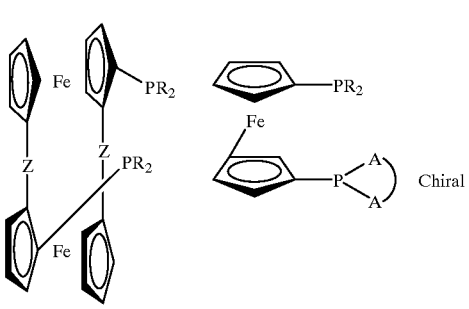

(e)

wherein R is selected from the group consisting of: alkyl, aryl, substituted alkyl and substituted aryl; Z is selected from the group consisting of: CO, SO$_2$ and —(CH$_2$)$_n$— wherein n=0, 1 or 2; each A is independently a group containing an sp$^2$ or sp$^3$ hybridized N, O, C or S atom, wherein two A groups form a cyclic compound via a chiral connecting group selected from the group consisting of: —NHR*NH—, —OR*O—, —SR*S—, —Binol— and —CH$_2$R*CH$_2$—; wherein each R* is a chiral alkyl or aryl group.

32. The catalyst of claim 31, wherein said catalyst is a racemic mixture of enantiomers.

33. The catalyst of claim 31, wherein said catalyst is a non-racemic mixture of enantiomers.

34. The catalyst of claim 31, wherein said catalyst is one of the enantiomers.

35. The catalyst of claim 31, having an optical purity of at least 85% ee.

36. The catalyst of claim 31, having an optical purity of at least 95% ee.

37. The catalyst of claim 31, wherein said transition metal is selected from the group consisting of: Ag, Pt, Pd, Rh, Ru, Ir, Cu, Ni, Mo, Ti, V, Re and Mn.

38. The catalyst of claim 37, wherein said transition metal is selected from the group consisting of: Cu, Ag, Ni, Pt, Pd, Rh, Ru and Ir.

39. The catalyst of claim 31, wherein said transition metal salt, or complex thereof, is selected from the group consisting of: AgX; Ag(OTf); Ag(OTf)$_2$; AgOAc; PtCl$_2$; H$_2$PtCl$_4$; Pd$_2$(DBA)$_3$; Pd(OAc)$_2$; PdCl$_2$(RCN)$_2$; (Pd(allyl)Cl)$_2$; Pd(PR$_3$)$_4$; (Rh(NBD)$_2$)X; (Rh (NBD)Cl)$_2$; (Rh(COD)Cl)$_2$; (Rh(COD)$_2$)X; Rh(acac)(CO)$_2$; Rh(ethylene)$_2$(acac); (Rh (ethylene)$_2$Cl)$_2$; RhCl(PPh$_3$)$_3$; Rh(CO)$_2$Cl$_2$; RuHX(L)$_2$ (diphosphine), RUX$_2$(L)$_2$ (diphosphine), Ru(arene)X$_2$ (diphosphine), Ru(aryl group)X$_2$; Ru(RCOO)$_2$ (diphosphine); Ru(methallyl)$_2$(diphosphine); Ru(aryl group)X$_2$(PPh$_3$)$_3$; Ru(COD)(COT); Ru(COD)(COT)X; RuX$_2$ (cymen); Ru(COD)n; Ru(aryl group)X$_2$(diphosphine); RuCl$_2$(COD); (Ru(COD)$_2$)X; RuX$_2$(diphosphine); RuCl$_2$ (=CHR)(PR$_3$)$_2$; Ru(ArH)Cl$_2$; Ru(COD)(methallyl)$_2$; (Ir (NBD)$_2$Cl)$_2$; (Ir(NBD)$_2$)X; (Ir(COD)$_2$Cl)$_2$; (Ir(COD)$_2$)X; CuX (NCCH$_3$)$_4$; Cu(OTf); Cu(OTf)$_2$; Cu(Ar)X; CuX; Ni(acac)$_2$; NiX$_2$; (Ni(allyl)X)$_2$; Ni(COD)$_2$; MoO$_2$(acac)$_2$; Ti(OiPr)$_4$; VO(acac)$_2$; MeReO$_3$; MnX$_2$ and Mn(acac)$_2$; wherein each R and R' is independently selected from the group consisting of: alkyl or aryl; Ar is an aryl group; and X is a counteranion.

40. The catalyst of claim 39, wherein L is a solvent and wherein said counteranion X is selected from the group consisting of: halogen, BF$_4$, B(Ar)$_4$ wherein Ar is fluorophenyl or 3,5-di-trifluoromethyl-1-phenyl, ClO$_4$, SbF$_6$, PF$_6$, CF$_3$SO$_3$, RCOO and a mixture thereof.

41. The catalyst of claim 31, prepared in situ or as an isolated compound.

42. A process for preparation of an asymmetric compound comprising:
contacting a substrate capable of forming an asymmetric product by an asymmetric reaction and a catalyst prepared by a process comprising: contacting a transition metal salt, or a complex thereof, and a ligand selected from the group consisting of compounds represented by:

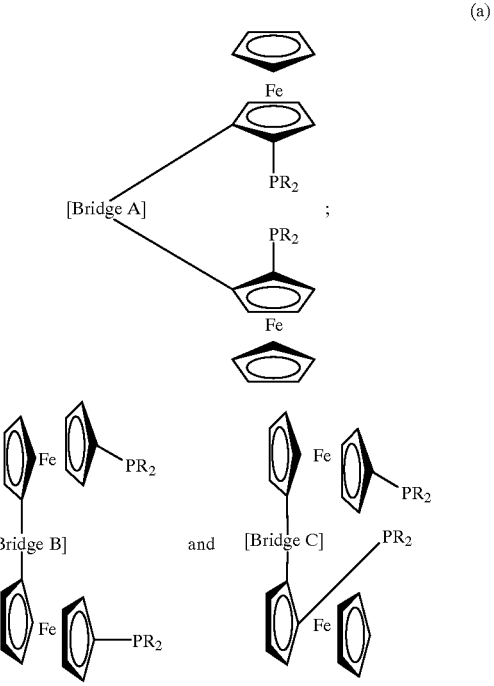

(a)

wherein "bridge A" is selected from the group consisting of: —CONH—R*—NHCO—, —CO—OR*O—CO—, —CO—R* —CO—, —CH=N—R*—N=CH—, —CH$_2$NH—R*—NHCH$_2$—, —CH$_2$NHCO—R*—CONHCH$_2$—, —C*H(R$^1$)NH—R*—NHC*H(R$^1$)—, —C*H(R$^1$)NHCO—R*—CONHC*H(R$^1$)—, —CONH—R—NHCO—, —CO—ORO—CO—, —CO—R—CO—, —CH=N—R—N=CH—, —CH$_2$NH—R—NHCH$_2$—, —CH$_2$NHCO—R—CONHCH$_2$—, —C*H(R$^1$)NH—RNH—C*H(R$^1$)—, —C*H(R$^1$)NHCO—R—CONHC*H(R$^1$)—, C=O, C=S, SO$_2$, —PO(OR$^1$)—, —PO(NHR$^1$)—, —PO(NR$^1$$_2$)—, Si(R$^1$)$_2$ —, —R—*, and —R—;

wherein "bridge B" has a stereogenic carbon center, wherein said "bridge B" is selected from the group consisting of: —CONH—R*—NHCO—, —CO—OR*O—CO—, —CO—R*—CO—, —CH=N—R*—N=CH—, —CH$_2$NH—R*—NHCH$_2$—, —CH$_2$NHCO—R*—CONHCH$_2$—, —C*H(R$^1$)NH—R*—NHC*H(R$^1$)———C*H(R$^1$)NHCO—R*—CONHC*H(R$^1$)—, —C*H(R$^1$)NH—RNH—C*H (R$^1$)—, —C*H(R$^1$)NHCO—R—CONHC*H(R$^1$)—, and —R—*;

wherein "bridge C" is selected from the group consisting of: CO, SO$_2$, CH=CH, —CONHR*NHCO— and —(CH$_2$)n— wherein n is 0, 1 or 2; and wherein R¹ is selected from the group consisting of: an alkyl, aryl, aralkyl, alkaryl, and a substituted derivative thereof; —R— is selected from the group consisting of: an alkylene, arylene and a substituted derivative thereof; and * indicates the presence of a stereogenic carbon center;

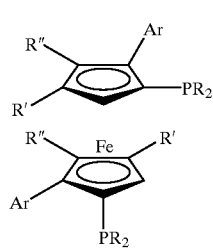

(b)

wherein R is an alkyl, aryl, substituted alkyl, substituted aryl; Ar is a susbtituted or unsubstituted aryl group; wherein Ar and R" together form an extended arene; wherein each R' and R" is independently selected from the group consisting of: H, alkyl, aryl substituted alkyl, substituted aryl, ester and alkoxy; and wherein R'—R" together form a cyclic alkyl or a extented arene;

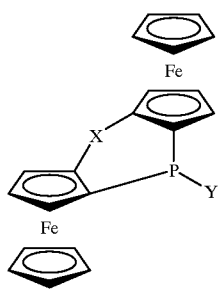

(c)

wherein X is selected from the group consisting of: CO, SO₂, (CH₂)n wherein n 0, 1 or 2, and CH=CH; wherein Y is selected from the group consisting of: an alkyl, aryl, substituted alkyl, substituted aryl and a group represented by the formula:

—(linker)—W wherein W is represented by the formula:

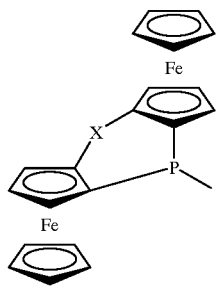

wherein X has the same meaning as above; and wherein said "linker" is selected from the group consisting of: —(CH₂)$_n$— where n is an integer in the range of from 1 to 8, 1,2-divalent phenyl, 2,2'-divalent-1,1'-biphenyl, 2,2'-divalent-1,1'-binaphthyl and ferrocene, and wherein each "linker" optionally has one or more substituents, each independently selected from the group consisting of: aryl, alkyl, halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine;

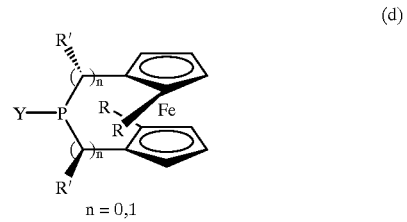

(d)

n = 0,1 wherein R is selected from the group consisting of: H, alkyl, aryl, substituted alkyl, substituted aryl, silyl, ester, amide, oxazoline and phosphate, with the proviso that R is H when R' is not H; R' is selected from the group consisting of: H, alkyl, aryl, substituted alkyl and substituted aryl; n is 0 or 1;

Y is selected from the group consisting of: alkyl, aryl, substituted alkyl, substituted aryl and a group represented by the formula:

—(linker)—W wherein W is represented by the formula:

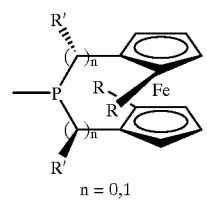

n = 0,1 wherein said "linker" is selected from the group consisting of: —(CH₂)$_n$— where n is an integer in the range of from 1 to 8, 1,2-divalent phenyl, 2,2'-divalent-1,1'-biphenyl, 2,2'-divalent-1,1'-binaphthyl and ferrocene, and wherein each "linker" optionally has one or more substituents, each independently selected from the group consisting of: aryl, alkyl, halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine; or

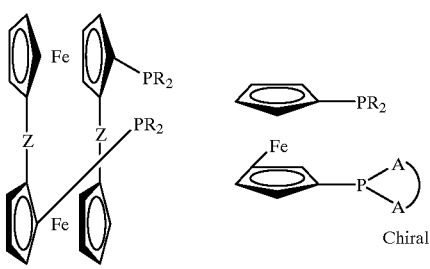

(e)

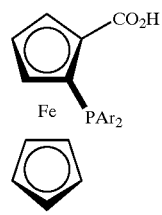

wherein each Ar is independently selected from the group consisting of: phenyl and an aryl of 6 to 22 carbon atoms, said process comprising the steps of:

providing a chiral oxazolinoferrocenyl diaryl phosphine derived from (S)-vanlinol;

sequentially contacting said chiral oxazolinoferrocenyl diaryl phosphine phosphine derived from (S)-vanlinol and:
(1) water and anhydrous sodium sulfate;
(2) trifluoroacetic acid; and
(3) an acylating agent;

to produce an N-acylated (S)-vanlinol ester of carboxyferrocenyl diaryl phosphine; and contacting said N-acylated (S)-vanlinol ester of carboxyferrocenyl diaryl phosphine, potassium tertiary butoxide and water to produce said (S)-carboxyferrocenyl diaryl phosphine.

51. The process of claim 50, wherein said oxazolinoferrocenyl diaryl phosphine derived from (S)-vanlinol is formed by a process comprising the steps of contacting ferrocenyl chloride and (S)-vanlinol in the presence of a base to produce a ferrocene amide;

contacting said ferrocene amide and an alkyl or aryl sulfonyl chloride to produce a ferrocene oxazoline; and contacting said ferrocene oxazoline with an organolithium reagent and thereafter with a diarylhalophosphine to produce said oxazolinoferrocenyl diaryl phosphine.

52. The process of claim 50, wherein said diarylhalophosphine is selected from the group consisting of: $PPh_2Cl$, $P(xylyl)_2Cl$ and $P(ph)(xylyl)Cl$.

53. The process of claim 50, wherein said acylating agent is acetic anhydride.

54. A process for preparing (S, S, S, S)-FAP 6 ligand comprising the step of contacting a carboxyferrocenyl diaryl phosphine and (1S, 2S)-diaminocyclohexane under reaction conditions sufficient to produce said (S, S, S, S)-FAP 6 ligand.

55. A non-racemic FAP 6 ligand prepared by the process of claim 54.

56. The non-racemic FAP 6 ligand of claim 55, wherein said FAP 6 ligand has an optical purity of at least 85% ee.

57. A process for preparing (S, R, R, S)-FAP 7 ligand comprising the step of contacting a carboxyferrocenyl diaryl phosphine and (1R, 2R)-diaminocyclohexane under reaction conditions sufficient to produce said (S, R, R, S)-FAP 7 ligand.

58. A non-racemic FAP 7 ligand prepared by the process of claim 56.

59. The non-racemic FAP 7 ligand of claim 58, wherein said FAP 7 ligand has an optical purity of at least 85% ee.

60. A process for preparing an (R)-carboxyferrocenyl diaryl phosphine comprising the steps of wherein R is selected from the group consisting of: alkyl, aryl, substituted alkyl and substituted aryl; Z is selected from the group consisting of: CO, $SO_2$ and —$(CH_2)_n$— wherein n=0, 1 or 2; each A is independently a group containing an $sp^2$ or $sp^3$ hybridized N, O, C or S atom, wherein two A groups form a cyclic compound via a chiral connecting group selected from the group consisting of: —NHR*NH—, —OR*O—, —SR*S—, —Binol— and —$CH_2R*CH_2$—; wherein each R* is a chiral alkyl or aryl group.

43. The process of claim 42, wherein said asymmetric reaction is selected from the group consisting of: hydrogenation, hydride transfer, allylic alkylation, hydrosilylation, hydroboration, hydrovinylation, hydroformylation, olefin metathesis, hydrocarboxylation, isomerization, cyclopropanation, Diels-Alder reaction, Heck reaction, isomerization, Aldol reaction, Michael addition; epoxidation, kinetic resolution and [m+n] cycloaddition wherein m=3 to 6 and n =2.

44. The process of claim 43, wherein said asymmetric reaction is hydrogenation and said substrate is selected from the group consisting of: imine, ketone, ethylenically unsaturated compound, enamine, enamide and vinyl ester.

45. The process of claim 43, wherein said asymmetric reaction is a silver-catalyzed asymmetric [3+2] cycloaddition of an azomethine ylide with a dipolarophile.

46. The process of claim 43, wherein said asymmetric reaction is a palladium-catalyzed allylic alkylation and said substrate is an allylic ester.

47. The process of claim 43, wherein said asymmetric palladium-catalyzed allylic alkylation reaction is a kinetic resolution reaction and said substrate is a racemic allylic ester.

48. An (R) or (S)-carboxyferrocenyl diaryl phosphine, wherein said (S)-isomer is represented by the formula:

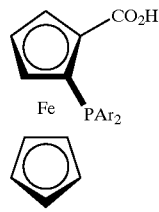

wherein each Ar is independently selected from the group consisting of: phenyl and an aryl of 6 to 22 carbon atoms.

49. The chiral compound of claim 48, wherein said aryl is xylyl.

50. A process for preparing an (S)-carboxyferrocenyl diaryl phosphine represented by the formula:

providing a chiral oxazolinoferrocenyl diaryl phosphine derived from (R)-vanlinol;

sequentially contacting said chiral oxazolinoferrocenyl diaryl phosphine phosphine derived from (R)-vanlinol and:
(1) water and anhydrous sodium sulfate;
(2) trifluoroacetic acid; and
(3) an acylating agent;

to produce an N-acylated (R)-vanlinol ester of carboxyferrocenyl diaryl phosphine; and contacting said N-acylated (R)-vanlinol ester of carboxyferrocenyl diaryl phosphine, potassium tertiary butoxide and water to produce said (R)-carboxyferrocenyl diaryl phosphine.

* * * * *